US007001595B2

(12) United States Patent
Salcedo et al.

(10) Patent No.: US 7,001,595 B2
(45) Date of Patent: Feb. 21, 2006

(54) CHEMOKINE β-7 VARIANTS

(75) Inventors: Theodora W. Salcedo, Gaithersburg, MD (US); Vikram P. Patel, Germantown, MD (US); Robert John Benjamin Nibbs, Glasgow (GB); Gerard John Graham, Glasgow (GB)

(73) Assignees: Human Genome Sciences Inc., Rockville, MD (US); Beatson Institute for Cancer Research, Glasgow (GB)

( * ) Notice: Subject to any disclaimer, the term of this patent is extended or adjusted under 35 U.S.C. 154(b) by 432 days.

(21) Appl. No.: 10/260,270

(22) Filed: Oct. 1, 2002

(65) Prior Publication Data

US 2003/0143192 A1   Jul. 31, 2003

Related U.S. Application Data

(62) Division of application No. 09/437,602, filed on Nov. 10, 1999, now Pat. No. 6,495,128.

(60) Provisional application No. 60/107,801, filed on Nov. 10, 1998.

(51) Int. Cl.
C07K 14/52 (2006.01)
C12N 5/10 (2006.01)
C12N 15/63 (2006.01)
A61K 38/19 (2006.01)

(52) U.S. Cl. .................... 424/85.1; 530/324; 435/69.5; 435/69.7; 435/71.1; 435/71.2; 435/254.11; 435/254.3; 435/320.1; 435/471

(58) Field of Classification Search ............... 424/85.1; 435/254.11, 254.3, 320.1, 325, 471, 69.5, 435/69.7, 71.1, 71.2; 530/324; 536/23.5
See application file for complete search history.

(56) References Cited

U.S. PATENT DOCUMENTS

| 4,847,325 | A | 7/1989 | Shadle et al. |
| 5,116,964 | A | 5/1992 | Capon et al. |
| 5,504,003 | A | 4/1996 | Li et al. |
| 5,605,817 | A | 2/1997 | Coleman et al. |
| 5,912,327 | A | 6/1999 | Li et al. |
| 6,001,606 | A | 12/1999 | Ruben et al. |
| 6,290,948 | B1 | 9/2001 | White et al. |
| 6,406,688 | B1 | 6/2002 | White et al. |
| 6,451,562 | B1 | 9/2002 | Ruben et al. |
| 6,488,925 | B1 | 12/2002 | Ruben et al. |
| 6,495,128 | B1 | 12/2002 | Salcedo et al. |
| 6,623,942 | B1 | 9/2003 | Ruben et al. |
| 6,632,425 | B1 | 10/2003 | Li et al. |
| 6,811,773 | B1 | 11/2004 | Gentz et al. |
| 2002/0141972 | A1 | 10/2002 | White et al. |
| 2002/0146390 | A1 | 10/2002 | White et al. |
| 2002/0155094 | A1 | 10/2002 | White et al. |
| 2003/0147846 | A1 | 8/2003 | Ruben et al. |
| 2004/0024186 | A1 | 2/2004 | Li et al. |

FOREIGN PATENT DOCUMENTS

| EP | 0 807 438 A2 | 11/1997 |
| WO | WO-94/24285 | 10/1994 |
| WO | WO-95/17092 | 6/1995 |
| WO | WO-96/22374 | 7/1996 |
| WO | WO-96/34891 | 11/1996 |
| WO | WO-97/15594 | 5/1997 |
| WO | WO-97/29125 | 8/1997 |
| WO | WO-98/14582 | 4/1998 |

OTHER PUBLICATIONS

Sherman et al. Bioassays vol. 3 No. 1, pp. 27-31, 1985.
Mikayama et al., "Molecular cloning and functional expression of a cDNA encoding glycosylation-inhibiting factor," Proc. Natl. Acad. Sci USA vol. 90, pp. 10056-10060, Nov. 1993.
Voet et al. John Wiley & Sons, Inc., pp. 126-128 and 228-234, 1990.
Adema, G.J., et al., "A dendritic-cell-derived C-C chemokine that preferentially attracts naive T cells," Nature 387:713-717 (Jun. 1997).
Mieshima, K., et al., "A Novel Human CC Chemokine PARC That is Most Homologous to Macrophage-Inflammatory Protein-1α/LD78a and Chemotactc for T Lymphocytes, but Not for Monocytes," J. Immunol. 159:1140-1149 (1997).
Millier, L., et al., GenBank Accession No. AA425047, (Oct. 1997).
Kodelia, V., et al., "Atternative Macrophage Activation-Associated CC-Chemokine-1, a Novel Structural Momologue of Macrophage Inflammatory Protein-1α with a Th2-Associated Expression Pattern," J. Immunol. 160:1411-1418 (1998).
Schall, T.J., "Biology of the Rantes/Sis Cytokine Family," Cytolone 3:165-189 (1991).
Weber, M., et al , "Deletion of the $NH_2$-Terminal Residue Converts Monocyte Chemolacic Protein 1 from an Activator of Basophil Mediator Release to an Eosinophil Chemoattractant," J. Exp. Med. 183:681-685 (1996).

(Continued)

Primary Examiner—Prema Mertz
(74) Attorney, Agent, or Firm—Human Genome Sciences, Inc.

(57) ABSTRACT

The present invention relates to deletion and substitution mutant polypeptides of human chemokine β-7 (Ckβ-7), as well as nucleic acid molecules encoding such polypeptides and processes for producing such polypeptides using recombinant techniques. In one aspect, the invention also relates to uses of the full-length and mature forms of Ckβ-7, as well as deletion and substitution mutants, in medical treatment regimens. In particular, the Ckβ-7 polypeptides described herein may be employed to treat a variety of conditions, including rheumatoid arthritis, inflammation, respiratory diseases, allergy, and IgE-mediated allergic reactions.

20 Claims, 39 Drawing Sheets

OTHER PUBLICATIONS

Wells, T.N.C, and Peitsch, M.C., "The chemokine information source: identification and characterization of novel chemokines using the WorldWideWeb and Expressed Sequence Tag Databases," J. Leukocyte Biol. 61:546-550 (1997).

Arenzana-Seisdedos et al., "HIV blocked by chemokine antagonist," Nature 383:400 (Oct. 3, 1996).

Simmons et al., "Protein Inhibition of HIV-1 Infectivity in Macrophages and Lymphocytes by a Novel CR5 Antagonist," Science 276:276-279 (Apr. 11, 1997).

Heath et al., "Chemokine Receptor Usage by Human Eosinophils," J. Clin. Invest. 99(2):178-184 (Jan. 2, 1997).

Supplementary European Search Report, Application No. EP 99 96 0251, mailed Jun. 29, 2005.

```
  1  ATGAAGGGCCTTGCAGCTGCCCTCCTTGTCCTCGTCTGCACCATGGCCCTCTGCTCCTGT  60
     M  K  G  L  A  A  A  L  L  V  L  V  C  T  M  A  L  C  S  C

61  GCACAAGTTGGTACCAACAAAGAGCTCTGCTGCCTCGTCTATACCTCCTGGCAGATTCCA  120
     A  Q  V  G  T  N  K  E  L  C  C  L  V  Y  T  S  W  Q  I  P

121  CAAAAGTTCATAGTTGACTATTCTGAAACCAGCCCCCAGTGCCCCAAGCCAGGTGTCATC  180
     Q  K  F  I  V  D  Y  S  E  T  S  P  Q  C  P  K  P  G  V  I

181  CTCCTAACCAAGAGAGGCCGGCAGATCTGTGCTGACCCCAATAAGAAGTGGGTCCAGAAA  240
     L  L  T  K  R  G  R  Q  I  C  A  D  P  N  K  K  W  V  Q  K

241  TACATCAGCGACCTGAAGCTGAATGCCTGA  270
     Y  I  S  D  L  K  L  N  A  *
```

FIG.1

```
  1  MKGLAAALLVLVCTMALC....SCAQVGTNKELCCLVYTSWQIPQKFIVD  46
     |.. .||| ||:||||||    |.: .:.... ||: |||:||||.||.|
  1  MQVSTAALAVLLCTMALCNQVLSAPLAADTPTACCFSYTSRQIPQNFIAD  50

47  YSETSPQCPKPGVILLTKRGRQICADPNKKWVQKYISDLKLNA  89
     | |||.||.||:||:|||||||:||||...||||:|||.|.|
 51  YFETSSQCSKPSVIFLTKRGRQVCADPSEEWVQKYVSDLELSA  93
```

FIG.2

```
                                  -35        Operator 1
1 AAGCTTAAAAAACTGCAAAAAATAGT TTGACT TGTGAGCGGATAACAAT -10              Operator 2
50 TAAGAT GTACCCA ATTGTGAGCGGATAACAAT TTCACACATTAA

S/D
94 A GAGGAG AAATTA CATATG
```

CHEMOKINE β-7 VARIANTS

CROSS REFERENCE TO RELATED APPLICATIONS

The present application is a divisional of U.S. application Ser. No. 09/437,602, filed Nov. 10, 1999 (now U.S. Pat. No. 6,495,128, issued on Dec. 17, 2002), which claims benefit under 35 U.S.C. § 119(e) of U.S. Provisional Application 60/107,801, filed Nov. 10, 1998, which disclosures are herein incorporated by reference.

BACKGROUND OF THE INVENTION

1. Field of the Invention

The present invention relates to deletion and substitution mutant polypeptides of human chemokine β-7 (Ckβ-7), as well as nucleic acid molecules encoding such polypeptides and processes for producing such polypeptides using recombinant techniques. In one aspect, the invention also relates to uses of the full-length and mature forms of Ckβ-7, as well as deletion and substitution mutants, in medical treatment regimens. In particular, the Ckβ-7 polypeptides described herein may be employed to treat a variety of conditions, including rheumatoid arthritis, inflammation, respiratory diseases, allergy, IgE-mediated allergic reactions, kidney diseases and may be employed for transplantation therapy. Chemokine β-7 is also known as MIP-4, PARC, AMAC1 and DCCK1.

2. Related Art

Chemokines, also referred to as intercrine cytokines, are a subfamily of structurally and functionally related cytokines. These molecules are 8–14 kd in size. In general chemokines exhibit 20% to 75% homology at the amino acid level and are characterized by four conserved cysteine residues that form two disulfide bonds. Based on the arrangement of the first two cysteine residues, chemokines have been classified into two major subfamilies, alpha and beta. In the alpha subfamily, the first two cysteines are separated by one amino acid and hence are referred to as the "C-X-C" subfamily. In the beta subfamily, the two cysteines are in an adjacent position and are, therefore, referred to as the -C—C-subfamily. Thus far, at least eight different members of this family have been identified in humans. More recently, two additional chemokine families, the C and $CX_3C$ families, have been described.

The intercrine cytokines exhibit a wide variety of functions. A hallmark feature is their ability to elicit chemotactic migration of distinct cell types, including monocytes, neutrophils, T lymphocytes, eosinophils, basophils and fibroblasts. Many chemokines have proinflammatory activity and are involved in multiple steps during an inflammatory reaction. These activities include stimulation of histamine release, lysosomal enzyme and leukotriene release, increased adherence of target immune cells to endothelial cells, enhanced binding of complement proteins, induced expression of granulocyte adhesion molecules and complement receptors, and respiratory burst. In addition to their involvement in inflammation, certain chemokines have been shown to exhibit other activities. For example, macrophage inflammatory protein I (MIP-1) is able to suppress hematopoietic stem cell proliferation, platelet factor-4 (PF-4) is a potent inhibitor of endothelial cell growth, Interleukin-8 (IL-8) promotes proliferation of keratinocytes, and GRO is an autocrine growth factor for melanoma cells.

In light of the diverse biological activities, it is not surprising that chemokines have been implicated in a number of physiological and disease conditions, including lymphocyte trafficking, wound healing, hematopoietic regulation and immunological disorders such as allergy, asthma and arthritis. An example of a hematopoietic lineage regulator is MIP-1. MIP-1 was originally identified as an endotoxin-induced proinflammatory cytokine produced from macrophages. Subsequent studies have shown that MIP-1 is composed of two different, but related, proteins MIP-1α and MIP-1β. Both MIP-1α and MIP-1β are chemo-attractants for macrophages, monocytes and T lymphocytes. Interestingly, biochemical purification and subsequent sequence analysis of a multipotent stem cell inhibitor (SCI) revealed that SCI is identical to MIP-1β. Furthermore, it has been shown that MIP-1 can counteract the ability of MIP-1α to suppress hematopoietic stem cell proliferation. This finding leads to the hypothesis that the primary physiological role of MIP-1 is to regulate hematopoiesis in bone marrow, and that the proposed inflammatory function is secondary. The mode of action of MIP-1α as a stem cell inhibitor relates to its ability to block the cell cycle at the $G_2S$ interphase. Furthermore, the inhibitory effect of MIP-1α seems to be restricted to immature progenitor cells and it is actually stimulatory to late progenitors in the presence of granulocyte macrophage-colony stimulating factor (GM-CSF).

Murine MIP-1 is a major secreted protein from lipopolysaccharide stimulated RAW 264.7, a murine macrophage tumor cell line. It has been purified and found to consist of two related proteins, MIP-1α and MIP-1β.

Several groups have cloned what are likely to be the human homologs of MIP-1α and MIP-1β. In all cases, cDNAs were isolated from libraries prepared against activated T-cell RNA.

MIP-1 proteins can be detected in early wound inflammation cells and have been shown to induce production of IL-1 and IL-6 from wound fibroblast cells. In addition, purified native MIP-1 (comprising MIP-1, MIP-1α and MIP-1β polypeptides) causes acute inflammation when injected either subcutaneously into the footpads of mice or intracisternally into the cerebrospinal fluid of rabbits (Wolpe and Cerami, *FASEB J.* 3:2565–73 (1989)). In addition to these proinflammatory properties of MIP-1, which can be direct or indirect, MIP-1 has been recovered during the early inflammatory phases of wound healing in an experimental mouse model employing sterile wound chambers (Fahey, et al. *Cytokine,* 2:92 (1990)). For example, International Patent Application Serial No. PCT/US92/05198 filed by Chiron Corporation, discloses a DNA molecule which is active as a template for producing mammalian macrophage inflammatory proteins (MIPs) in yeast.

The murine MIP-1α and MIP-1β are distinct but closely related cytokines. Partially purified mixtures of the two proteins affect neutrophil function and cause local inflammation and fever. MIP-1α has been expressed in yeast cells and purified to homogeneity. Structural analysis confirmed that MIP-1α has a very similar secondary and tertiary structure to platelet factor 4 (PF-4) and interleukin 8 (IL-8) with which it shares limited sequence homology. It has also been demonstrated that MIP-1α is active in vivo to protect mouse stem cells from subsequent in vitro killing by tritiated thymidine. MIP-1α was also shown to enhance the proliferation of more committed progenitor granulocyte macrophage colony-forming cells in response to granulocyte macrophage colony-stimulating factor. (Clemens, J. M. et al., *Cytokine* 4:76–82 (1992)).

There are four forms of monocyte chemotactic protein, namely, MCP-1, MCP-2, MCP-3 and MCP-4. All of these proteins have been structurally and functionally characterized and have also been cloned and expressed. MCP-1 and MCP-2 have the ability to attract leukocytes (monocytes, and leukocytes), while MCP-3 also attracts eosinophils and T lymphocytes (Dahinderi, E., et al., *J. Exp. Med.* 179: 751–756 (1994)). MCP-4 attracts eosinophils and monocytes (Garcia-Zapeda, E. A., et al., *J. Immunol.* 157:5613 (1996); Uguccioni, M., et al., *J. Exp. Med.* 183:2379 (1996); Forssmann, U., et al., *J. Exp. Med.* 185:2171 (1997)).

Human MCP-1 is a basic peptide of 76 amino acids with a predicted molecular mass of 8,700 daltons. MCP-1 is inducibly expressed mainly in monocytes, endothelial cells and fibroblasts. Leonard, E. J. and Yoshimura, T., *Immunol. Today* 11:97–101 (1990). The factors which induce this expression is IL-1, TNF or lipopolysaccharide treatment.

Other properties of MCP-1 include the ability to strongly activate mature human basophils in a pertussis toxin-sensitive manner. MCP-1 is a cytokine capable of directly inducing histamine release by basophils, (Bischoff, S. C., et al., *J. Exp. Med.* 175:1271–1275 (1992)). Furthermore, MCP-1 promotes the formation of leukotriene C4 by basophils pretreated with Interleukin 3, Interleukin 5, or granulocyte/macrophage colony-stimulating factor. MCP-1 induced basophil mediator release may play an important role in allergic inflammation and other pathologies expressing MCP-1.

Clones having a nucleotide sequence encoding a human monocyte chemotactic and activating factor (MCAF) reveal the primary structure of the MCAF polypeptide to be composed of a putative signal peptide sequence of 23 amino acid residues and a mature MCAF sequence of 76 amino acid residues. Furutani, Y. H., et al., *Biochem. Biophys. Res. Commu.* 159:249–55 (1989). The complete amino acid sequence of human glioma-derived monocyte chemotactic factor (GDCF-2) has also been determined. This peptide attracts human monocytes but not neutrophils. It was established that GDCF-2 comprises 76 amino acid residues. The peptide chain contains 4 half-cysteines, at positions 11, 12, 36 and 52, which create a pair of loops, clustered at the disulfide bridges. Further, the MCP-1 gene has been designated to human chromosome 17. Mehrabian, M. R., et al., *Genomics* 9:200–3 (1991).

Certain data suggests that a potential role for MCP-1 is mediating monocytic infiltration of the artery wall. Monocytes appear to be central to atherogenesis both as the progenitors of foam cells and as a potential source of growth factors mediating intimal hyperplasia. Nelken, N. A., et al., *J. Clin. Invest.* 88:1121–7 (1991). It has also been found that synovial production of MCP-1 may play an important role in the recruitment of mononuclear phagocytes during inflammation associated with rheumatoid arthritis and that synovial tissue macrophages are the dominant source of this cytokine. MCP-1 levels were found to be significantly higher in synovial fluid from rheumatoid arthritis patients compared to synovial fluid from osteoarthritis patients or from patients with other arthritides. Koch, A. E., et al., *J. Clin. Invest.* 90:772–9 (1992).

MCP-2 and MCP-3 are classified in a subfamily of proinflammatory proteins and are functionally related to MCP-1 because they specifically attract monocytes, but not neutrophils. Van Damme, J., et al., *J. Exp. Med.* 176:59–65 (1992). MCP-3 shows 71% and 58% amino acid homology to MCP-1 and MCP-2 respectively. MCP-3 is an inflammatory cytokine that regulates macrophage functions.

The transplantation of hemolymphopoietic stem cells has been proposed in the treatment of cancer and hematological disorders. Many studies demonstrate that transplantation of hematopoietic stem cells harvested from the peripheral blood has advantages over the transplantation of marrow-derived stem cells. Due to the low number of circulating stem cells, there is a need for induction of pluripotent marrow stem cell mobilization into the peripheral blood. Reducing the amount of blood to be processed to obtain an adequate amount of stem cells would increase the use of autotransplantation procedures and eliminate the risk of graph versus host reaction connected with allotransplantation. Presently, blood mobilization of marrow $CD34^+$ stem cells is obtained by the injection of a combination of agents, including antiblastic drugs and G-CSF or GM-CSF. Drugs which are capable of stem cell mobilization include IL-1, IL-7, IL-8, and NIP-1a. Both IL-1 and IL-8 demonstrate proinflammatory activity that may be dangerous for good engrafting. IL-7 must be administered at high doses over a long duration and MIP-1a is not very active as a single agent and shows best activity when in combination with G-CSF.

SUMMARY OF THE INVENTION

In one aspect, the present invention provides deletion and substitution mutants of human chemokine Ckβ-7, as well as biologically active and diagnostically or therapeutically useful derivatives thereof.

In accordance with another aspect of the present invention, there are provided isolated nucleic acid molecules encoding polypeptides of the present invention including mRNAs, DNAs, cDNAs, genomic DNAs, as well as analogs and biologically active and diagnostically or therapeutically useful fragments, analogs and derivatives thereof.

The present invention further provides isolated nucleic acid molecules comprising polynucleotides which encode mutants of the Ckβ-7 polypeptide having the amino acid sequence shown in FIG. 1 (SEQ ID NO:2) or the amino acid sequence encoded by the cDNA clone deposited in a bacterial host as ATCC Deposit Number 75675 on Feb. 9, 1994. The nucleotide sequence determined by sequencing the deposited Ckβ-7 clone, which is shown in FIG. 1 (SEQ ID NO:1), contains an open reading frame encoding a polypeptide of 89 amino acid residues, with a leader sequence of about 20 amino acid residues, and a predicted molecular weight of about 8 kDa in non-glycosylated form, and about 8–14 kDa in glycosylated form, depending on the extent of glycoslyation. The amino acid sequence of full-length and mature forms of the Ckβ-7 protein is also shown in FIG. 1 (SEQ ID NO:2).

Thus, one aspect of the invention provides an isolated nucleic acid molecule comprising a polynucleotide having a nucleotide sequence selected from the group consisting of: (a) a nucleotide sequence encoding an N-terminal deletion mutant of the Ckβ-7 polypeptide having the complete amino acid sequence in FIG. 1 (SEQ ID NO:2), wherein said deletion mutant has one or more deletions at the N-terminus; (b) a nucleotide sequence encoding an C-terminal deletion mutant of the Ckβ-7 polypeptide having the complete amino acid sequence in FIG. 1 (SEQ ID NO:2), wherein said deletion mutant has one or more deletions at the C-terminus; (c) a nucleotide sequence encoding a deletion mutant of the Ckβ-7 polypeptide having the complete amino acid sequence in FIG. 1 (SEQ ID NO:2), wherein said deletion mutant has one or more deletions at the N- and C-termini; (d) a nucleotide sequence encoding an N-terminal deletion mutant of the Ckβ-7 polypeptide encoded by the cDNA clone contained in ATCC Deposit No. 75675, wherein said deletion mutant has one or more deletions at the N-terminus; (e) a nucleotide sequence encoding a C-terminal deletion mutant of the Ckβ-7 polypeptide encoded by the cDNA clone contained in ATCC Deposit No. 75675, wherein said deletion mutant has one or more deletions at the C-terminus; (f) a nucleotide sequence encoding a deletion mutant of the Ckβ-7 polypeptide encoded by the cDNA clone contained in ATCC Deposit No. 75675, wherein said deletion mutant has one or more deletions at the N- and C-termini; and (g) a nucleotide sequence complementary to any of the nucleotide sequences in (a), (b), (c), (d), (e) or (f) above.

Further embodiments of the invention include isolated nucleic acid molecules that comprise a polynucleotide having a nucleotide sequence at least 90% homologous or identical, and more preferably at least 95%, 96%, 97%, 98%, or 99% identical, to any of the nucleotide sequences in (a), (b), (c), (d), (e), (f) or (g), above, or a polynucleotide which hybridizes under stringent hybridization conditions to a polynucleotide in (a), (b), (c), (d), (e), (f) or (g), above. These polynucleotides which hybridize do not hybridize under stringent hybridization conditions to a polynucleotide having a nucleotide sequence consisting of only A residues or of only T residues.

The Ckβ-7 deletion mutant polypeptides encoded by each of the above nucleic acid molecules may have an N-terminal methionine residue.

The present invention also relates to recombinant vectors, which include the isolated nucleic acid molecules of the present invention, and to host cells containing the recombinant vectors, as well as to methods of making such vectors and host cells.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

The invention further provides an isolated Ckβ-7 polypeptide having an amino acid sequence selected from the group consisting of: (a) the amino acid sequence of an N-terminal deletion mutant of the Ckβ-7 polypeptide having the complete amino acid sequence in FIG. 1 (SEQ ID NO:2), wherein said deletion mutant has one or more deletions at the N-terminus; (b) the amino acid sequence of an C-terminal deletion mutant of the Ckβ-7 polypeptide having the complete amino acid sequence in FIG. 1 (SEQ ID NO:2), wherein said deletion mutant has one or more deletions at the C-terminus; (c) the amino acid sequence of a deletion mutant of the Ckβ-7 polypeptide having the complete amino acid sequence in FIG. 1 (SEQ ID NO:2), wherein said deletion mutant has one or more deletions at the N- and C-termini; (d) the amino acid sequence of an N-terminal deletion mutant of the Ckβ-7 polypeptide encoded by the cDNA clone contained in ATCC Deposit No. 75675, wherein said deletion mutant has one or more deletions at the N-terminus; (e) the amino acid sequence of a C-terminal deletion mutant of the Ckβ-7 polypeptide encoded by the cDNA clone contained in ATCC Deposit No. 75675, wherein said deletion mutant has one or more deletions at the C-terminus; and (f) the amino acid sequence of the Ckβ-7 polypeptide encoded by the cDNA clone contained in ATCC Deposit No. 75675, wherein said deletion mutant has one or more deletions at the N- and C-termini.

Polypeptides of the present invention also include homologous polypeptides and substitution mutants having an amino acid sequence with at least 90% identity, and more preferably at least 95% identity to those described in (a), (b), (c), (d), (e) or (f) above, as well as polypeptides having an amino acid sequence at least 80% identical, more preferably at least 90% identical, and still more preferably 95%, 96%, 97%, 98% or 99% identical to those above.

An additional embodiment of this aspect of the invention relates to a peptide or polypeptide which has the amino acid sequence of an epitope bearing portion of a Ckβ-7 polypeptide having an amino acid sequence described in (a), (b), (c), (d), (e) or (f) above.

An additional nucleic acid embodiment of the invention relates to an isolated nucleic acid molecule comprising a polynucleotide which encodes the amino acid sequence of an epitope-bearing portion of a Ckβ-7 polypeptide having an amino acid sequence in (a), (b), (c), (d), (e) or (f), above.

Further, each of the above Ckβ-7 polypeptide deletion mutants may have an N-terminal methionine which may or may not be encoded by the nucleotide sequence shown in SEQ ID NO:1.

The present invention also provides, in another aspect, pharmaceutical compositions comprising a Ckβ-7 polynucleotide, probe, vector, host cell, polypeptide, fragment, variant, derivative, epitope bearing portion, antibody, antagonist or agonist.

In accordance with yet a further aspect of the present invention, there is provided a process for utilizing such polypeptide, or polynucleotide encoding such polypeptide for therapeutic purposes, for example, for treating rheumatoid arthritis, inflammation, respiratory diseases, allergy, and IgE-mediated allergic reactions, kidney diseases and may be employed for transplantation therapy.

An additional aspect of the invention is related to a method for treating an individual in need of an increased level of Ckβ-7 activity in the body comprising administering to such an individual a composition comprising a therapeutically effective amount of an isolated Ckβ-7 polypeptide.

A still further aspect of the invention is related to a method for treating an individual in need of a decreased level of Ckβ-7 activity in the body comprising, administering to such an individual a composition comprising a therapeutically effective amount of a Ckβ-7 antagonist of the invention. Such antagonists include the full-length and mature Ckβ-7 polypeptides shown in FIG. 1 (SEQ ID NO:2), as well as Ckβ-7 fragments (e.g., a Ckβ-7 fragment having amino acids 22 to 89 in SEQ ID NO:2).

In accordance with yet a further aspect of the present invention, there are provided antibodies against Ckβ-7 polypeptides. In another embodiment, the invention provides an isolated antibody that binds specifically to a Ckβ-7 polypeptide having an amino acid sequence described in (a), (b), (c), (d), (e) or (f) above.

The invention further provides methods for isolating antibodies that bind specifically to a Ckβ-7 polypeptide having an amino acid sequence as described herein.

In accordance with another aspect of the present invention, there are provided agonists of Ckβ-7 polypeptide activities which mimic the polypeptide of the present invention and thus have one or more Ckβ-7 polypeptide activity.

In accordance with yet another aspect of the present invention, there are provided chemokine antagonists. These chemokine antagonists may be used to inhibit the action of chemokines, for example, in the treatment of rheumatoid arthritis, inflammation, respiratory diseases, allergy, and IgE-mediated allergic reactions, kidney diseases and may be employed for transplantation therapy.

In accordance with yet a further aspect of the present invention, there is also provided nucleic acid probes comprising nucleic acid molecules of sufficient length to specifically hybridize to a nucleic acid sequence of the present invention.

The present invention also provides a screening method for identifying compounds capable of enhancing or inhibiting a cellular response induced by a chemokine polypeptide. This method involves contacting cells which express a receptor to which a chemokine polypeptide binds with the candidate compound, assaying a cellular response induced by the chemokine polypeptide, and comparing the cellular response to a standard cellular response, the standard being assayed when contact is made in absence of the candidate compound; whereby, an increased cellular response over the standard) indicates that the compound is an agonist and a decreased cellular response over the standard indicates that the compound is an antagonist. The above referenced receptor will generally be one which binds a chemokine other than Ckβ-7, wherein the activity induced by this other chemokine is inhibited by the candidate compound. Often this candidate compound will be a Ckβ-7 polypeptide.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIG. 1 depicts the cDNA sequence (SEQ ID NO:1) and corresponding determined amino acid sequence (SEQ ID NO:2) of Ckβ-7. The 89 amino acid sequence shown is the full length protein, with approximately the first 20 amino acids representing a leader sequence (underlined) such that the mature form of the protein is 69 amino acids in length. The standard one letter abbreviations for amino acids are used.

FIG. 2 displays two amino acid sequences wherein, the top sequence is the human Ckβ-7 amino acid sequence (SEQ ID NO:2) and the bottom sequence is human MIP-1α (Human Tonsillar lymphocyte LD78 Beta protein precursor) (SEQ ID NO:3).

FIG. 10A is a control for this panel of experiments and shows calcium flux in eosinophils in the presence of 10 ng/ml Eotaxin. FIG. 10B shows calcium flux in eosinophils in the presence of 10 ng/ml Eotaxin and 1 μg/ml Ckβ-7 (40% in the form of a Ckβ-7 fragment having amino acids 21–89 in SEQ ID NO:2 and 60% having amino acids 25–89 in SEQ ID NO:2).

FIGS. 21A–21E-1 show that Met-Ckβ7* prevents signaling through CCR3 induced by eotaxin, MCP4, RANTES and eotaxin2. Fura-2-loaded HOS-CCR3 cells (panels A–D-1) or peripheral blood mononuclear cells (panels E–E-1) stimulated at 37° C. with agonist in the absence (left panels) or presence (right panels) of 500 nM Met-Ckβ-7*. Fluorescence emission is recorded every 0.1 sec for 100 sec (340 nm ($\lambda_{ex}$); 500 nm ($\lambda_{em}$)).

DETAILED DESCRIPTION OF THE PREFERRED EMBODIMENTS

The present invention provides diagnostic or therapeutic compositions and methods that utilize isolated polynucleotide molecules encoding Ckβ-7 polypeptides, or the Ckβ-7 polypeptides themselves, as well as vectors, host cells and recombinant or synthetic methods for producing such compositions. Other names for Ckβ-7 are MIP-4, PARC, AMAC1 and DCCK1.

Nucleic Acids

Figure 21A:
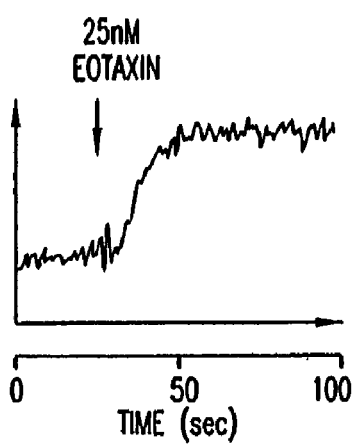
Figures 1, 21A:
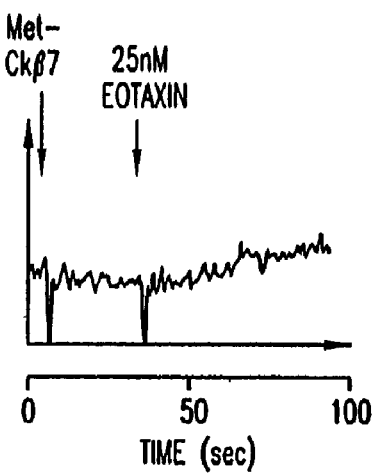
Figure 21B:
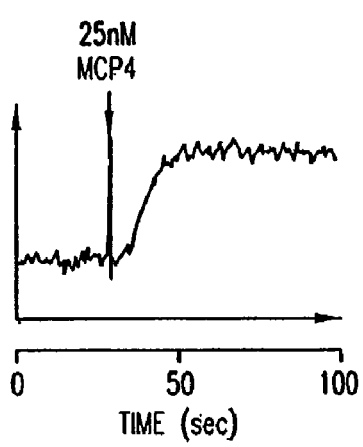
Figures 1, 21B:
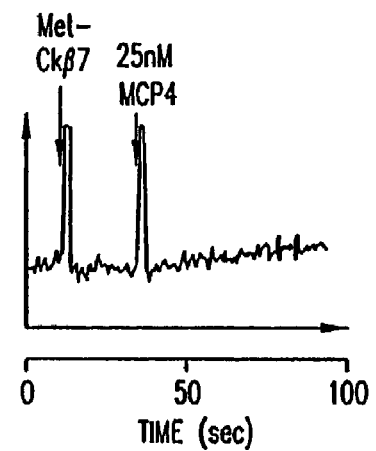
Figure 21C:
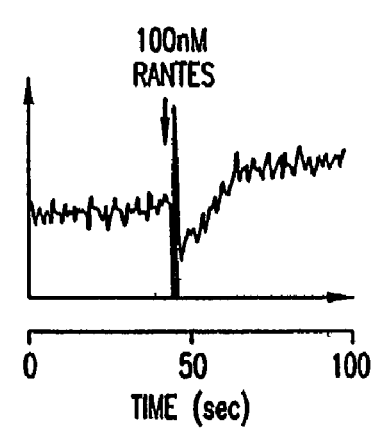
Figures 1, 21C:
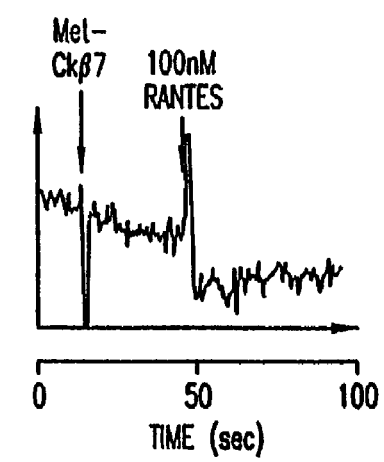
Figure 21D:
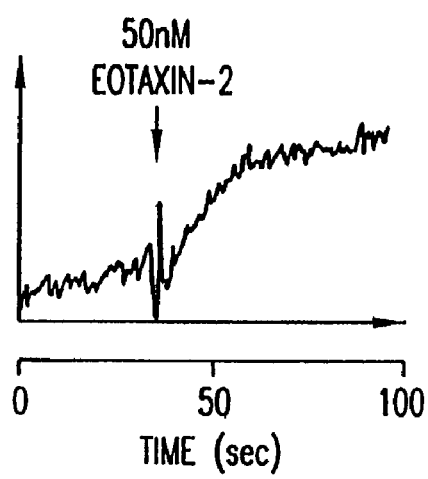
Figures 1, 21D:
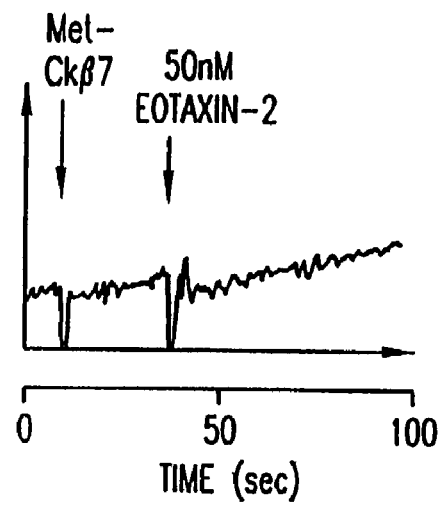

In accordance with one aspect of the present invention, there are provided isolated nucleic acid (polynucleotide) molecules which encode deletion and substitution mutants of either the Ckβ-7 polypeptide having the deduced amino acid sequence of FIG. 1 (SEQ ID NO:2) or the Ckβ-7 polypeptide encoded by the cDNA of the clone deposited at the American Type Culture Collection, 10801 University Blvd., Manassas, Va. 20110-2209, USA, as ATCC Deposit No. 75675 on Feb. 9, 1994.

The deposit referred to herein will be maintained under the terms of the Budapest Treaty on the International Recognition of the Deposit of Micro-organisms for purposes of Patent Procedure. The deposit is provided merely as convenience to those of skill in the art and is not an admission that a deposit is required under 35 U.S.C. §112. The sequence of the polynucleotide contained in the deposited materials, as well as the amino acid sequence of the polypeptides encoded thereby, are incorporated herein by reference and are controlling in the event of any conflict with any description of sequences herein. A license may be required to make, use or sell the deposited material, and no such license is hereby granted.

The polynucleotide encoding Ckβ-7 (SEQ ID NO:1) was derived from a human adult lung cDNA library and contains an open reading frame encoding a polypeptide of 89 amino acid residues (SEQ ID NO:2), which exhibits significant homology to a number of chemokines. The top match is to the human tonsillar lymphocyte LD78 beta protein (SEQ ID NO:3), showing 60% identity and 89% similarity (FIG. 2). Furthermore, the four cysteine residues occurring in all chemokines in a characteristic motif are conserved in both clone(s). The fact that the first two cysteine residues in the genes are in adjacent positions classifies them as "C—C" or β subfamily of chemokines. In the other subfamily, the "CXC" or a subfamily, the first two cysteine residues are separated by one amino acid.

Unless otherwise indicated, each nucleotide sequence set forth herein is presented as a sequence of deoxyribonucleotides (abbreviated A, G, C and T). However, by nucleotide sequence of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to an RNA molecule having the sequence of SEQ ID NO:1, as set forth using deoxyribonucleotide abbreviations, is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

The present invention further provides polynucleotides which encode Ckβ-7 polypeptides having one or more residues deleted from the amino terminus of the amino acid sequence shown in SEQ ID NO:2, up to the cysteine residue at position number 30, and polynucleotides encoding such polypeptides. In particular, the present invention provides polynucleotides which encode polypeptides comprising the amino acid sequence of residues n-89 of SEQ ID NO:2, where n is an integer in the range of 1 to 75, and preferably n is in the range of 15 to 30, where Cys-30 is the position of the first residue from the N-terminus the Ckβ-7 polypeptide (shown in SEQ ID NO:2) believed to be required for receptor binding activity. Further, n may be in the range of 22–30, 23–30, 24–30, 25–30, 26–30, 27–30, 28–30 or 29–30.

More in particular, the invention provides polynucleotides which encode polypeptides comprising the amino acid sequence shown in SEQ ID NO:2 as residues 1–89, 2–89, 3–89, 4–89, 5–89, 6–89, 7–89, 8–89, 9–89, 10–89, 11–89, 12–89, 13–89, 14–89, 15–89, 16–89, 17–89, 18–89, 19–89, 20–89, 21–89, 22–89, 23–89, 24–89, 25–89, 26–89, 27–89, 28–89, 29–89, 30–89, 31–89, 32–89, 33–89, 34–89, 35–89, 36–89, 37–89, 38–89, 39–89, 40–89, 41–89, 42–89, 43–89, 44–89, 45–89, 46–89, 47–89, 48–89, 49–89, 50–89, 51–89, 52–89, 53–89, 54–89, 55–89, 56–89, 57–89, 58–89, 59–89, 60–89, 61–89, 62–89, 63–89, 64–89, 65–89, 66–89, 67–89, 68–89, 69–89, 70–89, 71–89,7 2–89, 73–89, 74–89 or 75–89. Particularly preferred are polynucleotides which encode polypeptides comprising the amino acid sequence shown in SEQ ID NO:2 as residues 15–89, 16–89, 17–89, 18–89, 19–89, 20–89, 21–89, 22–89, 23–89, 24–89, 25–89, 26–89, 27–89, 28–89, 29–89 or 30–89.

The present invention further provides polynucleotides which encode polypeptides having one or more residues deleted from the carboxy terminus of the amino acid sequence of the Ckβ-7 polypeptide up to the cysteine residue at position 70 of SEQ ID NO:2. In particular, the present invention provides polynucleotides which encode polypeptides having the amino acid sequence of residues 1-m of the amino acid sequence in SEQ ID NO:2, where m is any integer in the range of 15 to 89, preferably the polypeptide comprises residues 20-m is in the range of 70–89 since residue cysteine-70 is the first residue from the C-terminus of the complete Ckβ-7 polypeptide (shown in SEQ ID NO:2) believed to be required for receptor binding and target cell modulation activities. Further, m may be in the range of 71–89, 72–89, 73–89, 74–89, 75–89, 76–89, 77–89, 78–89, 79–89, 80–89, 81–89, 82–89, 83–89, 84–89, 85–89, 86–89, 87–89 or 88–89.

More in particular, the invention provides polynucleotides which encode polypeptides comprising the amino acid sequence shown in SEQ ID NO:2 as residues 1–15, 1–16, 1–17, 1–18, 1–19, 1–20, 1–21, 1–22, 1–23, 1–24, 1–25, 1–26, 1–27, 1–28, 1–29, 1–30, 1–31, 1–32, 1–33, 1–34, 1–35, 1–36, 1–37, 1–38, 1–39, 1–40, 1–41, 1–42, 1–43, 1–44, 1–45, 1–46, 1–47, 1–48, 1–49, 1–50, 1–51, 1–52, 1–53, 1–54, 1–55, 1–56, 1–57, 1–58, 1–59, 1–60, 1–61, 1–62, 1–63, 1–64, 1–65, 1–66, 1–67, 1–68, 1–69, 1–70, 1–71, 1–72, 1–73, 1–74, 1–75, 1–76, 1–77, 1–78, 1–79, 1–80, 1–81, 1–82, 1–83, 1–84, 1–85, 1–86, 1–87, 1–88 or 1–89. Particularly preferred are polynucleotides which encode polypeptides comprising the amino acid sequence shown in SEQ ID NO:2 as residues 20–70, 20–71, 20–72, 20–73, 20–74, 20–75, 20–76, 20–77, 20–78, 20–79, 20–80, 20–81, 20–82, 20–83, 20–84, 20–85, 20–86, 20–87, 20–88 or 20–89.

The invention also provides polynucleotides which encode Ckβ-7 polypeptides having one or more amino acids deleted from both the amino and the carboxyl termini of the full-length polypeptide which may be described generally as having residues n–m of SEQ ID NO:2, where n and m are integers as described above.

Particularly preferred are polynucleotides which encode Ckβ-7 polypeptides having N- and C-terminal deletions, including the polypeptides comprising amino acid residues 21–89, 22–89, 23–89, 24–89, 25–89, 26–89, 27–89, 28–89, 29–89, 30–89, 21–88, 22–88, 23–88, 24–88, 25–88, 26–88, 27–88, 28–88, 29–88, 30–88, 21–87, 22–87, 23–87, 24–87, 25–87, 26–87, 27–87, 28–87, 29–87, 30–87, 21–86, 22–86, 23–86, 24–86, 25–86, 26–86, 27–86, 28–86, 29–86, 30–86, 21–85, 22–85, 23–85, 24–85, 25–85, 26–85, 27–85, 28–85, 29–85, 30–85, 21–84, 22–84, 23–84, 24–84, 25–84, 26–84, 27–84, 28–84, 29–84, 30–84, 21–83, 22–83, 23–83, 24–83, 25–83, 26–83, 27–83, 28–83, 29–83, 30–83, 21–82, 22–82, 23–82, 24–82, 25–82, 26–82, 27–82, 28–82, 29–82, 30–82, 21–81, 22–81, 23–81, 24–81, 25–81, 26–81, 27–81, 28–81, 29–81, 30–81, 21–80, 22–80, 23–80, 24–80, 25–80, 26–80, 27–80, 28–80, 29–80, 30–80, 21–79, 22–79, 23–79, 24–79, 25–79, 26–79, 27–79, 28–79, 29–79, 30–79, 21–78, 22–78, 23–78, 24–78, 25–78, 26–78, 27–78, 28–78, 29–78, 30–78, 21–77, 22–77, 23–77, 24–77, 25–77, 26–77, 27–77, 28–77, 29–77, 30–77, 21–76, 22–76, 23–76, 24–76, 25–76, 26–76, 27–76, 28–76, 29–76, 30–76, 21–75, 22–75, 23–75, 24–75, 25–75, 26–75, 27–75, 28–75, 29–75, 30–75, 21–74, 22–74, 23–74, 24–74, 25–74, 26–74, 27–74, 28–74, 29–74, 30–74, 21–73, 22–73, 23–73, 24–73, 25–73, 26–73, 27–73, 28–73, 29–73, 30–73, 21–72, 22–72, 23–72, 24–72, 25–72, 26–72, 27–72, 28–72, 29–72, 30–72, 21–71, 22–71, 23–71, 24–71, 25–71, 26–71, 27–71, 28–71, 29–71, 30–71, 21–70, 22–70, 23–70, 24–70, 25–70, 26–70, 27–70, 28–70, 29–70 or 30–70.

Also particularly preferred are polynucleotides which encode Ckβ-7 polypeptides comprising amino acid residues: 16–89, 17–89, 18–89, 19–89, 16–88, 17–88, 18–88, 19–88, 16–87, 17–87, 18–87, 19–87, 16–86, 17–86, 18–86, 19–86, 16–85, 17–85, 18–85, 19–85, 16–84, 17–84, 18–84, 19–84, 16–83, 17–83, 18–83, 19–83, 16–82, 17–82, 18–82, 19–82, 16–81, 17–81, 18–81, 19–81, 16–80, 17–80, 18–80, 19–80, 16–79, 17–79, 18–79, 19–79, 16–78, 17–78, 18–78, 19–78, 16–77, 17–77, 18–77, 19–77, 16–76, 17–76, 18–76, 19–76, 16–75, 17–75, 18–75, 19–75, 16–74, 17–74, 18–74, 19–74, 16–73, 17–73, 18–73, 19–73, 16–72, 17–72, 18–72, 19–72, 16–71, 17–71, 18–71, 19–71, 16–70, 17–70, 18–70 or 19–70.

Also included are polynucleotides which encode portions of the complete Ckβ-7 amino acid sequence encoded by the cDNA clone contained in ATCC Deposit No. 75675, where this portion excludes from 1 to about 29 amino acids from the amino terminus of the complete polypeptide encoded by the human cDNA in the clone contained in ATCC Deposit No. 75675, or from 1 to about 19 amino acids from the carboxy terminus, or any combination of the above amino terminal and carboxy terminal deletions of the full-length polypeptide encoded by the human cDNA in the clone contained in ATCC Deposit No. 75675.

Most particularly preferred are polynucleotides which encode any of the above-listed N- and C-terminal Ckβ-7 deletion mutants having an N-terminal methionine added to its amino terminus represented herein, for example, as Met-22–89.

Thus, the term "polynucleotide encoding a polypeptide" encompasses a polynucleotide which includes only coding sequence for the polypeptide as well as a polynucleotide which includes additional coding and/or non-coding sequence.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIG. 1, a nucleic acid molecule encoding a Ckβ-7 polypeptide may be obtained using standard cloning and screening procedures, such as those for cloning cDNAs using mRNA as starting material. Further, using the information provided herein and standard techniques, nucleic acid molecules encoding deletion mutant Ckβ-7 polypeptides of the invention may also be obtained.

The present invention thus relates to variants of the herein above described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

The present invention further includes polynucleotides encoding deletion variants, substitution variants and addition or insertion variants. These variants, however, will generally not include variants which contain amino acids added to the N- and C-termini that are normally present in the naturally occurring Ckβ-7 polypeptide (e.g., a nucleotide variant encoding amino acids 22 to 89 in SEQ ID NO:2 to which a nucleotide sequence encoding alanine has been added to the 5' terminus).

The present invention also includes polynucleotides, wherein the coding sequence for the Ckβ-7 polypeptide may be fused in the same reading frame to a polynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

The polynucleotides of the present invention can also have the coding sequence fused in frame to a marker sequence which allows for purification of the polypeptide of the present invention. The marker sequence can be a hexa-histidine tag supplied by a pQE-9 vector to provide for purification of the mature polypeptide fused to the marker in the case of a bacterial host, or, for example, the marker sequence can be a hemagglutinin (HA) tag when a mammalian host, e.g., COS-7 cells, is used. The HA tag corresponds to an epitope derived from the influenza hemagglutinin protein (Wilson, I. et al., Cell 37:767 (1984)).

The term "gene" means the segment of DNA involved in producing a polypeptide chain; it includes regions preceding and following the coding region (leader and trailer) as well as intervening sequences (introns) between individual coding segments (exons).

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

The term "isolated" means that the material is removed from its original environment (e.g., the natural environment if it is naturally occurring). For example, a naturally-occurring polynucleotides or polypeptides present in a living animal is not isolated, but the same polynucleotides or DNA or polypeptides, separated from some or all of the coexisting materials in the natural system, is isolated. Such polynucleotides could be part of a vector and/or such polynucleotides or polypeptides could be part of a composition, and still be isolated in that such vector or composition is not part of its natural environment. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising open reading frames (ORFs) of cDNA encoding deletion mutants Ckβ-7 polypeptide of the invention and DNA molecules which comprise a sequence substantially different from this sequence but which, due to the degeneracy of the genetic code, still encode a polypeptide of the invention. Of course, the genetic code is well known in the art. Thus, it would be routine for one skilled in the art to generate the degenerate variants described above.

The present invention further relates to polynucleotides which hybridize to the herein above-described sequences if there is at least 70%, preferably at least 90%, and more preferably at least 95% identity between the sequences. The present invention particularly relates to polynucleotides which hybridize under stringent conditions to the herein above-described polynucleotides. As herein used, the term "stringent conditions" means hybridization will occur only if there is at least 95% and preferably at least 97% identity between the sequences. The polynucleotides which hybridize to the herein above described polynucleotides in a preferred embodiment encode polypeptides which either retain substantially the same biological function or activity as the polypeptides.

Alternatively, the polynucleotide may have at least 20 bases, preferably 30 bases, and more preferably at least 50 bases which hybridize to a polynucleotide of the present invention and which has an identity thereto, as herein above described, and which may or may not retain activity. For example, such polynucleotides may be employed as probes for the polynucleotide of SEQ ID NO:1, for example, for recovery of the polynucleotide or as a diagnostic probe or as a PCR primer.

In another aspect, the invention provides an isolated nucleic acid molecule comprising a polynucleotide which hybridizes under stringent hybridization conditions to a portion of the polynucleotide in a nucleic acid molecule of the invention described above, for instance, the portions of the cDNA clone contained in ATCC Deposit 75675 which encode the polypeptides of the invention. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

Of course, polynucleotides hybridizing to a larger portion of the reference polynucleotide (e.g. the portions of the deposited cDNA clone which encode the polypeptides of the invention), for instance, a portion 50, 100, 150, 200 or 250 nt in length, or even to the entire length of the reference polynucleotide, are also useful as probes according to the present invention. By a portion of a polynucleotide of "at least 20 nt in length," for example, is intended 20 or more contiguous nucleotides from the nucleotide sequence of the reference polynucleotide. As indicated, such portions are useful diagnostically either as a probe according to conventional DNA hybridization techniques or as primers for amplification of a target sequence by the polymerase chain reaction (PCR), as described, for instance, in Molecular Cloning, A Laboratory Manual, 2nd. edition, Sambrook, J., Fritsch, E. F. and Maniatis, T., eds., Cold Spring Harbor Laboratory Press, Cold Spring Harbor, N.Y. (1989), the entire disclosure of which is hereby incorporated herein by reference.

Since a Ckβ-7 cDNA clone has been deposited and its determined nucleotide sequence provided, generating polynucleotides which hybridize to a portion of the Ckβ-7 cDNA molecule would be routine to the skilled artisan. For example, restriction endonuclease cleavage or shearing by sonication of a Ckβ-7 cDNA clone could easily be used to generate DNA portions of various sizes which are polynucleotides that hybridize, respectively, to a portion of the Ckβ-7 cDNA molecule.

Alternatively, the hybridizing polynucleotides of the present invention could be generated synthetically according to known techniques. Of course, a polynucleotide which hybridizes only to a poly A sequence (such as the 3' terminal poly(A) tract of a cDNA, or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g. practically any double-stranded cDNA clone).

Nucleic acid molecules of the present invention which encode a Ckβ-7 polypeptide of the invention may include, but are not limited to those encoding the amino acid sequence of the polypeptide, by itself; the coding sequence for the polypeptide and additional sequences, such as those encoding a heterologous leader or secretory sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz, et al., *Proc. Natl. Acad. Sci.* (*USA*) 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson, et al., *Cell* 37:767 (1984). As discussed below, other such fusion proteins include a Ckβ-7 polypeptide, fragment, or substitution variant fused to Fc at the N- or C-terminus.

The present invention further relates to variants of the nucleic acid molecules of the present invention, which encode portions, analogs or derivatives of a Ckβ-7 polypeptide. Variants may occur naturally, such as a natural allelic variant. By an "allelic variant" is intended one of several alternate forms of a gene occupying a given locus on a chromosome of an organism. Genes V, Lewin, B., ed., Oxford University Press, New York (1994). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the subject Ckβ-7 deletion mutant polypeptide. Also especially preferred in this regard are conservative substitutions. Most highly preferred are nucleic acid molecules encoding the specific Ckβ-7 deletion mutant polypeptides described above.

Variants of the Ckβ-7 deletion mutants of the invention will generally not have additional amino acids which are encoded by the nucleic acid molecule having the nucleotide sequence shown in FIG. 1 (SEQ ID NO:2) or encoded by the cDNA clone contained in ATCC Deposit No. 75675. Thus, when amino acids are added to either the N- and/or C-termini variants of the deletion mutants of the invention, in many instances, the amino acids added will not be encoded by the nucleic acid molecule having the nucleotide sequence shown in FIG. 1 (SEQ ID NO:2) or encoded by the cDNA clone contained in ATCC Deposit No. 75675. As a result, the present invention will generally not, for example, encompass nucleic acid molecules encoding amino acids 22 to 89 in SEQ ID NO:2 to which a nucleotide sequence encoding an alanine residue has been added to the 5' terminus.

The present invention is further directed to polynucleotides having at least a 70% identity, preferably at least 90% and more preferably at least a 95% identity to polynucleotides which encode the deletion mutants of the present invention, as well as fragments thereof, which fragments have at least 30 bases and preferably at least 50 bases and to polypeptides encoded by such polynucleotides.

Further embodiments of the invention include isolated nucleic acid molecules comprising a polynucleotide having a nucleotide sequence at least 90% identical, and more preferably at least 95%, 96%, 97%, 98% or 99% identical to the N- and C-terminal deletion mutants described herein.

By a polynucleotide having a nucleotide sequence at least, for example, 95% "identical" to a reference nucleotide sequence encoding a Ckβ-7 polypeptide is intended that the nucleotide sequence of the polynucleotide is identical to the reference sequence except that the polynucleotide sequence may include up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1, or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al., *Comp. App. Biosci.* 6:237–245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

Isolated nucleic acid molecules, particularly DNA molecules, are useful as probes for gene mapping, by in situ hybridization with chromosomes, and for detecting expression of a Ckβ-7 gene in human tissue, for instance, by Northern blot analysis. The present invention is further directed to fragments of the isolated nucleic acid molecules described herein. By a fragment of an isolated nucleic acid molecule having the nucleotide sequence of the deposited Ckβ-7 cDNA, or a nucleotide sequence shown in FIG. 1 (SEQ ID NO:1), is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, and 250 nt of the nucleotide sequence as shown in FIG. 1 (SEQ ID NO:1) also useful according to the present invention. By a fragment at least 20 nt in length, for example, is intended fragments which include 20 or more contiguous bases from the nucleotide sequence of the deposited cDNA or the nucleotide sequence as shown in FIG. 1 (SEQ ID NO:1).

Representative examples of Ckβ-7 polynucleotide fragments of the invention include, for example, fragments that comprise, or alternatively, consist of, a sequence from about nucleotide 1 to 50, 26 to 75, 63 to 100, 76 to 125, 101 to 150, 126 to 175, 151 to 200, 176 to 225, 201 to 250 and 226 to 270 of SEQ ID NO:1, or the complementary strand thereto, or the cDNA contained in the deposited clone. In this context "about" includes the particularly recited ranges, larger or smaller by several (5, 4, 3, 2, or 1) nucleotides, at either terminus or at both termini.

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

Polypeptides and Polypeptide Fragments

The present invention further relates to an isolated polypeptide which has the deduced amino acid sequence of one of the herein described deletion mutants of the Ckβ-7 polypeptide either shown in FIG. 1 (SEQ ID NO:2) or encoded by the cDNA of the clone deposited ATCC Deposit No. 75675. The terms "peptide" and "oligopeptide" are considered synonymous (as is commonly recognized) and each term can be used interchangeably as the context requires to indicate a chain of at least two amino acids coupled by peptidyl linkages. The word "polypeptide" is used herein for chains containing more than ten amino acid residues. All oligopeptide and polypeptide formulas or sequences herein are written from left to right and in the direction from amino terminus to carboxy terminus.

For many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. In the present case, since the Ckβ-7 is a member of the chemokine polypeptide family, deletions of N-terminal amino acids up to the first "Cys" required for formation of a disulfide bridge (Cys at position 30 in FIG. 1) may retain some biological activity such as receptor binding or modulation of target cell activities. Ckβ-7 polypeptides having further N-terminal deletions including the cysteine residue at position 30 in FIG. 1 (SEQ ID NO:2) would not be expected to retain such biological activities because it is known that this residue in a chemokine-related polypeptide is required for forming a disulfide bridge to provide structural stability which is needed for receptor binding and signal transduction.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the N-terminus. Whether a particular polypeptide lacking N-terminal residues of a complete protein retains such immunologic activities can readily be determined by routine methods described herein and otherwise known in the art.

Accordingly, the present invention further provides Ckβ-7 polypeptides having one or more residues deleted from the amino terminus of the amino acid sequence shown in SEQ ID NO:2, up to the cysteine residue at position number 30, and polynucleotides encoding such polypeptides. In particular, the present invention provides polypeptides comprising the amino acid sequence of residues n–89 of SEQ ID NO:2, where n is an integer in the range of 1 to 75, and preferably n is in the range of 15 to 30, where Cys-30 is the position of the first residue from the N-terminus the Ckβ-7 polypeptide (shown in SEQ ID NO:2) believed to be required for receptor binding activity.

More in particular, the invention provides polypeptides comprising the amino acid sequence shown in SEQ ID NO:2 as residues 1–89, 2–89, 3–89, 4–89, 5–89, 6–89, 7–89, 8–89, 9–89, 10–89, 11–89, 12–89, 13–89, 14–89, 15–89, 16≠89, 17–89, 18–89, 19–89, 20–89, 21–89, 22–89, 23–89, 24–89, 25–89, 26–89, 27–89, 28–89, 29–89, 30–89, 31–89, 32–89, 33–89, 34–89, 35–89, 36–89, 37–89, 38–89, 39–89, 40–89, 41–89, 42–89, 43–89, 44–89, 45–89, 46–89, 47–89, 48–89, 49–89, 50–89, 51–89, 52–89, 53–89, 54–89, 55–89, 56–89, 57–89, 58–89, 59–89, 60–89, 61–89, 62–89, 63–89, 64–89, 65–89, 66–89, 67–89, 68–89, 69–89, 70–89, 71–89, 72–89, 73–89, 74–89 or 75–89. Particularly preferred are polypeptides comprising the amino acid sequence shown in SEQ ID NO:2 as residues 15–89, 16–89, 17–89, 18–89, 19–89, 20–89, 21–89, 22–89, 23–89, 24–89, 25–89, 26–89, 27–89, 28–89, 29–89 or 30–89. Polynucleotides encoding the above-listed polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Dšbeli et al., *J. Biotechnology* 7:199–216 (1988). In the present case, since the Ckβ-7 protein is a member of the chemokine polypeptide family, deletions of C-terminal amino acids up to the cysteine at position 70 of SEQ ID NO:2 may retain some biological activity such as receptor binding or modulation of target cell activities. Polypeptides having further C-terminal deletions including the cysteine residue at position 70 of FIG. 1 (SEQ ID NO:2) would not be expected to retain such biological activities because it is known that this residue in a chemokine-related polypeptide is required for forming a disulfide bridge to provide structural stability which is needed for receptor binding and signal transduction.

However, even if deletion of one or more amino acids from the C-terminus of a protein results in modification or loss of one or more biological functions of the protein, other biological activities may still be retained. Thus, the ability of the shortened protein to induce and/or bind to antibodies which recognize the complete or mature form of the protein generally will be retained when less than the majority of the residues of the complete or mature protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues deleted from the carboxy terminus of the amino acid sequence of the Ckβ-7 polypeptide up to the cysteine residue at position 70 of SEQ ID NO:2, and polynucleotides encoding such polypeptides. In particular, the present invention provides polypeptides having the amino acid sequence of residues 1–m of the amino acid sequence in SEQ ID NO:2, where m is any integer in the range of 15 to 89, preferably the polypeptide comprises residues 20–m is in the range of 70–89 since residue cysteine-70 is the first residue from the C-terminus of the complete Ckβ-7 polypeptide (shown in SEQ ID NO:2) believed to be required for receptor binding and target cell modulation activities. Polynucleotides encoding these polypeptides also are provided.

More in particular, the invention provides polypeptides comprising the amino acid sequence shown in SEQ ID NO:2 as residues 1–15, 1–16, 1–17, 1–18, 1–19, 1–20, 1–21, 1–22, 1–23, 1–24, 1–25, 1–26, 1–27, 1–28, 1–29, 1–30, 1–31, 1–32, 1–33, 1–34, 1–35, 1–36, 1–37, 1–38, 1–39, 1–40, 1–41, 1–42, 1–43, 1–44, 1–45, 1–46, 1–47, 1–48, 1–49, 1–50, 1–51, 1–52, 1–53, 1–54, 1–55, 1–56, 1–57, 1–58, 1–59, 1–60, 1–61, 1–62, 1–63, 1–64, 1–65, 1–66, 1–67, 1–68, 1–69, 1–70, 1–71, 1–72, 1–73, 1–74, 1–75, 1–76, 1–77, 1–78, 1–79, 1–80, 1–81, 1–82, 1–83, 1–84, 1–85, 1–86, 1–87, 1–88, or 1–89. Particularly preferred are polypeptides comprising the amino acid sequence shown in SEQ ID NO:2 as residues 20–70, 20–71, 20–72, 20–73, 20–74, 20–75, 20–76, 20–77, 20–78, 20–79, 20–80, 20–81, 20–82, 20–83, 20–84, 20–85, 20–86, 20–87, 20–88 or 20–89. As already noted, polynucleotides encoding the above-listed polypeptides also are provided.

The invention also provides Ckβ-7 polypeptides having one or more amino acids deleted from both the amino and the carboxyl termini of the full-length polypeptide which may be described generally as having residues n–m of SEQ ID NO:2, where n and m are integers as described above. Particularly preferred Ckβ-7 polypeptides having N- and C-terminal deletions include the polypeptides comprising amino acid residues 21–89, 22–89, 23–89, 24–89, 25–89, 26–89, 27–89, 28–89, 29–89, 30–89, 21–88, 22–88, 23–88, 24–88, 25–88, 26–88, 27–88, 28–88, 29–88, 30–88, 21–87, 22–87, 23–87, 24–87, 25–87, 26–87, 27–87, 28–87, 29–87, 30–87, 21–86, 22–86, 23–86, 24–86, 25–86, 26–86, 27–86, 28–86, 29–86, 30–86, 21–85, 22–85, 23–85, 24–85, 25–85, 26–85, 27–85, 28–85, 29–85, 30–85, 21–84, 22–84, 23–84, 24–84, 25–84, 26–84, 27–84, 28–84, 29–84, 30–84, 21–83, 22–83, 23–83, 24–83, 25–83, 26–83, 27–83, 28–83, 29–83, 30–83, 21–82, 22–82, 23–82, 24–82, 25–82, 26–82, 27–82, 28–82, 29–82, 30–82, 21–81, 22–81, 23–81, 24–81, 25–81, 26–81, 27–81, 28–81, 29–81, 30–81, 21–80, 22–80, 23–80, 24–80, 25–80, 26–80, 27–80, 28–80, 29–80, 30–80, 21–79, 22–79, 23–79, 24–79, 25–79, 26–79, 27–79, 28–79, 29–79, 30–79, 21–78, 22–78, 23–78, 24–78, 25–78, 26–78, 27–78, 28–78, 29–78, 30–78, 21–77, 22–77, 23–77, 24–77, 25–77, 26–77, 27–77, 28–77, 29–77, 30–77, 21–76, 22–76, 23–76, 24–76, 25–76, 26–76, 27–76, 28–76, 29–76, 30–76, 21–75, 22–75, 23–75, 24–75, 25–75, 26–75, 27–75, 28–75, 29–75, 30–75, 21–74, 22–74, 23–74, 24–74, 25–74, 26–74, 27–74, 28–74, 29–74, 30–74, 21–73, 22–73, 23–73, 24–73, 25–73, 26–73, 27–73, 28–73, 29–73, 30–73, 21–72, 22–72, 23–72, 24–72, 25–72, 26–72, 27–72, 28–72, 29–72, 30–72, 21–71, 22–71, 23–71, 24–71, 25–71, 26–71, 27–71, 28–71, 29–71, 30–71, 21–70, 22–70, 23–70, 24–70, 25–70, 26–70, 27–70, 28–70, 29–70 or 30–70. Polynucleotides encoding the foregoing polypeptides are also provided.

Also preferred Ckβ-7 polypeptides having N- and C-terminal deletions include the polypeptides comprising amino acid residues 16–89, 17–89, 18–89, 19–89, 16–88, 17–88, 18–88, 19–88, 16–87, 17–87, 18–87, 19–87, 16–86, 17–86, 18–86, 19–86, 16–85, 17–85, 18–85, 19–85, 16–84, 17–84, 18–84, 19–84, 16–83, 17–83, 18–83, 19–83, 16–82, 17–82, 18–82, 19–82, 16–81, 17–81, 18–81, 19–81, 16–80, 17–80, 18–80, 19–80, 16–79, 17–79, 18–79, 19–79, 16–78, 17–78, 18–78, 19–78, 16–77, 17–77, 18–77, 19–77, 16–76, 17–76, 18–76, 19–76, 16–75, 17–75, 18–75, 19–75, 16–74, 17–74, 18–74, 19–74, 16–73, 17–73, 18–73, 19–73, 16–72, 17–72, 18–72, 19–72, 16–71, 17–71, 18–71, 19–71, 16–70, 17–70, 18–70 or 19–70.

Also included are portions of the complete Ckβ-7 amino acid sequence encoded by the cDNA clone contained in ATCC Deposit No. 75675, where this portion excludes from 1 to about 29 amino acids from the amino terminus of the complete polypeptide encoded by the human cDNA in the clone contained in ATCC Deposit No. 75675, or from 1 to about 19 amino acids from the carboxy terminus, or any combination of the above amino terminal and carboxy terminal deletions of the full-length polypeptide encoded by the human cDNA in the clone contained in ATCC Deposit No. 75675. Polynucleotides encoding all of the above deletion mutant polypeptide forms also are provided.

Most particularly preferred are any of the above-listed N- and C-terminal Ckβ-7 deletion mutants having an N-terminal methionine added to its amino terminus represented herein, for example, as Met-22–89.

Further included within the scope of the invention are additional Ckβ-7 deletion mutants which retain at least one biological activity of one of the deletion mutants described above. Also included are substitution mutants of these Ckβ-7 deletion mutants.

By "biological activity" is intended polypeptides exhibiting activity similar, but not necessarily identical, to one of the above described Ckβ-7 deletion mutants, as measured in a particular biological assay. Ckβ-7 deletion mutant activity can be measured by the assays set forth in Example 3.

Although the degree of activity need not be identical to that of the reference Ckβ-7 deletion mutant polypeptide, preferably, a polypeptide having Ckβ-7 deletion mutant activity will exhibit substantially similar activity as compared to a reference Ckβ-7 deletion mutant polypeptide (i.e., the candidate polypeptide will exhibit greater activity or not more than about twenty-fold less and, preferably, not more than about ten-fold less activity relative to the reference polypeptide).

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the full length polypeptide, such as an IgG Fc fusion region peptide or leader or secretory sequence or a sequence which is employed for purification of the Ckβ-7 polypeptide or a proprotein sequence. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include polypeptides which have at least 70% identity, more preferably at least 90% identity, and still more preferably at least 95% identity to the Ckβ-7 deletion mutants described above. Also included are polypeptides identical to portions of the Ckβ-7 deletion mutants described above containing at least 30 amino acids and more preferably at least 50 amino acids.

By a polypeptide having an amino acid sequence at least, for example, 95% "identical" to a reference amino acid sequence of a Ckβ-7 polypeptide is intended that the amino acid sequence of the polypeptide is identical to the reference sequence except that the polypeptide sequence may include up to five amino acid alterations per each 100 amino acids of the reference amino acid of a Ckβ-7 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in FIG. 1 (SEQ ID NO:2), the amino acid sequence encoded by the deposited cDNA clone, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al., *Comp. App. Biosci.* 6:237–245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence encoding the Ckβ-7 deletion mutants of the invention will encode a polypeptide a polypeptide having Ckβ-7 deletion mutant activity. In fact, since degenerate variants of these nucleotide sequences all encode the same polypeptide, this will be clear to the skilled artisan even without performing the above described comparison assay. As discussed below, it will be further recognized in the art that, for such nucleic acid molecules that are not degenerate variants, a reasonable number will also encode a polypeptide having Ckβ-7 deletion mutant activity.

As already noted, polypeptides of the invention may also include an initial modified methionine residue. In addition, MPIF-1 polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

Further, it will be recognized by those of skill in the art that in many cases it may be beneficial to add an N-terminal methionine to an N-terminally truncated Ckβ-7 polypeptide of the invention otherwise lacking an amino terminal methionine, for example, to achieve efficient expression by recombinant technology in bacterial such as *E. coli.*

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL5-receptor has been fused with Fc portions for the purpose of high-throughput screening assays to identify antagonists of hIL-5. See, Bennett, D., et al., *Journal of Molecular Recognition* 8:52–58 (1995) and Johanson, K., et al., *J. Biol. Chem.* 270(16):9459–9471 (1995).

The Ckβ-7 polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

It will be recognized in the art that some amino acid sequences of the Ckβ-7 polypeptides of the invention can be varied without significant affect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the Ckβ-7 polypeptides of the invention which show substantial Ckβ-7 deletion mutant activity. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Of additional special interest are also substitutions of charged amino acids with another charged amino acid or with neutral amino acids. This may result in proteins with improved characteristics such as less aggregation. Prevention of aggregation is highly desirable. Aggregation of proteins cannot only result in a reduced activity but be problematic when preparing pharmaceutical formulations because they can be immunogenic (Pinckard, et al., *Clin. Exp. Immunol.* 2:331–340 (1967), Robbins, et al., *Diabetes* 36:838–845 (1987), Cleland, et al., *Crit. Rev. Therapeutic Drug Carrier Systems* 10:307–377 (1993).

Replacement of amino acids can change the selectivity of the binding of a ligand to cell surface receptors. For example, Ostade et al., *Nature* 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)). n selective binding of TNF alpha to only one of the two known TNF receptors.

As indicated in detail above, further guidance concerning which amino acid changes are likely to be phenotypically silent (i.e., are not likely to have a significant deleterious effect on a function) can be found in Bowie, J. U., et al., "Deciphering the Message in Protein Sequences: Tolerance to Amino Acid Substitutions," *Science* 247:1306–1310 (1990) (see Table 1).

As indicated, changes are preferably of a minor nature, such as conservative amino acid substitutions that do not significantly affect the folding or activity of the protein (see Table 1).

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of substitutions for any given Ckβ-7 polypeptide of the invention will not be more than 50, 40, 30, 25, 20, 15, 10, 5 or 3. Thus, it will be appreciated by those of skill in the art that Ckβ-7 polypeptides of the invention can contain one or more of the above substitutions.

Recombinant DNA technology known to those skilled in the art can be used to create novel proteins. Muteins and deletions or fusion proteins can show, e.g., enhanced activity or increased stability. In addition, they could be purified in higher yields and show better solubility at least under certain purification and storage conditions. Set out below are additional examples of mutations that can be constructed.

Of special interest are chemically modified Ckβ-7 polypeptides. For example, Simmons et al. (*Science* 276: 276–279 (1997)) have shown that a modification of the amino terminus of the chemokine RANTES resulted in a protein that can occupy the CCR5 receptor site and block HIV-1 infection without causing signaling from the receptor. These modified chemokines are thought to avoid the unwanted side effects of signaling such as inflammation.

Preferred Ckβ-7 N-terminal modifications include the following:

| Name | Structure |
|---|---|
| AO-ethane | $CH_3—CH_2—O—NH_2$ |
| AO-1-propane | $CH_3—CH_2—CH_2—O—NH_2$ |
| AO-2-propane | $CH_3—(CH)CH_3—O—NH_2$ |
| AO-1-butane | $CH_3—CH_2—CH_2—CH_2—O—NH_2$ |
| AO-2-butane | $CH_3—CH_2—(CH)CH_3—O—NH_2$ |
| AO-pentane | $CH_3—CH_2—CH_2—CH_2—CH_2—O—NH_2$ |
| AO-5-pentene | $CH_2{=}CH_2—CH_2—CH_2—CH_2—O—NH_2$ |
| AO-2-pentene | $CH_3—CH_2—CH{=}CH—CH_2—O—NH_2$ |
| AO-hexane | $CH_3—CH_2—CH_2—CH_2—CH_2—CH_2—O—NH_2$ |
| AO-1-heptane | $CH_3—CH_2—CH_2—CH_2—CH_2—CH_2—CH_2—O—NH_2$ |
| AO-2-heptane | $CH_3—CH_2—CH_2—CH_2—CH_2—CH(CH_3)—O—NH_2$ |

Such N-terminal chemical modifications of the Ckβ-7 polypeptides described herein can be made according to the protocols described in *Science* 276:276–279 (1997), incorporated herein by reference in its entirety.

The polypeptides of the present invention are preferably provided in an isolated form, and preferably are substantially purified. A recombinantly produced version of the Ckβ-7 polypeptide can be substantially purified by the one-step method described in Smith and Johnson, *Gene* 67:31–40 (1988).

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting Ckβ-7 protein expression as described below or as agonists and antagonists capable of enhancing or inhibiting Ckβ-7 protein function. Further, such polypeptides can be used in the yeast two-hybrid system to "capture" Ckβ-7 protein binding proteins which are also candidate agonist and antagonist according to the present invention. The yeast two hybrid system is described in Fields and Song, *Nature* 340:245–246 (1989).

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen, et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, e.g., Sutcliffe, J. G. et al., *Science* 219:660–666 (1983).

Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Peptides that are extremely hydrophobic and those of six or fewer residues generally are ineffective at inducing antibodies that bind to the mimicked protein; longer, peptides, especially those containing proline residues, usually are effective. Sutcliffe et al., supra, at 661. For instance, 18 of 20 peptides designed according to these guidelines, containing 8–39 residues covering 75% of the sequence of the influenza virus hemagglutinin HA1 polypeptide chain, induced antibodies that reacted with the HA1 protein or intact virus; and 12/12 peptides from the MuLV polymerase and 18/18 from the rabies glycoprotein induced antibodies that precipitated the respective proteins.

Antigenic epitope-bearing peptides and polypeptides of the invention are therefore useful to raise antibodies, including monoclonal antibodies, that bind specifically to a polypeptide of the invention. Thus, a high proportion of hybridomas obtained by fusion of spleen cells from donors immunized with an antigen epitope-bearing peptide generally secrete antibody reactive with the native protein. Sutcliffe et al., supra, at 663. The antibodies raised by antigenic epitope-bearing peptides or polypeptides are useful to detect the mimicked protein, and antibodies to different peptides may be used for tracking the fate of various regions of a protein precursor which undergoes post-translational processing. The peptides and anti-peptide antibodies may be used in a variety of qualitative or quantitative assays for the mimicked protein, for instance in competition assays since it has been shown that even short peptides (e.g. about 9 amino acids) can bind and displace the larger peptides in immunoprecipitation assays. See, for instance, Wilson, et al., *Cell* 37:767–778 (1984) at 777. The anti-peptide antibodies of the invention also are useful for purification of the mimicked protein, for instance, by adsorption chromatography using methods well known in the art.

Antigenic epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); and sequences containing proline residues are particularly preferred.

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis. For instance, Houghten has described a simple method for synthesis of large numbers of peptides, such as 10–20 mg of 248 different 13 residue peptides representing single amino acid variants of a segment of the HA1 polypeptide which were prepared and characterized (by ELISA-type binding studies) in less than four weeks. Houghten, R. A., "General method for the rapid solid-phase synthesis of large numbers of peptides: specificity of antigen-antibody interaction at the level of individual amino acids," Proc. Natl. Acad. Sci. (USA) 82:5131–5135 (1985). This "Simultaneous Multiple Peptide Synthesis (SMPS)" process is further described in U.S. Pat. No. 4,631,211 to Houghten, et al. (1986). In this procedure the individual resins for the solid-phase synthesis of various peptides are contained in separate solvent-permeable packets, enabling the optimal use of the many identical repetitive steps involved in solid-phase methods. A completely manual procedure allows 500–1000 or more syntheses to be conducted simultaneously. Houghten et al., supra, at 5134.

Preferred nucleic acid fragments of the present invention include nucleic acid molecules encoding epitope-bearing portions of the Ckβ-7 polypeptide of the invention.

Epitope-bearing peptides and polypeptides of the invention are used to induce antibodies according to methods well known in the art. See, for instance, Sutcliffe, et al., supra; Wilson, et al., supra; Chow, M., et al., Proc. Natl. Acad. Sci. USA 82:910–914; and Bittle, F. J. et al., J. Gen. Virol. 66:2347–2354 (1985). Generally, animals may be immunized with free peptide; however, anti-peptide antibody titer may be boosted by coupling of the peptide to a macromolecular carrier, such as keyhole limpet hemacyanin (KLH) or tetanus toxoid. For instance, peptides containing cysteine may be coupled to carrier using a linker such as m-maleimidobenzoyl-N-hydroxysuccinimide ester (MBS), while other peptides may be coupled to carrier using a more general linking agent such as glutaraldehyde. Animals such as rabbits, rats and mice are immunized with either free or carrier-coupled peptides, for instance, by intraperitoneal and/or intradermal injection of emulsions containing about 100 μg peptide or carrier protein and Freund's adjuvant. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

Immunogenic epitope-bearing peptides of the invention, i.e., those parts of a protein that elicit an antibody response when the whole protein is the immunogen, are identified according to methods known in the art. For instance, Geysen et al., supra, discloses a procedure for rapid concurrent synthesis on solid supports of hundreds of peptides of sufficient purity to react in an enzyme-linked immunosorbent assay. Interaction of synthesized peptides with antibodies is then easily detected without removing them from the support. In this manner a peptide bearing an immunogenic epitope of a desired protein may be identified routinely by one of ordinary skill in the art. For instance, the immunologically important epitope in the coat protein of foot-and-mouth disease virus was located by Geysen et al. with a resolution of seven amino acids by synthesis of an overlapping set of all 208 possible hexapeptides covering the entire 213 amino acid sequence of the protein. Then, a complete replacement set of peptides in which all 20 amino acids were substituted in turn at every position within the epitope were synthesized, and the particular amino acids conferring specificity for the reaction with antibody were determined. Thus, peptide analogs of the epitope-bearing peptides of the invention can be made routinely by this method. U.S. Pat. No. 4,708,781 to Geysen (1987) further describes this method of identifying a peptide bearing an immunogenic epitope of a desired protein.

Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A., et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

The entire disclosure of each document cited in this section on "Polypeptides and Polypeptide Fragments" is hereby incorporated herein by reference.

As one of skill in the art will appreciate, Ckβ-7 polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g. for chimeric proteins, consisting of the first two domains of the human CD4-polypeptide and various domains of the constant regions of the heavy or light chains of mammalian immunoglobulins (EPA 394,827; Traunecker, et al., Nature 331:84–86 (1988)). Fusion proteins that have a disulfide-linked dimeric structure due to the IgG part can also be more efficient in binding and neutralizing other molecules than the monomeric Ckβ-7 deletion mutant polypeptide alone (Fountoulakis, et al., J. Biochem. 270: 3958–3964 (1995)).

Vectors and Host Cells

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The Ckβ7 polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

The DNA sequence in the expression vector is operatively linked to an appropriate expression control sequence(s) (promoter) to direct mRNA synthesis. As representative examples of such promoters, there may be mentioned: LTR or SV40 promoter, the E. coli lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as herein above described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

In addition to the use of expression vectors in the practice of the present invention, the present invention further includes novel expression vectors comprising operator and promoter elements operatively linked to nucleotide sequences encoding a protein of interest. One example of such a vector is pHE4a which is described in detail below.

Figures 3, 4:
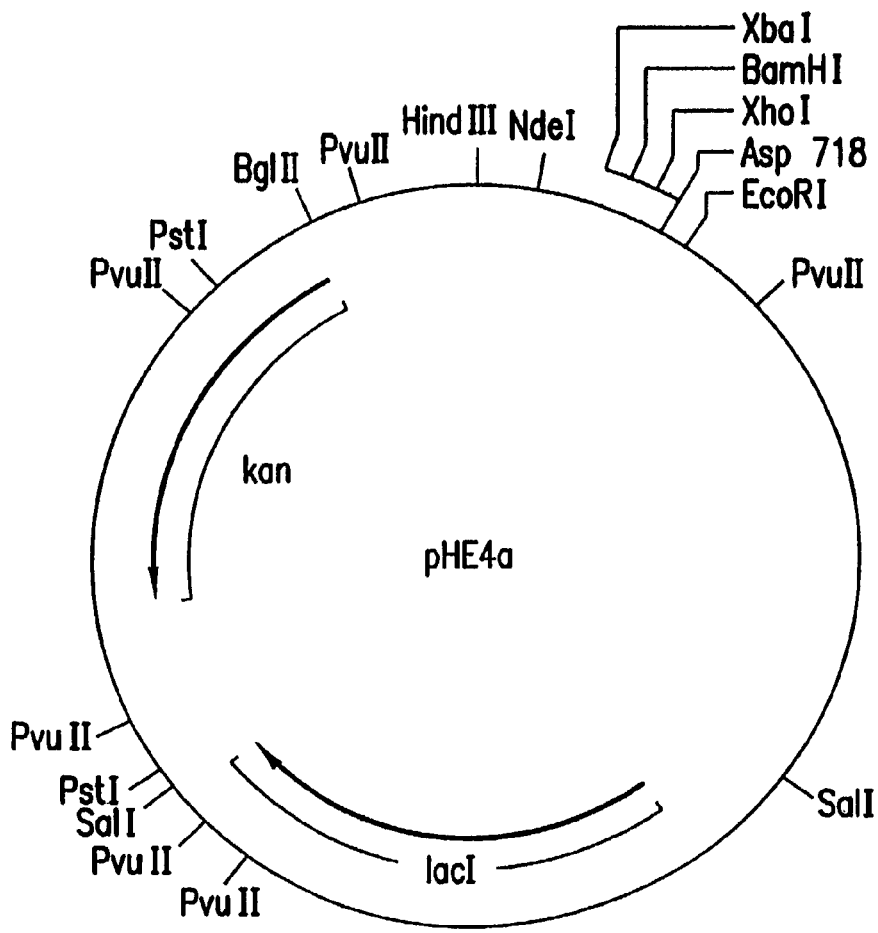
FIG. 3 shows a schematic representation of the pHE4a expression vector (SEQ ID NO:4). The locations of a number of restriction endonuclease cleavage sites, the kanamycin resistance marker gene, and the lacIq coding sequence are indicated.
FIG. 4 shows the nucleotide sequence of the regulatory elements of the pHE4a promoter (SEQ ID NO:5). The two lac operator sequences, the Shine-Delgarno sequence (S/D), and the terminal HindIII and NdeI restriction sites (italicized) are indicated.
Figure 5A:
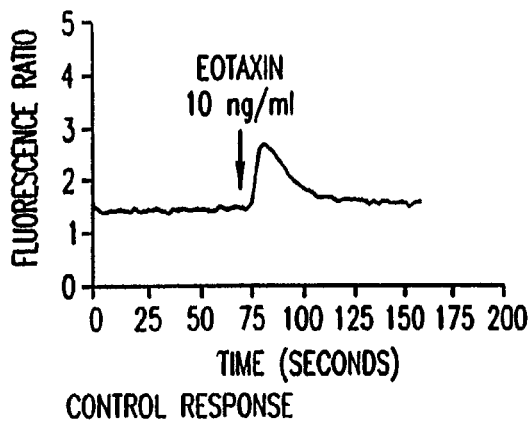
FIGS. 5A–5F show Eotaxin induced calcium fluxes in eosinophils at varying concentrations of Eotaxin in the presence (FIGS. 5C–5F) and absence (FIGS. 5A–5B) of Met-Ckβ-7*. The experimental results shown in FIGS. 5C–5F suggest that eosinophils become desensitized to an Eotaxin-induced calcium flux when Met-Ckβ-7* is administered either with (panels C and D) or prior to (panels E and F) Eotaxin stimulation. Further, the degree of cross-desensitization is dependent on the ratio of Ckβ-7 and Eotaxin used.
Figure 5B:
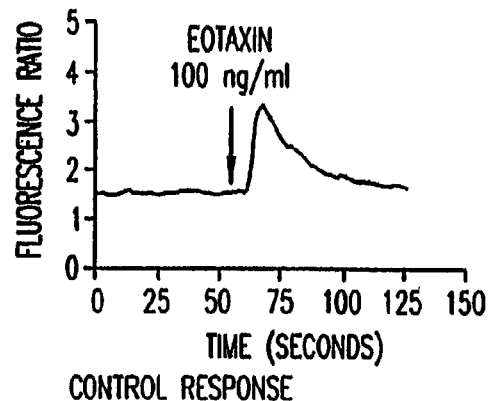
Figure 5C:
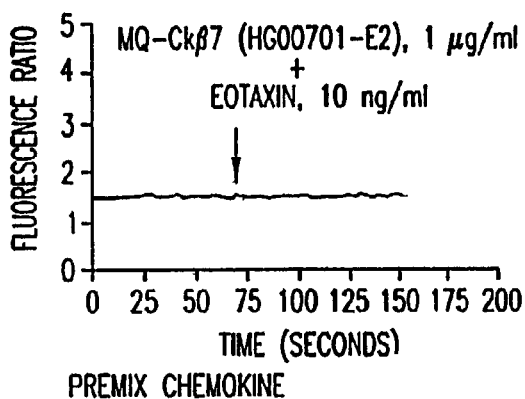
Figure 5D:
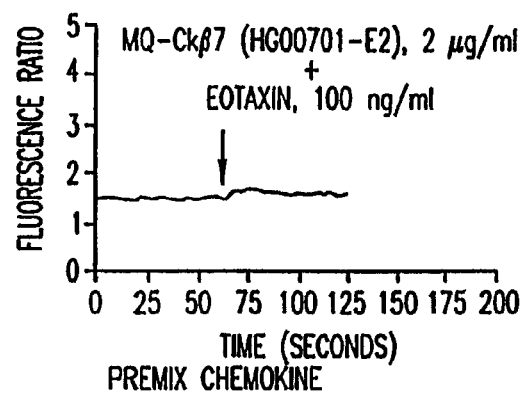
Figure 5E:
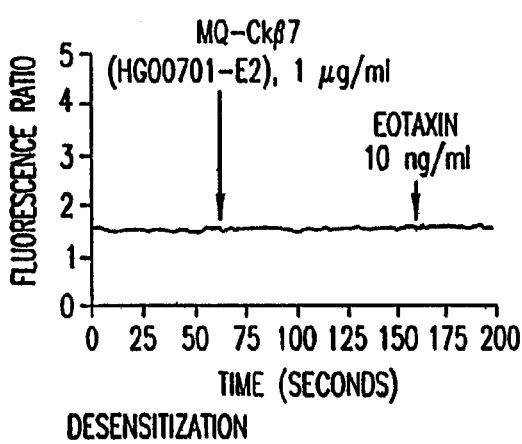
Figure 5F:
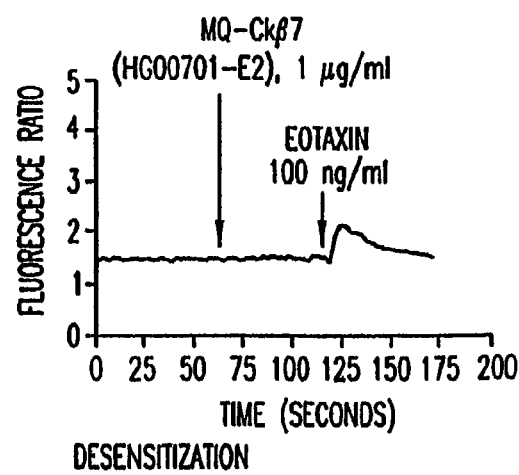
Figure 6A:
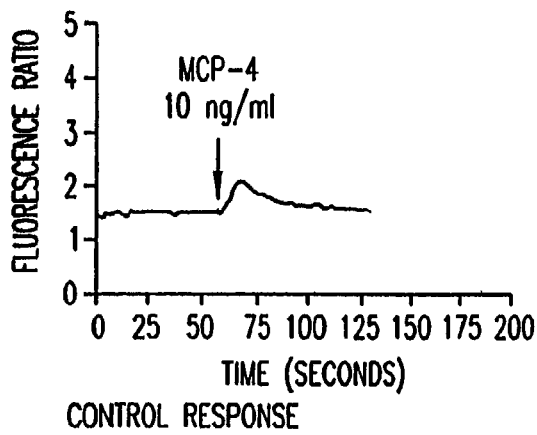
FIGS. 6A–6E show MCP-4 induced calcium fluxes in eosinophils at varying concentrations of MCP-4 and in the presence (FIGS. 6C–6E) and absence (FIGS. 6A–6B) of Met-Ckβ-7*. As above with Eotaxin, the experimental results shown in FIGS. 6C–6E suggest that eosinophils become desensitized to an MCP4 -indiced calcium flux when Met-Ckβ-7* is administered either with (panels C and D) or prior to (panel E) MCP-4.
Figure 6B:
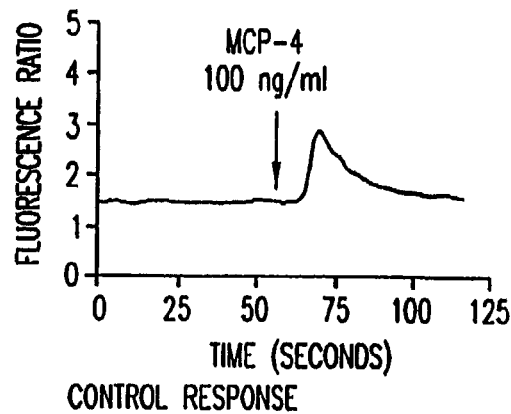
Figure 6C:
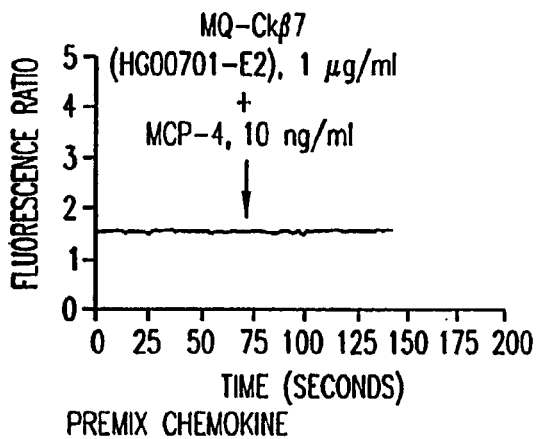
Figure 6D:
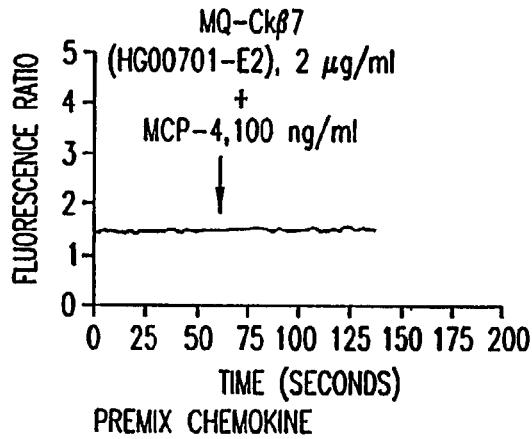
Figure 6E:
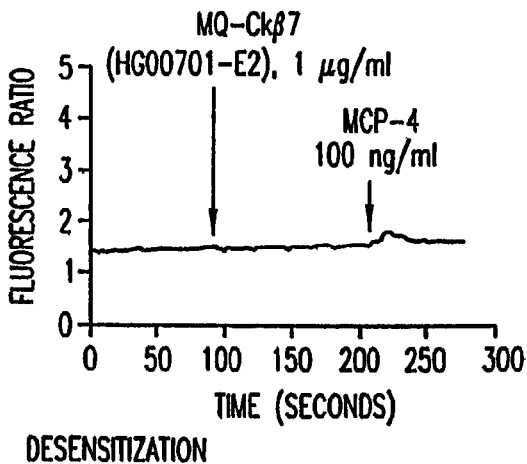
Figure 7A:
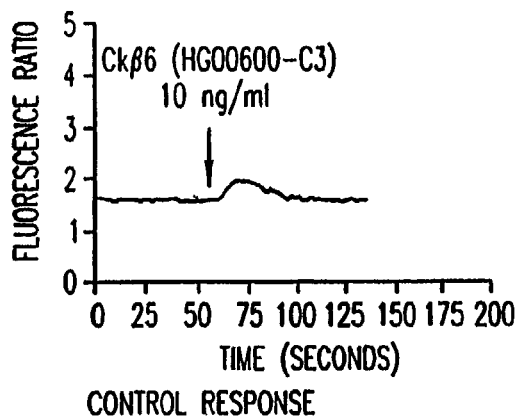
FIGS. 7A–7E show Ckβ-6 induced calcium fluxes in eosinophils at varying concentrations of Ckβ-6 and in the presence (FIGS. 7C–7E) and absence (FIGS. 7A–7B) of Met-Ckβ-7*. The results are similar to those seen in FIGS. 5 and 6 with Eotaxin and MCP-4.
Figure 7B:
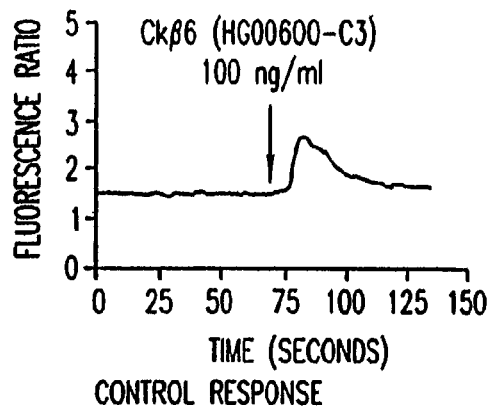
Figure 7C:
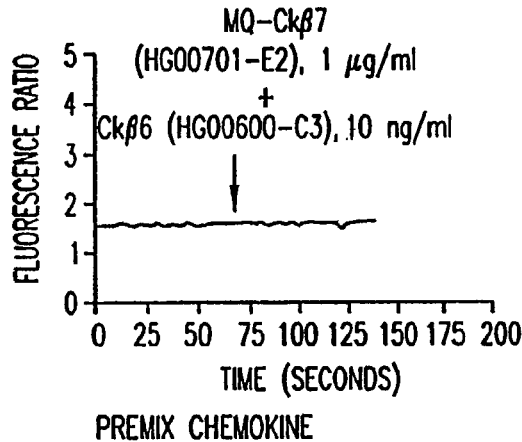
Figure 7D:
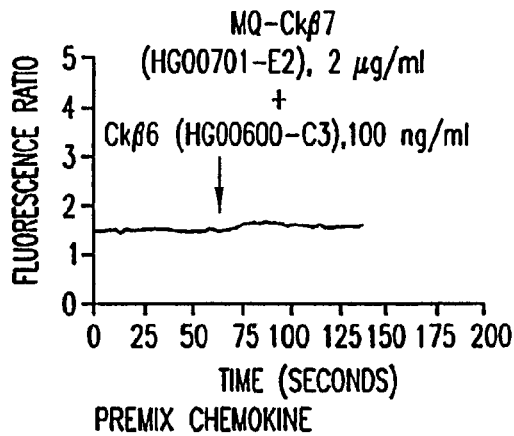
Figure 7E:
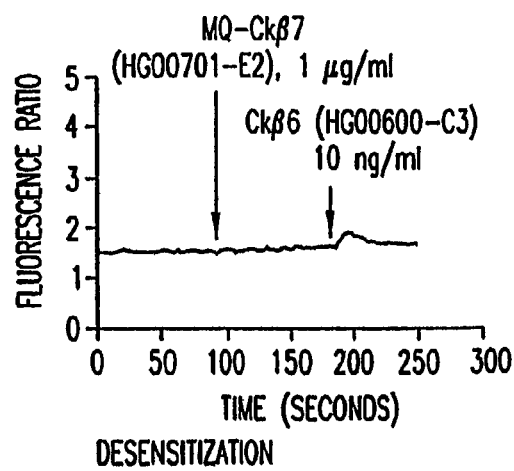
Figure 8:
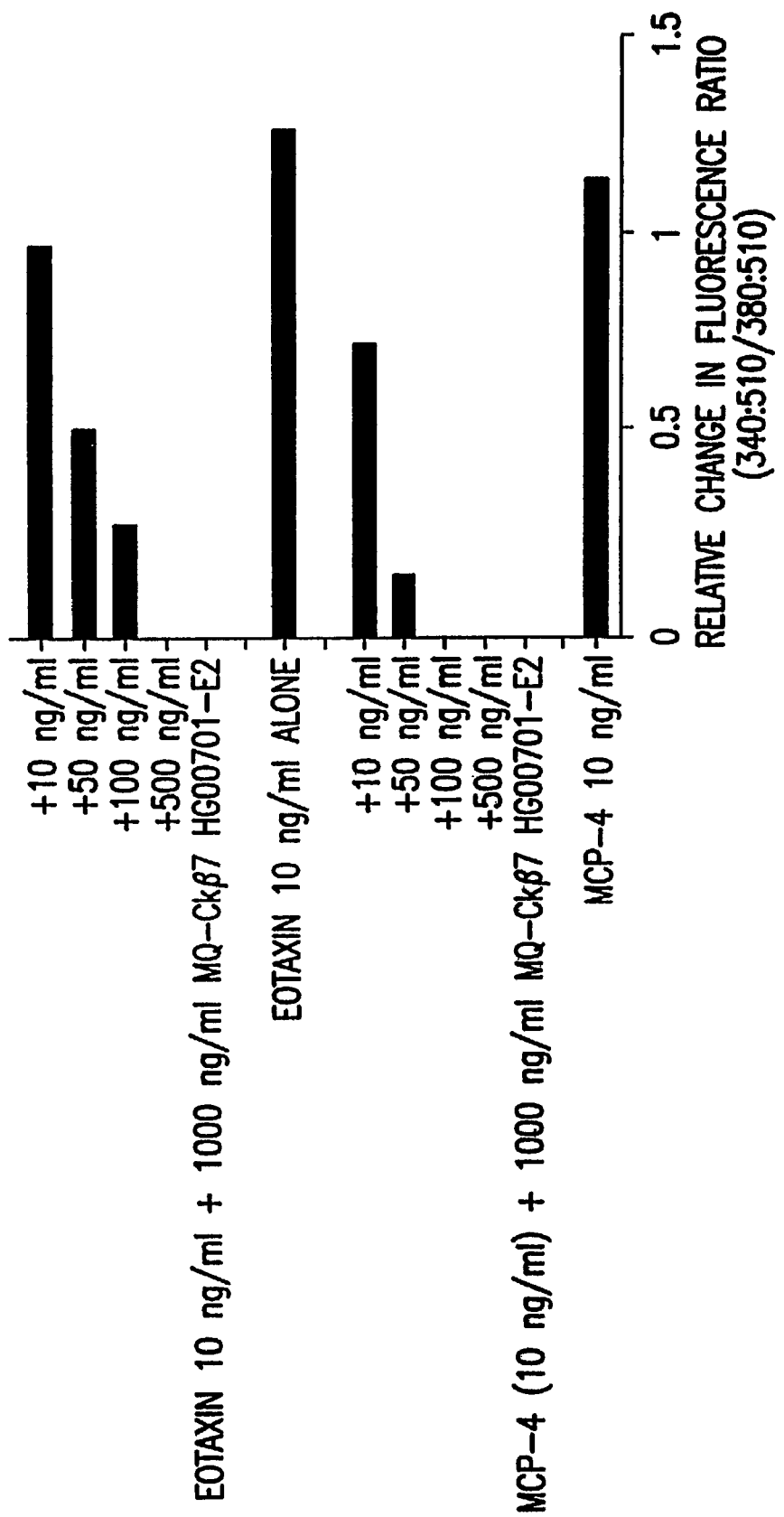
FIG. 8 shows dose-response profiles of Met-Ckβ-7* inhibition of Eotaxin and MCP-4 (CCR3 agonists) induced calcium flux in eosinophils. These data demonstrate that increased concentrations of Met-Ckβ-7* lead to increased inhibition of Eotaxin and MCP-4 induced calcium flux in eosinophils. Further, with both Eotaxin and MCP-4, high concentrations of Met-Ckβ-7* result in complete inhibition of calcium flux.

As summarized in FIG. 7 and FIG. 8, components of the pHE4a vector (SEQ ID NO:4) include: 1) a neomycinphosphotransferase gene as a selection marker, 2) an E. coli origin of replication, 3) a T5 phage promoter sequence, 4) two lac operator sequences, 5) a Shine-Delgarno sequence, 6) the lactose operon repressor gene (lacIq) and 7) a multiple cloning site linker region. The origin of replication (oriC) is derived from pUC19 (LTI, Gaithersburg, Md.). The promoter sequence and operator sequences were made synthetically. Synthetic production of nucleic acid sequences is well known in the art. CLONTECH 95/96 Catalog, pages 215–216, CLONTECH, 1020 East Meadow Circle, Palo Alto, Calif. 94303. The pHE4a vector was deposited with the ATCC on Feb. 25, 1998, and given accession number 209645.

A nucleotide sequence encoding Ckβ-7 is operatively linked to the promoter and operator of pHE4a by restricting the vector with NdeI and either XbaI, BamHI, XhoI, or Asp718, and isolating the larger fragment (the multiple cloning site region is about 310 nucleotides) on a gel. The nucleotide sequence encoding the desired Ckβ-7 having the appropriate restriction sites is generated, for example, according to the PCR protocol described in Example 1, using PCR primers having restriction sites for NdeI (as the 5' primer) and either XbaI, BamHI, XhoI, or Asp718 (as the 3' primer). The PCR insert is gel purified and restricted with compatible enzymes. The insert and vector are ligated according to standard protocols.

As noted above, the pHE4a vector contains a lacIq gene. LacIq is an allele of the lacI gene which confers tight regulation of the lac operator. Amann, E. et al., *Gene* 69:301–315 (1988); Stark, M., *Gene* 51:255–267 (1987). The lacIq gene encodes a repressor protein which binds to lac operator sequences and blocks transcription of down-stream (i.e., 3') sequences. However, the lacIq gene product dissociates from the lac operator in the presence of either lactose or certain lactose analogs, e.g., isopropyl B-D-thiogalactopyranoside (IPTG). The Ckβ-7 protein thus is not produced in appreciable quantities in uninduced host cells containing the pHE4a vector. Induction of these host cells by the addition of an agent such as IPTG, however, results in the expression of the Ckβ-7 coding sequence.

The promoter/operator sequences of the pHE4a vector (SEQ ID NO:5) comprise a T5 phage promoter and two lac operator sequences. One operator is located 5' to the transcriptional start site and the other is located 3' to the same site. These operators, when present in combination with the lacIq gene product, confer tight repression of down-stream sequences in the absence of a lac operon inducer, e.g., IPTG. Expression of operatively linked sequences located downstream from the lac operators may be induced by the addition of a lac operon inducer, such as IPTG. Binding of a lac inducer to the lacIq proteins results in their release from the lac operator sequences and the initiation of transcription of operatively linked sequences. Lac operon regulation of gene expression is reviewed in Devlin, T., TEXTBOOK OF BIOCHEMISTRY WITH CLINICAL CORRELATIONS, 4th Edition (1997), pages 802–807.

The pHE4 series of vectors contain all of the components of the pHE4a vector except for the Ckβ-7 coding sequence. Features of the pHE4a vectors include optimized synthetic T5 phage promoter, lac operator, and Shine-Delgarno sequences. Further, these sequences are also optimally spaced so that expression of an inserted gene may be tightly regulated and high level of expression occurs upon induction.

Among known bacterial promoters suitable for use in the production of proteins of the present invention include the *E. coli* lacI and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous Sarcoma Virus (RSV), and metallothionein promoters, such as the mouse metallothionein-I promoter.

The pHE4a vector also contains a Shine-Delgarno sequence 5' to the AUG initiation codon. Shine-Delgarno sequences are short sequences generally located about 10 nucleotides up-stream (i.e., 5') from the AUG initiation codon. These sequences essentially direct prokaryotic ribosomes to the AUG initiation codon.

Thus, the present invention is also directed to expression vector useful for the production of the proteins of the present invention. This aspect of the invention is exemplified by the pHE4a vector (SEQ ID NO:4).

In addition, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223–3, pKK233–3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., et al., *Basic Methods in Molecular Biology* (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual,* Second Edition, Cold Spring Harbor, N.Y. (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces,* and *Staphylococcus,* although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., *Basic Methods In Molecular Biology* (1986). It is specifically contemplated that Ckβ7 polypeptides may in fact be expressed by a host cell lacking a recombinant vector.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

Polypeptide Purification and Isolation

The polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps. A specific method for purifying Ckβ-7 polypeptides expressed in E. coli is described in Example 1, infra.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The polypeptides of the present invention can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the Ckβ7 polypeptides may be glycosylated or may be non-glycosylated. In addition, Ckβ7 polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., Ckβ7 coding sequence), and/or to include genetic material (e.g., heterologous polynucleotide sequences) that is operably associated with Ckβ7 polynucleotides of the invention, and which activates, alters, and/or amplifies endogenous Ckβ7 polynucleotides. For example, techniques known in the art may be used to operably associate heterologous control regions (e.g., promoter and/or enhancer) and endogenous Ckβ7 polynucleotide sequences via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983 , Proteins: Structures and Molecular Principles, W. H. Freeman & Co., N.Y., and Hunkapiller et al., Nature 310:105–111 (1984)). For example, a polypeptide corresponding to a fragment of a Ckβ7 polypeptide can be synthesized by use of a peptide synthesizer. Furthermore, if desired, nonclassical amino acids or chemical amino acid analogs can be introduced as a substitution or addition into the Ckβ7 polypeptide sequence. Non-classical amino acids include, but are not limited to, the D-isomers of the common amino acids, 2,4-diaminobutyric acid, a-amino isobutyric acid, 4-aminobutyric acid, Abu, 2-amino butyric acid, gAbu, eAhx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses Ckβ7 polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to GCSF), see also Malik et al., *Exp. Hematol.* 20:10281035 (1992) (reporting pegylation of GMCSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

The Ckβ7 polypeptides of the invention may be in monomers or multimers (i.e., dimers, trimers, tetramers and higher multimers). Accordingly, the present invention relates to monomers and multimers of the Ckβ7 polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 or encoded by the cDNA contained in the deposited clone (including fragments, variants, splice variants, and fusion proteins, corresponding to these as described herein). These homomers may contain Ckβ7 polypeptides having identical or different amino acid sequences. In a specific embodiment, a homomer of the invention is a multimer containing only Ckβ7 polypeptides having an identical amino acid sequence. In another specific embodiment, a homomer of the invention is a multimer containing Ckβ7 polypeptides having different amino acid sequences. In specific embodiments, the multimer of the invention is a homodimer (e.g., containing Ckβ7 polypeptides having identical or different amino acid sequences) or a homotrimer (e.g., containing Ckβ7 polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the Ckβ7 polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the Ckβ7 polypeptides of the invention. Such covalent associations may involve one or more amino acid residues contained in the polypeptide sequence (e.g., that recited in SEQ ID NO:2, or contained in the polypeptide encoded by the clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a Ckβ7 fusion protein. In one example, covalent associations are between the heterologous sequence contained in a fusion protein of the invention (see, e.g., U.S. Pat. No. 5,478,925). In a specific example, the covalent associations are between the heterologous sequence contained in a Ckβ7-Fc fusion protein of the invention (as described herein). In another specific example, covalent associations of fusion proteins of the invention are between heterologous polypeptide sequence from another protein that is capable of forming covalently associated multimers, such as for example, oseteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide seuqence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hyrophobic or signal peptide) and which can be incorporated by membrane reconstitution techniques into liposomes (see, e.g., U.S. Pat. No. 5,478,925, which is herein incorporated by reference in its entirety).

As described above, the polypeptides of the present invention may be chemically modified such as by addition of AOP- or N-nonanoyl-(NNY) to the amino terminus. Such analogs or derivative may be produced by combined recombinant and chemical means (Simmons, G. et al., Science 276:276 (1997), or by total chemical synthesis (Hoover, J. et al. Chem. Biol. 6:43 (1999); Mosier, D. E. et al. J. Virol. 73:3544 (1999)).

Therapeutics

The polypeptide of the present invention can be used in a variety of immunoregulatory and inflammatory functions and also in the treatment of a number of disease conditions.

Allergic reactions are characterized by the infiltration of tissues by activated eosinophils, Th2 lymphocytes and basophils. The β-chemokine receptor CCR3, which recognizes the ligands eotaxin, eotaxin-2, MCP3, MCP4 and RANTES, plays a central role in this process, and antagonists to this receptor could have potential therapeutic use in the treatment of allergy. The present inventors have discovered that Met-Ckβ7 is a potent and specific CCR3 antagonist that prevents signaling through this receptor. At concentrations as low as 1 nM, Met-Ckβ7 can block eosinophil chemotaxis induced by the most potent CCR3 ligands. Moreover, Met-Ckβ7 is a more potent CCR3 antagonist than Met- and AOP-RANTES, and unlike these proteins, it exhibits no partial agonist activity and is highly specific for CCR3. Thus, this antagonist is useful in ameliorating leukocyte infiltration associated with allergic inflammation. Met- Ckβ7, is a modified form of the β-chemokine MIP4 (alternatively called PARC, AMAC1 or DCCK1). Surprisingly, the unmodified MIP4 protein, which is known to act as a T-cell chemoattractant, also exhibits this CCR3 antagonistic activity, albeit to a lesser extent than Met-Ckβ7, but to a level that is of physiological relevance. MIP4 therefore uses chemokine receptor agonism and antagonism to control leukocyte movement in vivo. The enhanced activity of Met-Ckβ7 is due to the alteration of the extreme N-terminal residue from an alanine to a methionine (see Example 4 and FIGS. 21–33).

Figure 9:
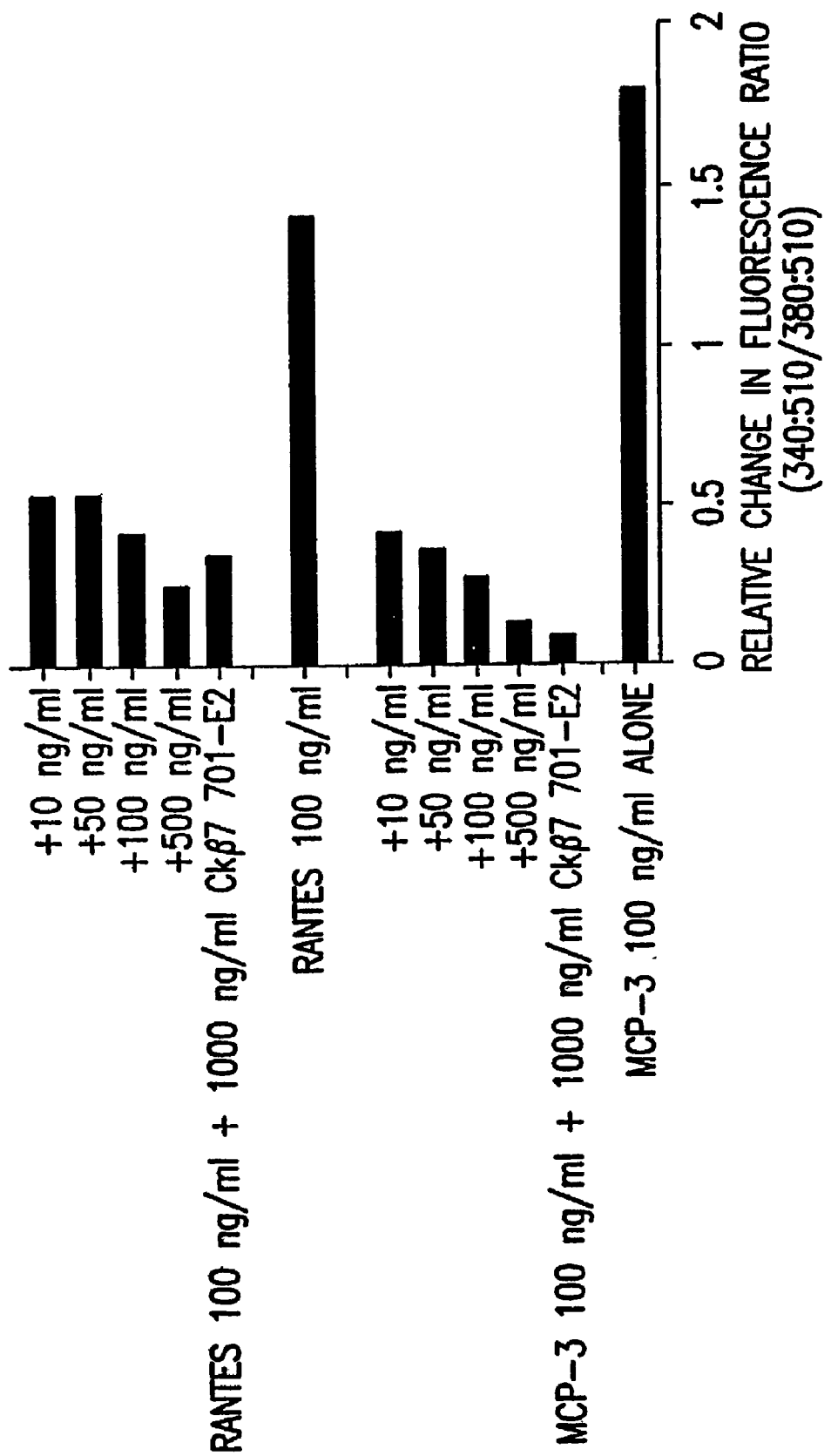
FIG. 9 shows dose-response profiles of Met-Ckβ-7* inhibition of RANTES and MCP-3 (CCR3 agonists) induced calcium flux in eosinophils. These data demonstrate that increased concentrations of Met-Ckβ-7* lead to increased inhibition of RANTES and MCP-3 induced calcium flux in eosinophils. However, with both RANTES and MCP-3, relatively high concentrations of Met-Ckβ-7* do not result in complete inhibition of calcium flux. These data are in agreement with known receptor specificity of RANTES and MCP3, which on some donor eosinophils includes CCR1.
Figure 10A:
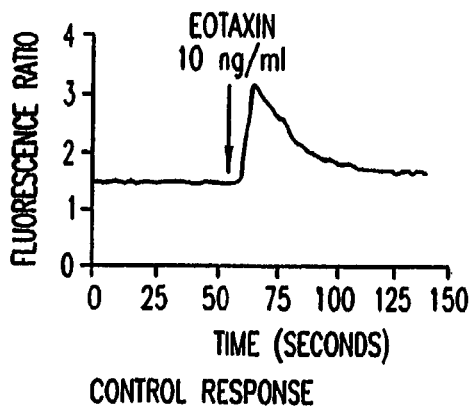
FIGS. 10A–10B show the results of calcium mobilization assays in the presence of Eotaxin and compositions comprising mixtures of several different Ckβ-7 deletion variants.
Figure 10B:
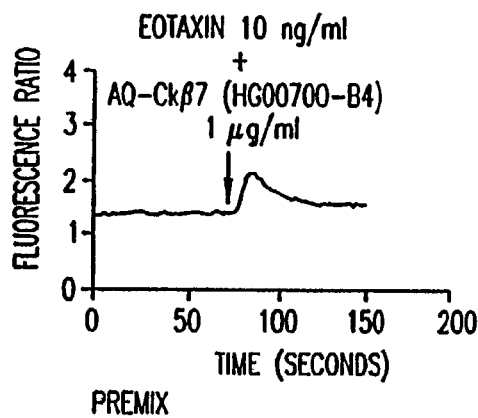
Figure 10C:
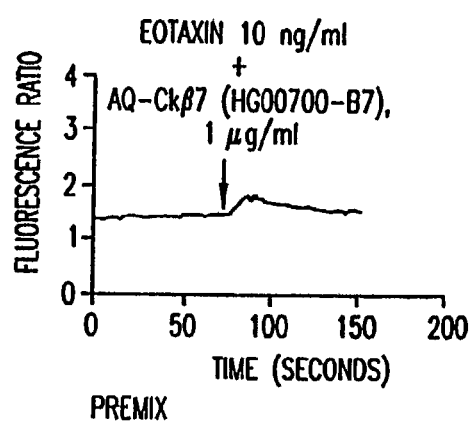
FIG. 10C shows calcium flux in eosinophils in the presence of 10 ng/ml Eotaxin and 1 μg/ml Ckβ-7 (85% in the form of a Ckβ-7 fragment having amino acids 21–89 in SEQ ID NO:2 and 10% having amino acids 26–89 in SEQ ID NO:2).
Figure 10D:
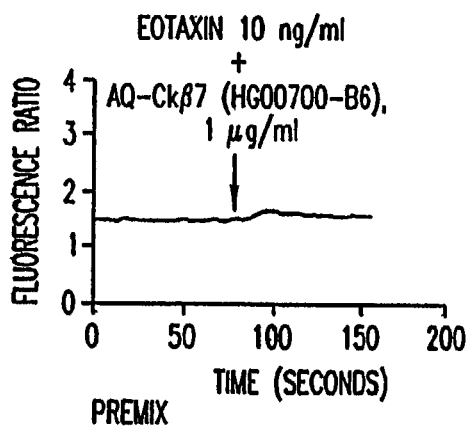
FIG. 10D shows calcium flux in eosinophils in the presence of 10 ng/ml Eotaxin and 1 μg/ml Ckβ-7 (80% in the form of a Ckβ-7 fragment having amino acids 21–89 in SEQ ID NO:2 and 15% having amino acids 26–89 in SEQ ID NO:2).
Figure 10E:
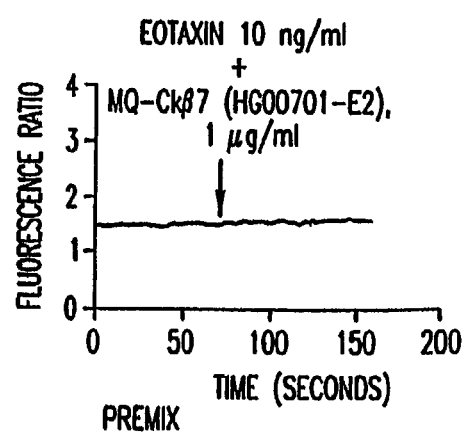
FIG. 10E shows calcium flux in eosinophils in the presence of 10 ng/ml Eotaxin and 1 μg/ml Ckβ-7 (95% in the form of a Ckβ-7 fragment having amino acids 22–89 in SEQ ID NO:2 and a methionine residue at the N-terminus (Met-22–89) and 2% having amino acids 26–89 in SEQ ID NO:2). The Ckβ-7 composition used in FIG. 10E had the highest activity, followed by the compositions used in FIGS. 10D, 10C and 10B. (Data was obtained using eosinophils from a single donor.)
Figure 11A:
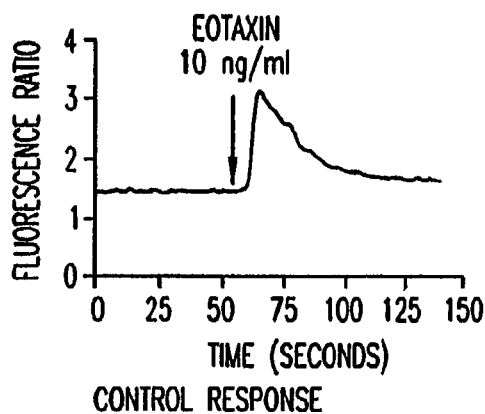
FIGS. 11A–11D show cross-desensitization of eosinophil calcium flux signal in the presence of mixtures of various Ckβ-7 deletion variants. A Ckβ-7 composition comprising a Ckβ-7 mixture in which 40% is in the form of a Ckβ-7 fragment having amino acids 21–89 in SEQ ID NO:2 and 60% is in the form of a Ckβ-7 fragment having amino acids 25–89 in SEQ ID NO:2 was used in FIG. 11B. A Ckβ-7 composition comprising a Ckβ-7 mixture in which 80% is in the form of a Ckβ-7 fragment having amino acids 21–89 in SEQ ID NO:2 and 15% is in the form of a Ckβ-7 fragment having amino acids 26–89 in SEQ ID NO:2 was used in FIG. 11C. A Ckβ-7 composition comprising a Ckβ-7 mixture in which 85% is in the form of a Ckβ-7 fragment having amino acids 21–89 in SEQ ID NO:2 and 10% is in the form of a Ckβ-7 fragment having amino acids 26–89 in SEQ ID NO:2 was used in FIG. 11D.
Figure 11B:
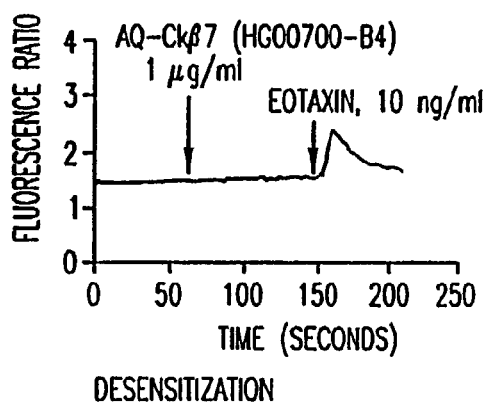
Figure 11C:
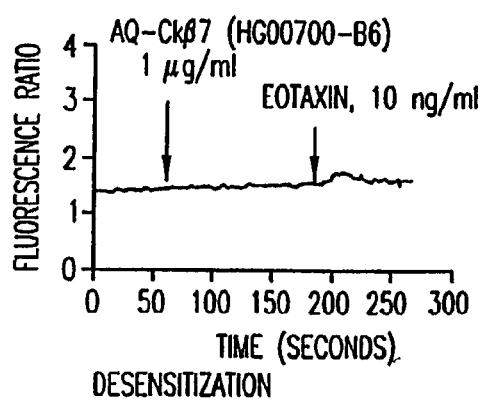
Figure 11D:
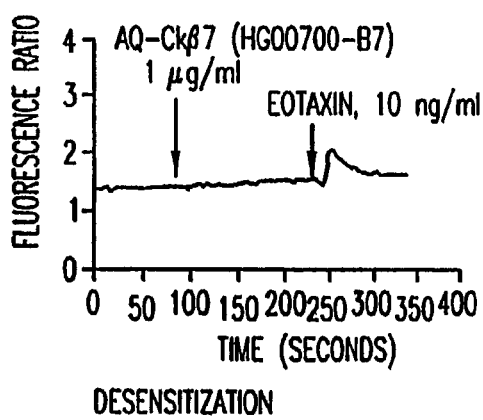
Figure 12A:
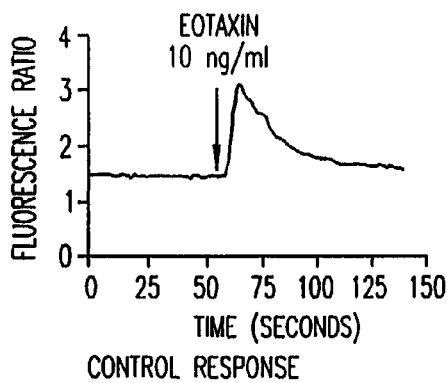
FIGS. 12A–12E show the effect of various concentrations of various Ckβ-7 deletion variants on Eotaxin induced calcium flux in eosinophils. Ckβ-7 composition comprising a Ckβ-7 mixture in which 80% is in the form of a Ckβ-7 fragment having amino acids 21–89 in SEQ ID NO:2 and 15% is in the form of a Ckβ-7 fragment having amino acids 26–89 in SEQ ID NO:2 was used in FIGS. 12B and 12C. A Ckβ-7 composition comprising a Ckβ-7 mixture in which 85% is in the form of a Ckβ-7 fragment having amino acids 21–89 in SEQ ID NO:2 and 10% is in the form of a Ckβ-7 fragment having amino acids 26–89 in SEQ ID NO:2 was used in FIGS. 12D and 12E. Ckβ-7 concentrations of 100 ng/ml were used in FIGS. 12C and 12E. Ckβ-7 concentrations of 1 μg/ml were used in FIGS. 12B and 12D.
Figure 12B:
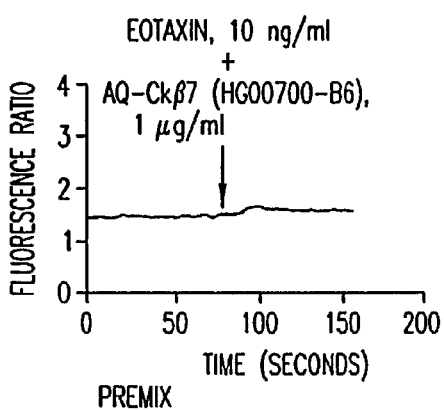
Figure 12C:
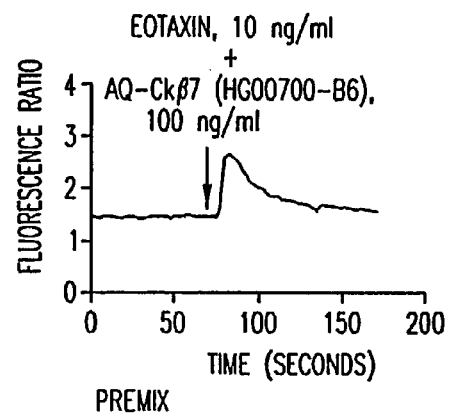
Figure 12D:
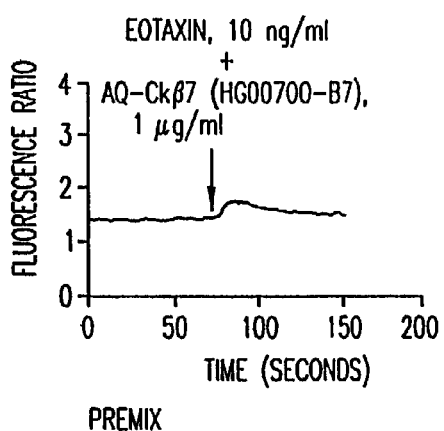
Figure 12E:
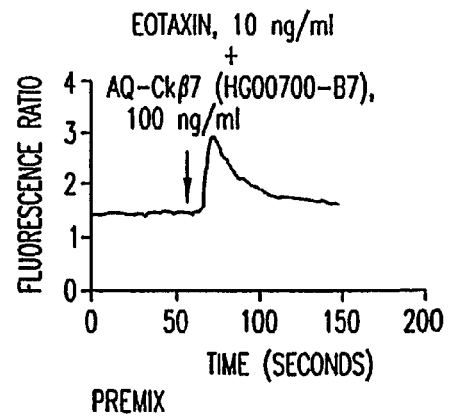
Figure 13:
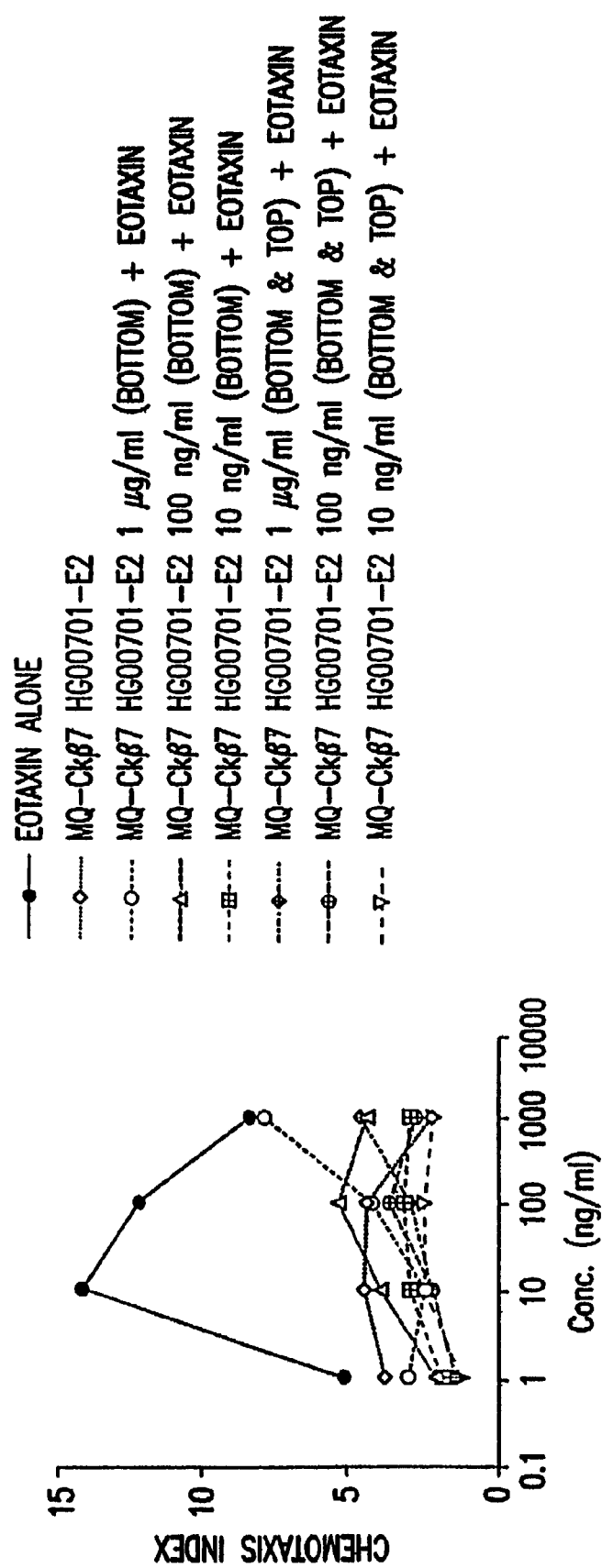
FIG. 13 shows Met-Ckβ-7* inhibition of Eotaxin induced eosinophil chemotaxis using eosinophils obtained from a single donor (Donor 1). Eosinophil chemotaxis was measured in the presence of Eotaxin alone, Met-Ckβ-7* alone, and Eotaxin with varying concentrations of Met-Ckβ-7*. Further, Met-Ckβ-7* was placed in varying concentrations is either the bottom well of the chemotactic chamber or both the bottom and top wells.
Figure 14:
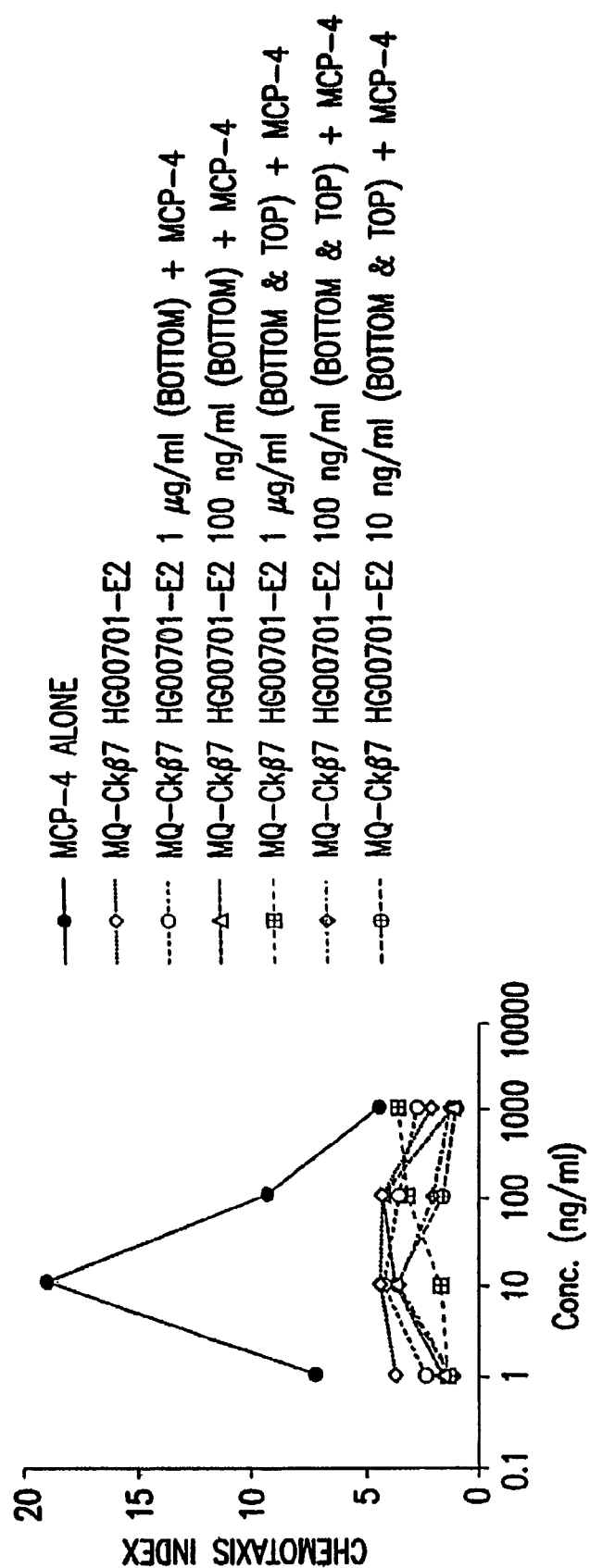
FIG. 14 shows Met-Ckβ-7* inhibition of MCP-4 induced eosinophil chemotaxis using eosinophils obtained from a single donor (Donor 1). Eosinophil chemotaxis was measured in the presence of MCP-4 alone, Met-Ckβ-7* alone, and MCP-4 with varying concentrations of Met-Ckβ-7*. Further, Met-Ckβ-7* was placed in varying concentrations is either the bottom well of the chemotactic chamber or both the bottom and top wells.
Figure 15:
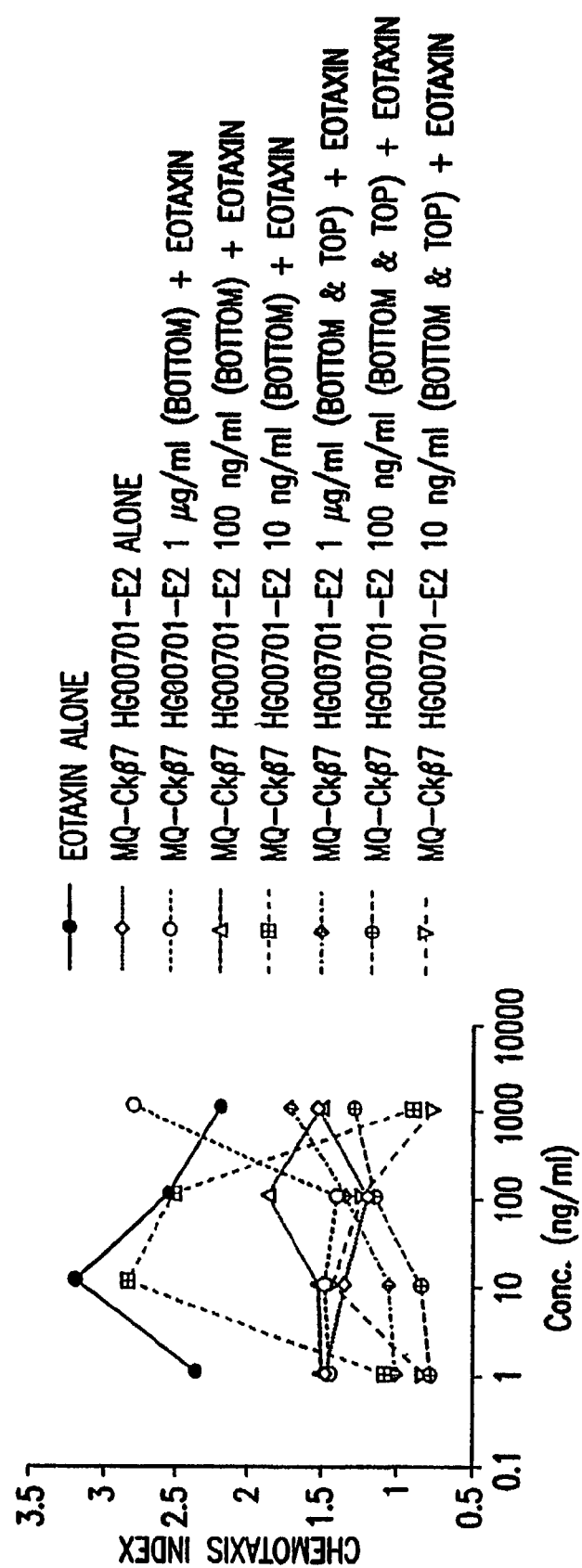
FIG. 15 shows Met-Ckβ-7* inhibition of Eotaxin induced eosinophil chemotaxis using eosinophils obtained from a single donor (Donor 2). Eosinophil chemotaxis was measured as described in FIG. 13.
Figure 16:
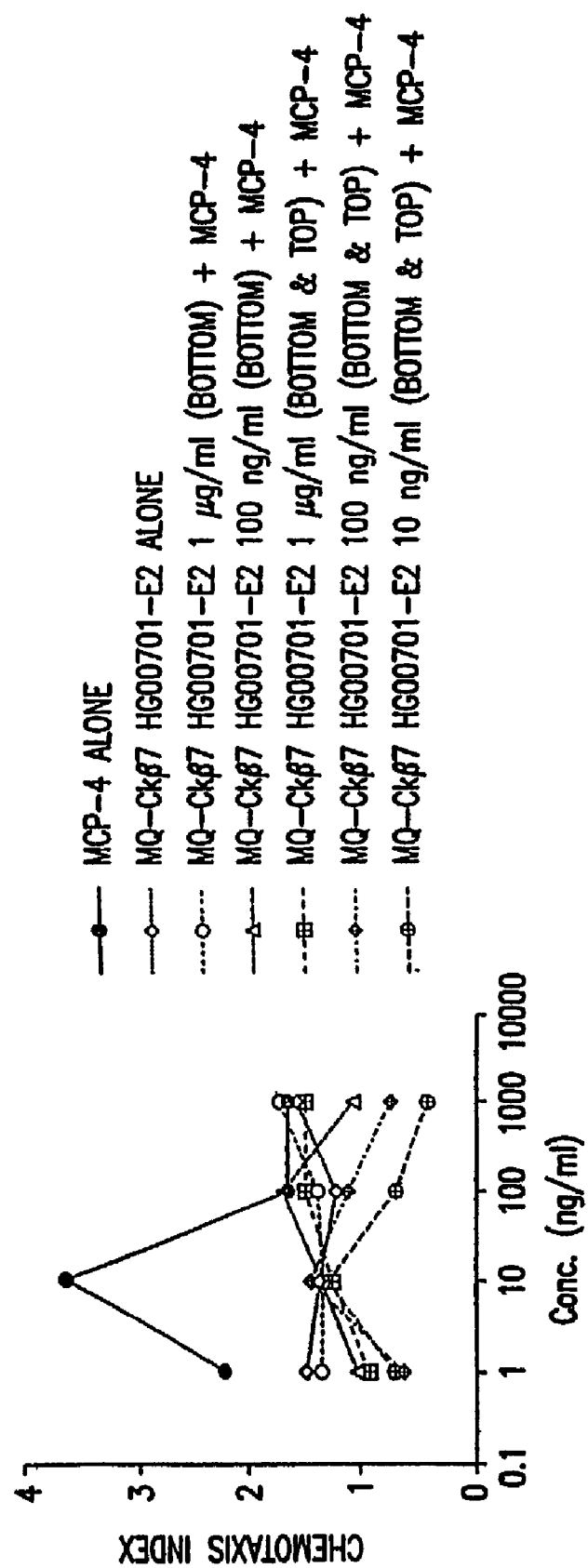
FIG. 16 shows Met-Ckβ-7* inhibition of MCP-4 induced eosinophil chemotaxis using eosinophils obtained from a single donor (Donor 2). Eosinophil chemotaxis was measured as described in FIG. 14.
Figure 17:
FIG. 17 shows Met-Ckβ-7* inhibition of Eotaxin induced eosinophil chemotaxis using eosinophils obtained from a single donor (Donor 3). Eosinophil chemotaxis was measured as described in FIG. 13. High levels of chemotactic inhibition were only seen with eosinophils from Donor 3 when Met-Ckβ-7* was placed in both the bottom and top wells.
Figure 18:
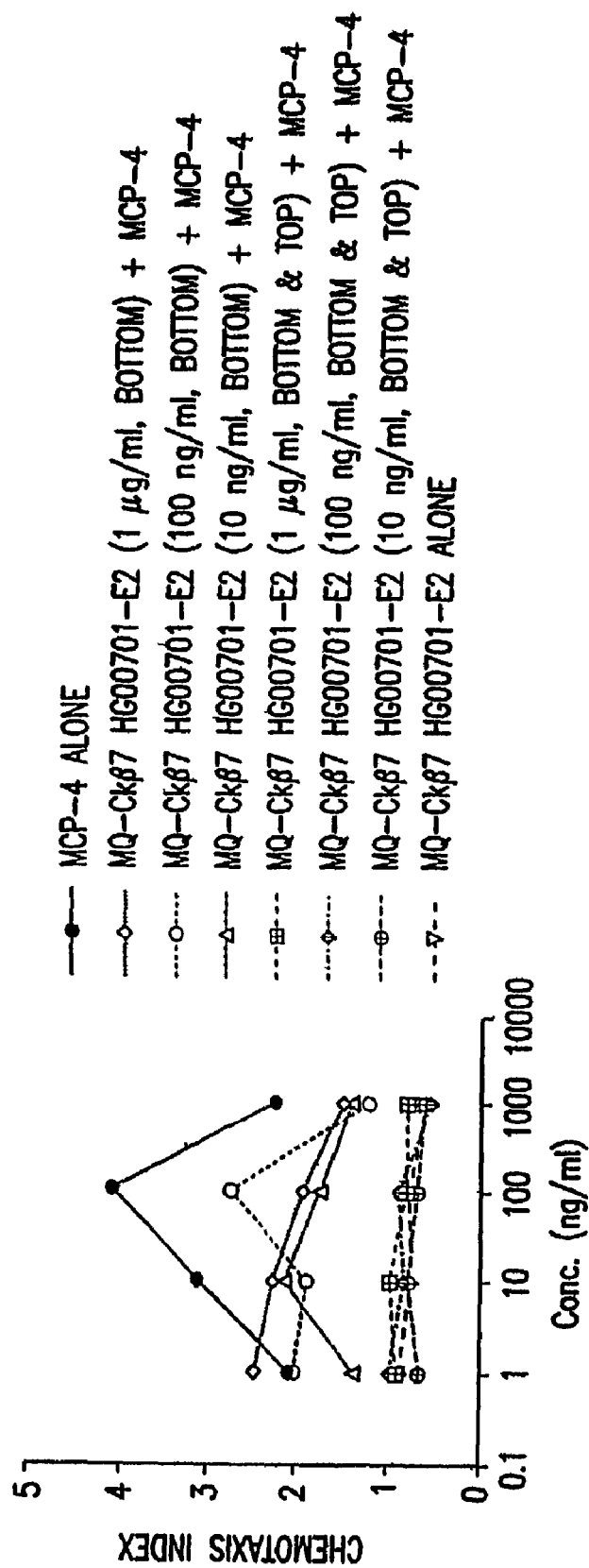
FIG. 18 shows Met-Ckβ-7* inhibition of MCP-4 induced eosinophil chemotaxis using eosinophils obtained from a single donor (Donor 3). Eosinophil chemotaxis was measured as described in FIG. 14. High levels of chemotactic inhibition were only seen with eosinophils from Donor 3 when Met-Ckβ-7* was placed in both the bottom and top wells.
Figure 19:
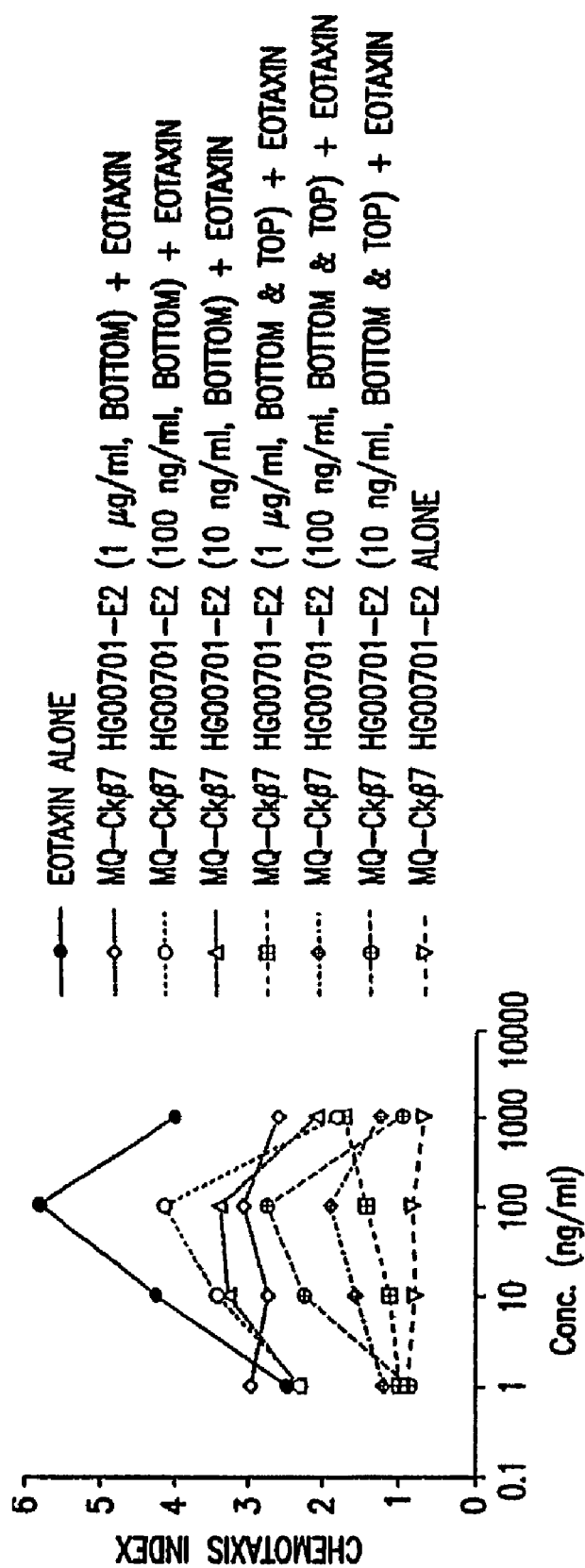
FIG. 19 shows Met-Ckβ-7* inhibition of Eotaxin induced eosinophil chemotaxis using eosinophils obtained from a single donor (Donor 4). Eosinophil chemotaxis was measured as described in FIG. 13. High levels of chemotactic inhibition were only seen with eosinophils-from Donor 4 when Met-Ckβ-7* was placed in both the bottom and top wells.
Figure 20:
FIG. 20 shows Met-Ckβ-7* inhibition of MCP-4 induced eosinophil chemotaxis using eosinophils obtained from a single donor (Donor 4). Eosinophil chemotaxis was measured as described in FIG. 14. High levels of chemotactic inhibition were only seen with eosinophils from Donor 4 when Met-Ckβ-7* was placed in both the bottom and top wells.

It has been discovered that several Ckβ-7 preparations (including Met-Ckβ-7, comprising amino acids 22–89 of SEQ ID NO:2 with an artificially encoded N-terminal methionine (i.e., Met-22–89 (SEQ ID NO:15)) and Met-Ckβ-7*, comprising amino acids 22–87 in SEQ ID NO:2 with an artificially encoded N-terminal methionine and a modification at the C-terminus (Met-22–87-Met-Pro-Glu-Ala (SEQ ID NO:16)) (see Example 4)) do not induce calcium flux or chemotactic activity in eosinophils. To the contrary, as shown in FIGS. 5–7 and 10–12, Met-Ckβ-7*, when premixed with various chemokine receptor-3 (CCR3) agonists, inhibits the eosinophil calcium response to the agonist. This CCR3 antagonist activity of Met-Ckβ-7* is dose-dependent when assayed against the CCR3 agonists Eotaxin (also know as MPIF-1), Eotaxin-2 (also know as Ckβ-6), and monocyte chemotactic protein-4 (MCP-4 (also known as Ckβ-10)), each alone or in combination. Met-Ckβ-7* completely inhibits such agonists at sufficiently high concentrations. Some inhibition of calcium response to RANTES and MCP-3 (two other CCR3 agonists) was also observed, but complete inhibition was not found (see FIG. 9), suggesting that these two ligands may still be able to signal through the CCR1 receptor. Met-Ckβ-7* was also shown to inhibit the chemotactic activity of Eotaxin and MCP-4 on eosinophils (see FIGS. 13–20). Met-Ckβ-7* and Met-Ckβ-7 have equivalent antagonist activity (see Example 4 and FIG. 33).

Figure 34:
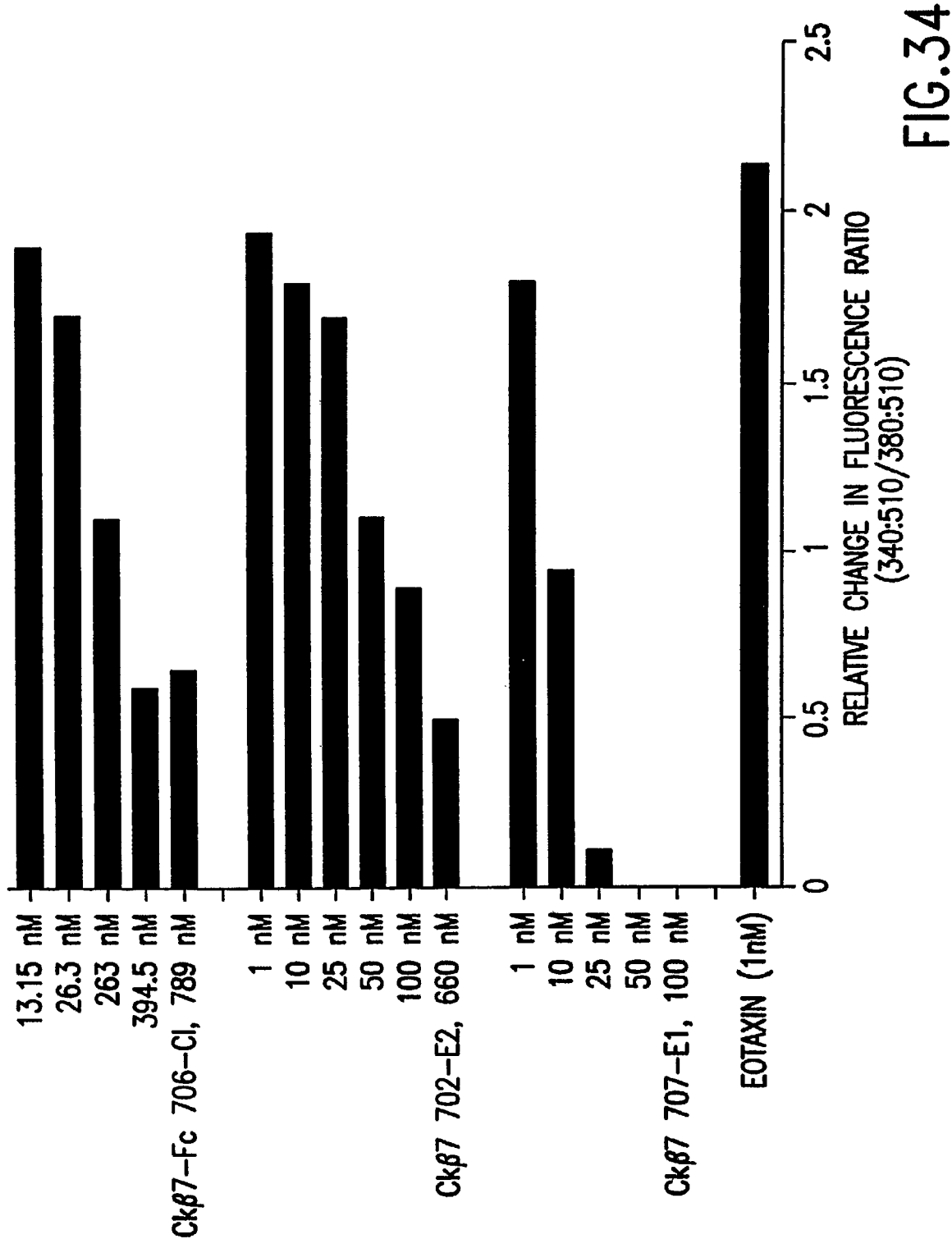
FIG. 34 shows the dose-response profile of inhibition of eotaxin-induced calcium mobilization in eosinophils with Met-Ckβ7 and a Met-Ckβ7 Fc variant. The Ckβ7 used (in the fusion and nonfusion forms) was the Ckβ7 fragment having amino acids 22–89 in SEQ ID No:2 and a methionine residue at the N-terminus (Met-22–89 (amino acids 21–89 in SEQ ID No:2)).

Additionally, an Ckβ7-Fc fusion retains antagonist activity (see FIG. 34).

Accordingly, Ckβ-7 polypeptides, and deletion mutants thereof, may be employed to treat inflammation by preventing the attraction of eosinophils or basophils to a wound or a site of trauma, and to regulate normal pulmonary macrophage populations, since acute and chronic inflammatory pulmonary diseases are associated with sequestration of mononuclear phagocytes in the lung. They may also be employed to treat rheumatoid arthritis, since MCP levels have been found to be significantly elevated in synovial fluid from rheumatoid arthritis patients which suggests that synovial production of MCPs attracts eosinophils or basophils whose influx and activation are important in the pathogenesis of both degenerative and inflammatory arthropathies.

Ckβ7 polypeptides, and deletion mutants thereof, may be employed during transplantation and in the treatment of kidney disease.

Ckβ-7 polypeptides may also be employed to treat allergies, since it has been shown that MCPs directly induce histamine release by basophils. Related immunological disorders including late phase allergic reactions, chronic urticaria, and atopic dermatitis can be treated by Ckβ-7 polypeptides which are effective to inhibit chemokine-induced mast cell and basophil degranulation and release of histamine. IgE-mediated allergic reactions such as asthma, rhinitis, psoriasis, scleroderma, eczema and other inflammatory dermatoses such as dermatitis, atopic dermatitis, allergic contact dermatitis, urticaria, and vasculitis (e.g., necrotizing, cutaneous, and hypersensitivity vasculitis) may also be treated. Ckβ-7 polypeptides may also be used to treat adult respiratory distress syndrome as well as airway inflammation. Other respiratory diseases treatable by Ckβ-7 polypeptides include, allergic rhinitis, hypersensitivity lung disease, hypersensitivity pneumonitis, eosinophilic pneumonias, (e.g., Loeffler's syndrome, chronic eosinophilic pneumonia), and interstitial lung disease (ILD) (e.g., idiopathic pulmonary fibrosis, or ILD associated with rheumatoid arthritis, systemic lupus erythematosis, ankylosing spondylitis, systemic sclerosis, Sjorgren's syndrome, polymyositis and dermatomyositis).

Ckβ-7 polypeptides may also be used to treat systemic anaphylaxis or hypersensitivity responses, drug allergies (e.g., to penicillin, cephalosporins), insect sting allergies, inflammatory bowel diseases, such as Chron's disease and ulcerative colitis, and spondyloarthropathies.

Ckβ-7 polypeptides may also be employed to treat idiopathic hyper-eosinophilic syndrome, eosinophilic myositis and eosinophilic fascitis by preventing eosinophil production and migration. Endotoxic shock may also be treated by the Ckβ-7 polypeptides by preventing the migration of macrophages and their production of chemokine (agonist) polypeptides.

Ckβ-7 polypeptides may be employed to interfere with the deleterious cascades attributed primarily to IL-1 and TNF, which prevents the biosynthesis of other inflammatory cytokines. In this way, the Ckβ-7 polypeptides may be employed to inhibit prostaglandin-independent fever induced by chemokines.

Ckβ-7 polypeptides may also be employed to treat bone marrow failure, for example, aplastic anemia and myelodysplastic syndrome. The Ckβ-7 polypeptides may also be employed to treat subepithelial basement membrane fibrosis which is a prominent feature of the asthmatic lung.

Ckβ-7 polypeptides may also be employed to inhibit HIV-1 infectivity as it has been shown that RANTES receptor antagonists such as Met-RANTES and AOP-RANTES inhibit HIV-1 infectivity in a number of immune cell types. See Simmons et al., *Science* 276:276 (1997).

Fragments, deletion mutants, substitution mutants, analogs and derivatives of Ckβ7 can also be used to treat the above diseases, disease states and syndromes, as can polynucleotides encoding these Ckβ7 polypeptides.

Ckβ-7 polypeptides may be employed in composition with a pharmaceutically acceptable carrier; e.g., as herein described.

Receptors

This invention provides a method for identification of the receptor for Ckβ-7. The gene encoding the receptor can be identified by numerous methods known to those of skill in the art, for example, ligand panning and FACS sorting (Coligan, et al., *Current Protocols in Immun.*, 1(2), Chapter 5, (1991)). Preferably, expression cloning is employed wherein polyadenylated RNA is prepared from a cell responsive to Ckβ-7, and a cDNA library created from this RNA is divided into pools and used to transfect COS cells or other cells that are not responsive to Ckβ-7. Transfected cells which are grown on glass slides are exposed to one or more labeled Ckβ-7 deletion mutant polypeptides of the invention. Ckβ-7 polypeptides of the invention can be labeled by a variety of means including iodination or inclusion of a recognition site for a site-specific protein kinase. Following fixation and incubation, the slides are subjected to autoradiographic analysis. Positive pools are identified and subpools are prepared and re-transfected using an iterative sub-pooling and re-screening process, eventually yielding a single clone that encodes the putative receptor. As an alternative approach for receptor identification, labeled ligand can be photoaffinity linked with cell membrane or extract preparations that express the receptor molecule. Cross-linked material is resolved by PAGE and exposed to X-ray film. The labeled complex containing the ligand-receptor can be excised, resolved into peptide fragments, and subjected to protein microsequencing. The amino acid sequence obtained from microsequencing would be used to design a set of degenerate oligonucleotide probes to screen a cDNA library to identify the gene encoding the putative receptor.

Pharmaceutical Compositions

The Ckβ-7 pharmaceutical composition of the invention comprises an effective amount of one or more isolated Ckβ-7 polypeptide effective to have a desired biological effect in an individual (e.g., decreasing a Ckβ-7 activity level, inhibiting the activity of a non-Ckβ-7 chemokine, or inhibiting the entry of HIV viral particles into leukocytes). Such compositions can be formulated and doses in a fashion consistent with good medical practice, taking into account the clinical condition of the individual patient (especially the side effects of treatment with Ckβ-7 polypeptide alone), the site of delivery of the polypeptide composition, the method of administration, the scheduling of administration, and other factors known to practitioners. The effective amount of Ckβ-7 polypeptide for purposes herein is thus determined by such considerations.

The polypeptides of the present invention may be employed in combination with a suitable pharmaceutical carrier. Such compositions comprise a therapeutically effective amount of the polypeptide or agonist or antagonist, and a pharmaceutically acceptable carrier or excipient. Such a carrier includes but is not limited to saline, buffered saline, dextrose, water, glycerol, ethanol, and combinations thereof. The formulation should suit the mode of administration.

By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The Ckβ-7 polypeptide is also suitably administered by sustained-release systems. Suitable examples of sustained-release compositions include semi-permeable polymer matrices in the form of shaped articles, e.g. films, or microcapsules. Sustained-release matrices include polylactides (U.S. Pat. No. 3,773,919, EP 58,481), copolymers of L-glutamic acid and gamma-ethyl-L-glutamate (Sidman, U., et al., Biopolymers 22:547–556 (1983)), poly (2-hydroxyethyl methacrylate) (R. Langer, et al., J. Biomed. Mater. Res. 15:167–277 (1981), and R. Langer, Chem. Tech. 12:98–105 (1982)), ethylene vinyl acetate (R. Langer, et al., Id.) or poly-D-(−)-3-hydroxybutyric acid (EP 133,988). Sustained-release Ckβ-7 polypeptide compositions also include liposomally entrapped Ckβ-7 polypeptide. Liposomes containing Ckβ-7 polypeptide are prepared by methods known per se: DE 3,218,121; Epstein, et al., Proc. Natl. Acad. Sci. (USA) 82:3688–3692 (1985); Hwang, et al., Proc. Natl. Acad. Sci. (USA) 77:4030–4034 (1980); EP 52,322; EP 36,676; EP 88,046; EP 143,949; EP 142,641; Japanese Pat. Appl. 83–118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Ckβ-7 polypeptide therapy.

For parenteral administration, in one embodiment, the Ckβ-7 polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Ckβ-7 polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g. polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Ckβ-7 polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of Ckβ-7 polypeptide salts.

Ckβ-7 polypeptide to be used for therapeutic administration must be sterile. Sterility is readily accomplished by filtration through sterile filtration membranes (e.g. 0.2 micron membranes). Therapeutic Ckβ-7 polypeptide compositions generally are placed into a container having a sterile access port, for example, an intravenous solution bag or vial having a stopper pierceable by a hypodermic injection needle.

Ckβ-7 polypeptide ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous Ckβ-7 polypeptide solution, and the resulting mixture is lyophilized. The infusion solution is prepared by reconstituting the lyophilized Ckβ-7 polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides, or agonists and antagonists, of the present invention may be employed in conjunction with other therapeutic compounds.

Ckβ7 may be administered alone or in combination with adjuvants. Adjuvants that may be administered with Ckβ7 include, but are not limited to, alum, alum plus deoxycholate (ImmunoAg), MTP-PE (Biocine Corp.), QS21 (Genentech, Inc.), BCG, and MPL. In a specific embodiment, Ckβ7 is administered in combination with alum. In another specific embodiment, Ckβ7 is administered in combination with QS-21. Further adjuvants that may be administered with Ckβ7 include, but are not limited to, monophosphoryl lipid immunomodulator, AdjuVax 100a, QS-21, QS-18, CRL1005, aluminum salts, MF-59, and virosomal adjuvant technology. Vaccines that may be administered with Ckβ7 include, but are not limited to, vaccines directed toward protection against MMR (measles, mumps, rubella), polio, varicella, tetanus/diptheria, hepatitis A, hepatitis B, *haemophilus influenzae* B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

Ckβ7 may be administered alone or in combination with other therapeutic agents. Therapeutic agents that may be administered in combination with Ckβ7, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In certain embodiments, Ckβ7 is administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with Ckβ7, include, but are not limited to, RETROVIR™ (zidovudine/AZT), VIDEX™ (didanosine/ddI), HVID™ (zalcitabine/ddC), ZERI™ (stavudine/d4T), EPIVIR™ (lamivudine/3TC), and COMBIVIR™ (zidovudine/lamivudine). Non-nucleoside reverse transcriptase inhibitors that may be administered in combination with Ckβ7, include, but are not limited to, VIRAMUNE™ (nevirapine), RESCRIPTOR™ (delavirdine), and SUSTIVA™ (efavirenz). Protease inhibitors that may be administered in combination with Ckβ7, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors maybe used in any combination with Ckβ7 to treat AIDS and/or to prevent or treat HIV infection.

In other embodiments, Ckβ7 may be administered in combination with anti-opportunistic infection agents. Anti-opportunistic agents that may be administered in combination with Ckβ7, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, Ckβ7 is used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, Ckβ7 is used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, Ckβ7 is used in any combination with RIFABUTIN™, CLARITHROMYCIN™, and/or AZITRHROMYCIN™ to prophylactically treat or prevent an opportunistic *Mycobacterium tuberculosis* infection. In another specific embodiment, Ckβ7 is used in any combination with GANCICLOVIR™, FOSCARNET™, and/or CIDOFOVIR™ to prophylactically treat or prevent an opportunistic cytomegalovirus infection. In another specific embodiment, Ckβ-7 is used in any combination with FLUCONAZOLE™, ITRACONAZOLE™, and/or KETOCONAZOLE™ to prophylactically treat or prevent an opportunistic fungal infection. In another specific embodiment, Ckβ7 is used in any combination with ACYCLOVIR™ and/or FAMCICOLVIR™ to prophylactically treat or prevent an opportunistic herpes simplex virus type I and/or type II infection. In another specific embodiment, Ckβ7 is used in any combination with PYRIMETHAMINE™ and/or LEUCOVORIN™ to prophylactically treat or prevent an opportunistic *Toxoplasma gondii* infection. In another specific embodiment, Ckβ7 is used in any combination with LEUCOVORIN™ and/or NEUPOGEN™ to prophylactically treat or prevent an opportunistic bacterial infection.

In a further embodiment, Ckβ7 is administered in combination with an antiviral agent. Antiviral agents that may be administered with Ckβ7 include, but are not limited to, acyclovir, ribavirin, amantadine, and remantidine.

In a further embodiment, Ckβ7 is administered in combination with an antibiotic agent. Antibiotic agents that may be administered with Ckβ7 include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with Ckβ7 include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Ckβ7 is administered in combination with immunosuppressants. Immunosuppressants preparations that may be administered with Ckβ-7 include, but are not limited to, ORTHOCLONE™ (OKT3), SAND-IMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In an additional embodiment, Ckβ7 is administered alone or in combination with one or more intravenous immune globulin preparations. Intravenous immune globulin preparations that may be administered with Ckβ7 include, but not limited to, GAMMAR™, WEEGAM™, SANDOGLOBULIN™, GAMMAGARD S/D™, and GAMIMUNE™. In a specific embodiment, Ckβ7 is administered in combination with intravenous immune globulin preparations in transplantation therapy (e.g., bone marrow transplant).

In an additional embodiment, Ckβ7 is administered alone or in combination with an anti-inflammatory agent. Anti-inflammatory agents that may be administered with Ckβ7 include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In an additional embodiment, Ckβ7 is administered in combination with cytokines. Cytokines that may be administered with Ckβ7 include, but are not limited to, IL2, IL3, IL4, IL5, IL6, IL7, IL10, 112, IL13, IL15, anti-CD40, CD40L, IFN-gamma and TNF-alpha. In another embodiment, Ckβ7 may be administered with any interleukin, including, but not limited to, IL-1alpha, IL-1beta, IL-2, IL-3, IL-4, IL-5, IL-6, IL-7, 1IL-8, IL-9, IL-10, IL-11, IL-12, IL-13, IL-14, IL-15, IL-16, IL-17, IL-18, IL-19, IL-20, and IL-21.

Additionally, the invention includes a vaccine composition. The composition includes a substantially isolated polypeptide and/or polynucleotide antigen, where the antigen includes an epitope which is specifically immunoreactive with at least antibody specific for the epitope. The peptide and/or polynucleotide antigen may be produced according to methods known in the art, including recombinant expression or chemical synthesis. The peptide antigen is preferably present in a pharmacologically effective dose in a pharmaceutically acceptable carrier.

Modes of Administration

It will be appreciated that conditions caused by a decrease in the standard or normal level of Ckβ-7 activity in an individual, can be treated by administration of Ckβ-7 polypeptides of the invention. Thus, the invention further provides a method of treating an individual in need of an increased level of Ckβ-7 activity comprising administering to such an individual a pharmaceutical composition comprising an amount of an isolated Ckβ-7 polypeptide of the invention, particularly a Ckβ-7 polypeptide which retains functional activities of the full-length and mature forms of Ckβ-7, effective to increase the Ckβ-7 activity level in such an individual.

It will also be appreciated that conditions caused by an increase in the standard or normal level of Ckβ-7 activity in an individual, can also be treated by administration of Ckβ-7 polypeptides of the invention. Thus, the invention further provides a method of treating an individual in need of an decreased level of Ckβ-7 activity comprising administering to such an individual a pharmaceutical composition comprising an amount of an isolated Ckβ-7 polypeptide of the invention, particularly a Ckβ-7 polypeptide which inhibits functional activities of the full-length and mature forms of Ckβ-7, effective to decrease the Ckβ-7 activity level in such an individual.

It will further be appreciated that conditions caused by an increase in the standard or normal level of the increase in activity of one or more non-Ckβ-7 chemokines in an individual (e.g., Eotaxin, Eotaxin-2, MCP-3, MCP-4, RANTES), can also be treated by administration of Ckβ-7 polypeptides of the invention. Thus, the invention further provides a method of treating an individual in need of an decreased level of non-Ckβ-7 chemokine activity comprising administering to such an individual a pharmaceutical composition comprising an amount of an isolated Ckβ-7 polypeptide of the invention effective to decrease the activity level of a one or more non-Ckβ-7 chemokines in such an individual.

The amounts and dosage regimens of Ckβ-7 administered to a subject will depend on a number of factors such as the mode of administration, the nature of the condition being treated and the judgment of the prescribing physician. The pharmaceutical compositions are administered in an amount which is effective for treating and/or prophylaxis of the specific indication. In general, the polypeptides will be administered in an amount of at least about 10 μg/kg body weight and in most cases they will be administered in an amount not in excess of about 10 mg/kg body weight per day and preferably the dosage is from about 10 μg/kg body weight daily, taking into account the routes of administration, symptoms, etc.

As a general proposition, the total pharmaceutically effective amount of Ckβ-7 polypeptide administered parenterally per dose will more preferably be in the range of about 1 μg/kg/day to 10 mg/kg/day of patient body weight, although, as noted above, this will be subject to therapeutic discretion. Even more preferably, this dose is at least 0.01 mg/kg/day, and most preferably for humans between about 0.01 and 1 mg/kg/day. If given continuously, the Ckβ-7 polypeptide is typically administered at a dose rate of about 1 μg/kg/hour to about 50 μg/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

The pharmaceutical compositions may be administered in a convenient manner such as by the oral, topical, parenterally, intravenous, intraperitoneal, intramuscular, subcutaneous, intranasal or intradermal routes.

Gene Therapy

The polypeptides of the invention may expressed in vivo for use in "gene therapy." Cells from a patient, for example, may be engineered with a polynucleotide (DNA or RNA) encoding a polypeptide ex vivo, with the engineered cells then being provided to a patient to be treated with the polypeptide. Such methods are well-known in the art and are apparent from the teachings herein. For example, cells may be engineered by the use of a retroviral plasmid vector containing RNA encoding a polypeptide of the present invention.

Similarly, cells may be engineered in vivo for expression of a polypeptide in vivo by, for example, procedures known in the art. For example, a packaging cell is transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention by such method should be apparent to those skilled in the art from the teachings of the present invention.

Retroviruses from which the retroviral plasmid vectors herein above mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

In a preferred embodiment the retroviral expression vector, pMV-7, is flanked by the long terminal repeats (LTRs) of the Moloney murine sarcoma virus and contains the selectable drug resistance gene neo under the regulation of the herpes simplex virus (HSV) thymidine kinase (tk) promoter. Unique EcoRI and HindIII sites facilitate the introduction of coding sequence (Kirschmeier, P. T., et al., *DNA* 7:219–25 (1988)).

The vector includes one or more promoters. Suitable promoters which may be employed include, but are not limited to, the retroviral LTR; the SV40 promoter; and the human cytomegalovirus (CMV) promoter described in Miller, et al., *Biotechniques* 7(9):980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the b-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, y-2, y-AM, PA12, T19-14×, VT-19-17-H2, yCRE, yCRIP, GP+E-86, GP+envAm12, and DAN cell lines as described in Miller, *Human Gene Therapy*, Vol. 1 (1990), pp. 5–14,, which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Another aspect of the present invention is to gene therapy methods for treating disorders, diseases and conditions. The gene therapy methods relate to the introduction of nucleic acid (DNA, RNA and antisense DNA or RNA) sequences into an animal to achieve expression of the Ckβ7 polypeptide of the present invention. This method requires a polynucleotide which codes for a Ckβ7 polypeptide operatively linked to a promoter and any other genetic elements necessary for the expression of the polypeptide by the target tissue. Such gene therapy and delivery techniques are known in the art, see, for example, WO 90/11092, which is herein incorporated by reference.

Thus, for example, cells from a patient may be engineered with a polynucleotide (DNA or RNA) comprising a promoter operably linked to a Ckβ7 polynucleotide ex vivo, with the engineered cells then being provided to a patient to be treated with the polypeptide. Such methods are well-known in the art. For example, see Belldegrun, A., et al., *J. Natl. Cancer Inst.* 85: 207–216 (1993); Ferrantini, M. et al., *Cancer Research* 53:1107–1112 (1993); Ferrantini, M. et al., *J. Immunology* 153: 4604–4615 (1994); Kaido, T., et al., *Int. J. Cancer* 60: 221–229 (1995); Ogura, H., et al., *Cancer Research* 50: 5102–5106 (1990); Santodonato, L., et al., *Human Gene Therapy* 7:1–10 (1996); Santodonato, L., et al., *Gene Therapy* 4:1246–1255 (1997); and Zhang, J.-F. et al., *Cancer Gene Therapy* 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the Ckβ7 polynucleotide constructs can be delivered by any method that delivers injectable materials to the cells of an animal, such as, injection into the interstitial space of tissues (heart, muscle, skin, lung, liver, and the like). The Ckβ7 polynucleotide constructs may be delivered in a pharmaceutically acceptable liquid or aqueous carrier.

In one embodiment, the Ckβ7 polynucleotide is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the Ckβ7 polynucleotides can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The Ckβ7polynucleotide vector constructs used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of Ckβ7 polynucleotide sequence. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for Ckβ7.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The Ckβ7 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, nondividing cells which are differentiated, although delivery and expression may be achieved in nondifferentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked Ckβ7 DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the Ckβ7 polynucleotide constructs are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., *Proc. Natl. Acad. Sci. USA* 84:74137416 (1987), which is herein incorporated by reference); mRNA (Malone et al., *Proc. Natl. Acad. Sci. USA* 86:60776081 (1989), which is herein incorporated by reference); and purified transcription factors (Debs et al., *J. Biol. Chem.* 265:1018910192 (1990), which is herein incorporated by reference), in functional form.

Cationic liposomes are readily available. For example, N-[12,3-dioleyloxy)-propyl]-N,N,N-triethylammonium (DOTMA) liposomes are particularly useful and are available under the trademark Lipofectin, from GIBCO BRL, Grand Island, N.Y. (See, also, Felgner et al., *Proc. Natl. Acad. Sci. USA* 84:74137416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication No. WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., P. Felgner et al., *Proc. Natl. Acad. Sci. USA* 84:74137417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially available dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15 EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposomenucleic acid complexes are prepared using methods well known in the art. See, e.g., Straubinger et al., *Methods of Immunology* 101:512527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., *Biochim. Biophys. Acta* 394:483 (1975); Wilson et al., *Cell* 17:77 (1979)); ether injection (Deamer, D. and Bangham, A., *Biochim. Biophys. Acta* 443:629 (1976); Ostro et al., *Biochem. Biophys. Res. Commun.* 76:836 (1977); Fraley et al., *Proc. Natl. Acad. Sci. USA* 76:3348 (1979)); detergent dialysis (Enoch, H. and Strittmatter, P., *Proc. Natl. Acad. Sci. USA* 76:145 (1979)); and reversephase evaporation (REV) (Fraley et al., *J. Biol. Chem.* 255:10431 (1980); Szoka, F. and Papahadjopoulos, D., *Proc. Natl. Acad. Sci. USA* 75:145 (1978); SchaeferRidder et al., *Science* 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication no. WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication no. WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding Ckβ7. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14x, VT-19-17-H2, RCRE, RCRIP, GP+E-86, GP+envAm12, and DAN cell lines as described in Miller, *Human Gene Therapy* 1:5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include polynucleotide encoding Ckβ7. Such retroviral vector particles then may be employed, to transduce eukaryotic cells, either in vitro or in vivo. The transduced eukaryotic cells will express Ckβ7.

In certain other embodiments, cells are engineered, ex vivo or in vivo, with Ckβ7 polynucleotide contained in an adenovirus vector. Adenovirus can be manipulated such that it encodes and expresses Ckβ7, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartz, A. R. et al. *Am. Rev. Respir. Dis.* 109:233–238 (1974)). Finally, adenovirus mediated gene transfer has been demonstrated in a number of instances including transfer of alphalantitrypsin and CFTR to the lungs of cotton rats (Rosenfeld, M. A. et al. *Science* 252:431–434 (1991); Rosenfeld et al., *Cell* 68:143–155 (1992)). Furthermore, extensive studies to attempt to establish adenovirus as a causative agent in human cancer were uniformly negative (Green, M. et al. *Proc. Natl. Acad. Sci. USA* 76:6606 (1979)).

Suitable adenoviral vectors useful in the present invention are described, for example, in Kozarsky and Wilson, *Curr. Opin. Genet. Devel.* 3:499–503 (1993); Rosenfeld et al., *Cell* 68:143–155 (1992); Engelhardt et al., *Human Genet. Ther.* 4:759–769 (1993); Yang et al., *Nature Genet.* 7:362–369 (1994); Wilson et al., *Nature* 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, N., Curr. Topics in Microbiol. Immunol. 158:97 (1992)). It is also one of the few viruses that may integrate its DNA into nondividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The Ckβ7 polynucleotide construct is inserted into the AAV vector using standard cloning methods, such as those found in Sambrook et al., *Molecular Cloning: A Laboratory Manual,* Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the Ckβ7 polynucleotide construct. These viral particles are then used to transduce eukaryotic cells, either ex vivo or in vivo. The transduced cells will contain the Ckβ7 polynucleotide construct integrated into its genome, and will express Ckβ7.

Another method of gene therapy involves operably associating heterologous control regions and endogenous polynucleotide sequences (e.g. encoding Ckβ7) via homologous recombination (see, e.g., U.S. Pat. No. 5,641,670, issued Jun. 24, 1997; International Publication No. WO 96/29411, published Sep. 26, 1996; International Publication No. WO 94/12650, published Aug. 4, 1994; Koller et al., *Proc. Natl. Acad. Sci. USA* 86:89328935 (1989); and Zijlstra et al., *Nature* 342:435438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the Ckβ7 desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous Ckβ7 sequence is placed under the control of the promoter. The promoter then drives the expression of the endogenous Ckβ7 sequence.

The polynucleotides encoding Ckβ7 may be administered along with other polynucleotides encoding an angiogenic protein. Examples of angiogenic proteins include, but are not limited to, acidic and basic fibroblast growth factors, VEGF-1, VEGF-2, VEGF-3, epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding Ckβ7 contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a proteincoated plasmid into the portal vein has resulted in gene expression of the foreign gene in the rat livers (Kaneda et al., *Science* 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA 189: 11277–11281, 1992, which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian.

Disease Diagnosis and Prognosis

Certain diseases or disorders, as discussed below, may be associated with altered (enhanced or reduced) levels of the Ckβ-7 protein and mRNA encoding the Ckβ-7 protein when compared to a corresponding "standard" mammal, i.e., a mammal of the same species not having the disease or disorder. Further, it is believed that altered levels of the Ckβ-7 protein can be detected in certain body fluids (e.g. sera, plasma, urine, and spinal fluid) from mammals with a disease or disorder when compared to sera from mammals of the same species not having the disease or disorder. Thus, the invention provides a diagnostic method, which involves assaying the expression level of the gene encoding the Ckβ-7 protein in mammalian cells or body fluid and comparing the gene expression level with a standard Ckβ-7 gene expression level, whereby an alteration in the gene expression level compared to the standard is indicative of certain diseases or disorders.

Where a disease or disorder diagnosis has already been made according to conventional methods, the present invention is useful as a prognostic indicator, whereby patients exhibiting altered Ckβ-7 gene expression will experience a worse clinical outcome relative to patients expressing the gene at a level closer to normal.

By "assaying the expression level of the gene encoding the Ckβ-7 protein" is intended qualitatively or quantitatively measuring or estimating the level of the Ckβ-7 protein or the level of the mRNA encoding the Ckβ-7 protein in a first biological sample either directly (e.g. by determining or estimating absolute protein level or mRNA level) or relatively (e.g. by comparing to the Ckβ-7 protein level or mRNA level in a second biological sample).

Preferably, the Ckβ-7 protein level or mRNA level in the first biological sample is measured or estimated and compared to a standard Ckβ-7 protein level or mRNA level, the standard being taken from a second biological sample obtained from an individual not having the disease or disorder. As will be appreciated in the art, once a standard Ckβ-7 protein level or mRNA level is known, it can be used repeatedly as a standard for comparison.

By "biological sample" is intended any biological sample obtained from an individual, cell line, tissue culture, or other source which contains Ckβ-7 protein or mRNA. Biological samples include mammalian body fluids (such as sera, plasma, urine, synovial fluid and spinal fluid) which contain secreted mature Ckβ-7 protein, and hematopoietic tissue. Methods for obtaining tissue biopsies and body fluids from mammals are well known in the art. Where the biological sample is to include mRNA, a tissue biopsy is the preferred source.

The present invention is useful for detecting disease in mammals. In particular the invention is useful during useful for diagnosis or treatment of various immune system-related disorders in mammals, preferably humans. Such disorders include tumors, cancers, and any disregulation of immune cell function including, but not limited to, autoimmunity, arthritis, immunosupression, sepsis, wound healing, acute and chronic infection, cell mediated immunity, humoral immunity, inflammatory bowel disease, asthma and the like. Preferred mammals include monkeys, apes, cats, dogs, cows, pigs, horses, rabbits and humans. Particularly preferred are humans.

Total cellular RNA can be isolated from a biological sample using any suitable technique such as the single-step guanidinium-thiocyanate phenol-chloroform method described in Chomczynski and Sacchi, Anal. Biochem. 162: 156–159 (1987). Levels of mRNA encoding the Ckβ-7 protein are then assayed using any appropriate method. These include Northern blot analysis, S1 nuclease mapping, the polymerase chain reaction (PCR), reverse transcription in combination with the polymerase chain reaction (RT-PCR), and reverse transcription in combination with the ligase chain reaction (RT-LCR).

Northern blot analysis can be performed as described in Harada et al., Cell 63:303–312 (1990). Briefly, total RNA is prepared from a biological sample as described above. For the Northern blot, the RNA is denatured in an appropriate buffer (such as glyoxal/dimethyl sulfoxide/sodium phosphate buffer), subjected to agarose gel electrophoresis, and transferred onto a nitrocellulose filter. After the RNAs have been linked to the filter by a UV linker, the filter is prehybridized in a solution containing formamide, SSC, Denhardt's solution, denatured salmon sperm, SDS, and sodium phosphate buffer. Ckβ-7 protein cDNA labeled according to any appropriate method (such as the $32^P$-multiprimed DNA labeling system (Amersham)) is used as probe. After hybridization overnight, the filter is washed and exposed to x-ray film. cDNA for use as probe according to the present invention is described in the sections above and will preferably at least 15 bp in length.

S1 mapping can be performed as described in Fujita et al., Cell 49:357–367 (1987). To prepare probe DNA for use in S1 mapping, the sense strand of above-described cDNA is used as a template to synthesize labeled antisense DNA. The antisense DNA can then be digested using an appropriate restriction endonuclease to generate further DNA probes of a desired length. Such antisense probes are useful for visualizing protected bands corresponding to the target mRNA (i.e., mRNA encoding the Ckβ-7 protein). Northern blot analysis can be performed as described above.

Preferably, levels of mRNA encoding the Ckβ-7 protein are assayed using the RT-PCR method described in Makino, et al., *Technique* 2:295–301 (1990).

Any set of oligonucleotide primers which will amplify reverse transcribed target mRNA can be used and can be designed as described in the sections above.

Assaying Ckβ-7 protein levels in a biological sample can occur using any art-known method. Preferred for assaying Ckβ-7 protein levels in a biological sample are antibody-based techniques. For example, Ckβ-7 protein expression in tissues can be studied with classical immunohistological methods. In these, the specific recognition is provided by the primary antibody (polyclonal or monoclonal) but the secondary detection system can utilize fluorescent, enzyme, or other conjugated secondary antibodies. As a result, an immunohistological staining of tissue section for pathological examination is obtained. Tissues can also be extracted, e.g. with urea and neutral detergent, for the liberation of Ckβ-7 protein for Western-blot or dot/slot assay (Jalkanen, M., et al., *J. Cell. Biol.* 101:976–985 (1985); Jalkanen, M., et al., *J. Cell. Biol.* 105:3087–3096 (1987)). In this technique, which is based on the use of cationic solid phases, quantitation of Ckβ-7 protein can be accomplished using isolated Ckβ-7 protein as a standard. This technique can also be applied to body fluids. With these samples, a molar concentration of Ckβ-7 protein will aid to set standard values of Ckβ-7 protein content for different body fluids, like serum, plasma, urine, spinal fluid, etc. The normal appearance of Ckβ-7 protein amounts can then be set using values from healthy individuals, which can be compared to those obtained from a test subject.

Other antibody-based methods useful for detecting Ckβ-7 protein gene expression include immunoassays, such as the enzyme linked immunosorbent assay (ELISA) and the radioimmunoassay (RIA). For example, a Ckβ-7 protein-specific monoclonal antibodies can be used both as an immunoabsorbent and as an enzyme-labeled probe to detect and quantify the Ckβ-7 protein. The amount of Ckβ-7 protein present in the sample can be calculated by reference to the amount present in a standard preparation using a linear regression computer algorithm. In another ELISA assay, two distinct specific monoclonal antibodies can be used to detect Ckβ-7 protein in a body fluid. In this assay, one of the antibodies is used as the immunoabsorbent and the other as the enzyme-labeled probe.

The above techniques may be conducted essentially as a "one-step" or "two-step" assay. The "one-step" assay involves contacting Ckβ-7 protein with immobilized antibody and, without washing, contacting the mixture with the labeled antibody. The "two-step" assay involves washing before contacting the mixture with the labeled antibody. Other conventional methods may also be employed as suitable. It is usually desirable to immobilize one component of the assay system on a support, thereby allowing other components of the system to be brought into contact with the component and readily removed from the sample.

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labelled antibody/substrate reaction. Besides enzymes, other suitable labels include radioisotopes, such as iodine ($^{125}$I, $^{121}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

The polypeptides of the present invention, and polynucleotides encoding such polypeptides, may be employed as research reagents for in vitro purposes related to scientific research, synthesis of DNA and manufacture of DNA vectors, and for the purpose of developing therapeutics and diagnostics for the treatment of human disease. For example, Ckβ-7 may be employed for the expansion of immature hematopoietic progenitor cells, for example, granulocytes, macrophages or monocytes, by temporarily preventing their differentiation. These bone marrow cells may be cultured in vitro.

Fragments of the full length Ckβ-7 genes may be used as a hybridization probe for a cDNA library to isolate the full length gene and to isolate other genes which have a high sequence similarity to the gene or similar biological activity.

This invention is also related to the use of the gene of the present invention as a diagnostic. Detection of a mutated form of the gene will allow a diagnosis of a disease or a susceptibility to a disease which results from underexpression of Ckβ-7.

Individuals carrying mutations in the gene of the present invention may be detected at the DNA level by a variety of techniques. Nucleic acids for diagnosis may be obtained from a patient's cells, including but not limited to blood, urine, saliva, tissue biopsy and autopsy material. The genomic DNA may be used directly for detection or may be amplified enzymatically by using PCR (Saiki et al., *Nature* 324:163–166 (1986)) prior to analysis. RNA or cDNA may also be used for the same purpose. As an example, PCR primers complementary to the nucleic acid encoding Ckβ-7 can be used to identify and analyze mutations. For example, deletions and insertions can be detected by a change in size of the amplified product in comparison to the normal genotype. Point mutations can be identified by hybridizing amplified DNA to radiolabeled RNA or alternatively, radiolabeled antisense DNA sequences. Perfectly matched sequences can be distinguished from mismatched duplexes by RNase A digestion or by differences in melting temperatures.

Sequence differences between the reference gene and genes having mutations may be revealed by the direct DNA sequencing method. In addition, cloned DNA segments may be employed as probes to detect specific DNA segments. The sensitivity of this method is greatly enhanced when combined with PCR. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations may also be revealed by nuclease protection assays, such as RNase and S1 protection or the chemical cleavage method (e.g., Cotton et al., *Proc. Natl. Acad. Sci.* (*USA*) 85:4397–4401 (1985)).

The present invention also relates to a diagnostic assay for detecting altered levels of the polypeptide of the present invention in various tissues since an over-expression of the proteins compared to normal control tissue samples may detect the presence of a disease or susceptibility to a disease, for example, a tumor. Assays used to detect levels of the polypeptide of the present invention in a sample derived from a host are well-known to those of skill in the art and include radioimmunoassays, competitive-binding assays, Western Blot analysis, ELISA assays and sandwich assays. See, e.g., Coligan, et al., *Current Protocols in Immunology* 1(2), Chapter 6, (1991), which is incorporated herein by reference.

This invention provides a method for identification of the receptors for the chemokine polypeptides. The gene encoding the receptor can be identified by numerous methods known to those of skill in the art, for example, ligand panning and FACS sorting. See, e.g., Coligan, et al., *Current Protocols in Immunology* 1(2), Chapter 5, (1991), which is incorporated herein by reference.

Chromosome Assays

The nucleic acids of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

In certain preferred embodiments in this regard, the cDNA herein disclosed is used to clone genomic DNA of a Ckβ-7 protein gene. This can be accomplished using a variety of well known techniques and libraries, which are generally available commercially. The genomic DNA this is used for in situ chromosome mapping using well known techniques for this purpose. Typically in accordance with routine procedures for chromosome mapping, some trial and error may be necessary to identify a genomic probe that gives a good in situ hybridization signal.

Briefly, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA having at least 50 or 60 bases. For a review of this technique, see Verma et al., *Human Chromosomes: a Manual of Basic Techniques,* Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man* (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

Comparison of affected and unaffected individuals generally involves first looking for structural alterations in the chromosomes, such as deletions or translocations that are visible from chromosome spreads or detectable using PCR based on that cDNA sequence. Ultimately, complete sequencing of genes from several individuals is required to confirm the presence of a mutation and to distinguish mutations from polymorphisms.

Antibodies

Ckβ-7-protein specific antibodies for use in the present invention can be raised against the intact Ckβ-7 protein or an antigenic polypeptide fragment thereof, which may presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to Ckβ-7 protein. Fab and F(ab')2 fragments lack the Fc fragment of intact antibody, clear more rapidly from the circulation, and may have less non-specific tissue binding of an intact antibody (Wahl, et al., *J. Nucl. Med.* 24:316–325 (1983)). Thus, these fragments are preferred.

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, *Nature* 256:495–497 (1975)), the trioma technique, the human B-cell hybridoma technique (Kozbor, et al., *Immunology Today* 4:72 (1983)), and the EBV-hybridoma technique to produce human monoclonal antibodies (Cole, et al., in *Monoclonal Antibodies and Cancer Therapy,* Alan R. Liss, Inc. (1985), pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The antibodies of the present invention may be prepared by any of a variety of methods. For example, cells expressing the Ckβ-7 protein or an antigenic fragment thereof can be administered to an animal in order to induce the production of sera containing polyclonal antibodies. In a preferred method, a preparation of Ckβ-7 protein is prepared and purified to render it substantially free of natural contaminants. Such a preparation is then introduced into an animal in order to produce polyclonal antisera of greater specific activity.

In the present invention, antigenic epitopes preferably contain a sequence of at least 4, at least 5, at least 6, at least 7, more preferably at least 8, at least 9, at least 10, at least 15, at least 20, at least 25, and most preferably between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Antigenic epitopes are useful, for example, to raise antibodies, including monoclonal antibodies, that specifically bind the epitope. (See, for instance, Wilson et al., *Cell* 37:767–778 (1984); Sutcliffe et al., *Science* 219:660–666 (1983).)

Similarly, immunogenic epitopes can be used, for example, to induce antibodies according to methods well known in the art. (See, for instance, Sutcliffe et al., supra; Wilson et al., supra; Chow et al., *Proc. Natl. Acad. Sci. USA* 82:910–914; and Bittle et al., *J. Gen. Virol.* 66:2347–2354 (1985).) A preferred immunogenic epitope includes the secreted protein. The immunogenic epitopes may be presented together with a carrier protein, such as an albumin, to an animal system (such as rabbit or mouse) or, if it is long enough (at least about 25 amino acids), without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting.)

Epitope bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., *J. Gen. Virol.* 66:23472354 (1985). If in vivo immunization is used, animals may be immunized with free peptide; however, antipeptide antibody titer may be boosted by coupling of the peptide to a macromolecular carrier, such as keyhole limpet hemacyanin (KLH) or tetanus toxoid. For instance, peptides containing cysteine residues may be coupled to a carrier using a linker such as maleimidobenzoyl N-hydroxysuccinimide ester (MBS), while other peptides may be coupled to carriers using a more general linking agent such as glutaraldehyde. Animals such as rabbits, rats and mice are immunized with either free or carriercoupled peptides, for instance, by intraperitoneal and/or intradermal injection of emulsions containing about 100 μgs of peptide or carrier protein and Freund's adjuvant. Several booster injections may be needed, for instance, at intervals of about two weeks, to provide a useful titer of antipeptide antibody which can be detected, for example, by ELISA assay using free peptide adsorbed to a solid surface. The titer of antipeptide antibodies in serum from an immunized animal may be increased by selection of antipeptide antibodies, for instance, by adsorption to the peptide on a solid support and elution of the selected antibodies according to methods well known in the art.

As one of skill in the art will appreciate, and discussed above, the polypeptides of the present invention comprising an immunogenic or antigenic epitope can be fused to heterologous polypeptide sequences. For example, the polypeptides of the present invention may be fused with the constant domain of immunoglobulins (IgA, IgE, IgG, IgM), or portions thereof ($CH_1$, $CH_2$, $CH_3$, any combination thereof including both entire domains and portions thereof) resulting in chimeric polypeptides. These fusion proteins facilitate purification, and show an increased halflife in vivo. This has been shown, e.g., for chimeric proteins consisting of the first two domains of the human CD4 polypeptide and various domains of the constant regions of the heavy or light chains of mammalian immunoglobulins. See, e.g., EPA 0,394,827; Traunecker et al., *Nature* 331:8486 (1988). Fusion proteins that have a disulfidelinked dimeric structure due to the IgG portion can also be more efficient in binding and neutralizing other molecules than monomeric polypeptides or fragments thereof alone. See, e.g., Fountoulakis et al., *J. Biochem.* 270:39583964 (1995). Nucleic acids encoding the above epitopes can also be recombined with a gene of interest as an epitope tag to aid in detection and purification of the expressed polypeptide.

In the most preferred method, the antibodies of the present invention are monoclonal antibodies (or Ckβ-7 protein binding fragments thereof). Such monoclonal antibodies can be prepared using hybridoma technology (Kohler, et al, *Nature* 256:495 (1975); Kohler, et al., *Eur. J. Immunol.* 6:511 (1976); Kohler, et al., *Eur. J. Immunol.* 6:292 (1976); Hammerling, et al., in *Monoclonal Antibodies and T-Cell Hybridomas,* Elsevier, N.Y., (1981), pp. 563–681).

Alternatively, additional antibodies capable of binding to the Ckβ-7 protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, Ckβ-7-protein specific antibodies are used to immunize an animal, preferably a mouse. The splenocytes of such an animal are then used to produce hybridoma cells, and the hybridoma cells are screened to identify clones which produce an antibody whose ability to bind to the Ckβ-7 protein-specific antibody can be blocked by the Ckβ-7 protein antigen. Such antibodies comprise anti-idiotypic antibodies to the Ckβ-7 protein-specific antibody and can be used to immunize an animal to induce formation of further Ckβ-7 protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, Ckβ-7 protein-binding fragments can be produced through the application of recombinant DNA technology or through synthetic chemistry.

It may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi, et al., *BioTechniques* 4:214 (1986); Cabilly, et al., U.S. Pat. No. 4,816,567; Taniguchi, et al., EP 171496; Morrison, et al., EP 173494; Neuberger, et al., WO 8601533; Robinson, et al., WO 8702671; Boulianne, et al., *Nature* 312:643 (1984); Neuberger, et al., *Nature* 314:268 (1985).

The present invention further relates to antibodies and T-cell antigen receptors (TCR) which specifically bind the polypeptides of the present invention. The antibodies of the present invention include IgG (including $IgG_1$, $IgG_2$, $IgG_3$, and $IgG_4$), IgA (including $IgA_1$ and $IgA_2$), IgD, IgE, IgM, and IgY. As used herein, the term "antibody" (Ab) is meant to include whole antibodies, including single-chain whole antibodies, and antigen-binding fragments thereof. Most preferably the antibodies are human antigen binding antibody fragments of the present invention and include, but are not limited to, Fab, Fab' and $F(ab')_2$, Fd, single-chain Fvs (scFv), single-chain antibodies, disulfide-linked Fvs (sdFv) and fragments comprising either a $V_L$ or $V_H$ domain. The antibodies may be from any animal origin including birds and mammals. Preferably, the antibodies are human, murine, rabbit, goat, guinea pig, camel, horse, or chicken.

Antigen-binding antibody fragments, including single-chain antibodies, may comprise the variable region(s) alone or in combination with the entire or partial of the following: hinge region, $CH_1$, $CH_2$, and $CH_3$ domains. Also included in the invention are any combinations of variable region(s) and hinge region, $CH_1$, $CH_2$, and $CH_3$ domains. The present invention further includes monoclonal, polyclonal, chimeric, humanized, and human monoclonal and human polyclonal antibodies which specifically bind the polypeptides of the present invention. The present invention further includes antibodies which are anti-idiotypic to the antibodies of the present invention.

The antibodies of the present invention may be monospecific, bispecific, trispecific or of greater multispecificity. Multispecific antibodies maybe specific for different epitopes of a polypeptide of the present invention or may be specific for both a polypeptide of the present invention as well as for heterologous compositions, such as a heterologous polypeptide or solid support material. See, e.g., WO 93/17715; WO 92/08802; WO 91/00360; WO 92/05793; Tutt, et al., *J. Immunol.* 147:60–69 (1991); U.S. Pat. Nos. 5,573,920, 4,474,893, 5,601,819, 4,714,681, 4,925,648; Kostelny et al., *J. Immunol.* 148:1547–1553 (1992).

Antibodies of the present invention may be described or specified in terms of the epitope(s) or portion(s) of a polypeptide of the present invention which are recognized or specifically bound by the antibody. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of the polypeptides of the present invention are included. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. Further included in the present invention are antibodies which only bind polypeptides encoded by polynucleotides which hybridize to a polynucleotide of the present invention under stringent hybridization conditions (as described herein). Antibodies of the present invention may also be described or specified in terms of their binding affinity. Preferred binding affinities include those with a dissociation constant or Kd less than $5\times10^{-6}$M, $10^{-6}$M, $5\times10^{-7}$M, $10^{-7}$M, $5\times10^{-8}$M, $10^{-8}$M, $5\times10^{-9}$M, $10^{-9}$M, $5\times10^{-10}$M, $10^{-10}$M, $5\times10^{-11}$M, $10^{-11}$M, $5\times10^{-12}$M, $10^{-12}$M, $5\times10^{-13}$M, $10^{-13}$M, $5\times10^{-14}$M, $10^{-14}$M, $5\times10^{-15}$M, and $10^{-15}$M.

Antibodies of the present invention have uses that include, but are not limited to, methods known in the art to purify, detect, and target the polypeptides of the present invention including both in vitro and in vivo diagnostic and therapeutic methods. For example, the antibodies have use in immunoassays for qualitatively and quantitatively measuring levels of the polypeptides of the present invention in biological samples. See, e.g., Harlow et al., *Antibodies: a Laboratory Manual,* (Cold Spring Harbor Laboratory Press, 2nd ed. 1988) (incorporated by reference in the entirety).

The antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, or toxins. See, e.g., WO 92/08495; WO 91/14438; WO 89/12624; U.S. Pat. No. 5,314,995; and EP 0 396 387.

The antibodies of the present invention may be prepared by any suitable method known in the art. For example, a polypeptide of the present invention or an antigenic fragment thereof can be administered to an animal in order to induce the production of sera containing polyclonal antibodies. The term "monoclonal antibody" is not a limited to antibodies produced through hybridoma technology. The term "monoclonal antibody" refers to an antibody that is derived from a single clone, including any eukaryotic, prokaryotic, or phage clone, and not the method by which it is produced. Monoclonal antibodies can be prepared using a wide variety of techniques known in the art including the use of hybridoma, recombinant, and phage display technology.

Hybridoma techniques include those known in the art and taught in Harlow et al., *Antibodies: a Laboratory Manual,* (Cold Spring Harbor Laboratory Press, 2nd ed. 1988); Hammerling, et al., in: *Monoclonal Antibodies and T cell Hybridomas* 563681 (Elsevier, N.Y., 1981) (said references incorporated by reference in their entireties). Fab and F(ab')2 fragments may be produced by proteolytic cleavage, using enzymes such as papain (to produce Fab fragments) or pepsin (to produce F(ab')2 fragments).

Alternatively, antibodies of the present invention can be produced through the application of recombinant DNA and phage display technology or through synthetic chemistry using methods known in the art. For example, the antibodies of the present invention can be prepared using various phage display methods known in the art. In phage display methods, functional antibody domains are displayed on the surface of a phage particle which carries polynucleotide sequences encoding them. Phage with a desired binding property are selected from a repertoire or combinatorial antibody library (e.g. human or murine) by selecting directly with antigen, typically antigen bound or captured to a solid surface or bead. Phage used in these methods are typically filamentous phage including fd and M13 with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41–50 (1995); Ames et al., *J. Immunol. Methods* 184:177–186 (1995); Kettleborough et al., *Eur. J. Immunol.* 24:952–958 (1994); Persic et al., *Gene* 187:9–18 (1997); Burton et al., *Advances in Immunology* 57:191–280 (1994); PCT/GB91/01134; WO 90/02809; WO 91/10737; WO 92/01047; WO 92/18619; WO 93/11236; WO 95/15982; WO 95/20401; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743 (said references incorporated by reference in their entireties).

As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')2 fragments can also be employed using methods known in the art such as those disclosed in WO 92/22324; Mullinax et al., *BioTechniques* 12(6):864–869 (1992); and Sawai et al., *AJRI* 34:26–34 (1995); and Better et al., *Science* 240:1041–1043 (1988) (said references incorporated by reference in their entireties).

Examples of techniques which can be used to produce single-chain Fvs and antibodies include those described in U.S. Pat. Nos. 4,946,778 and 5,258,498; Huston et al., *Methods in Enzymology* 203:46–88 (1991); Shu, L. et al., *PNAS* 90:7995–7999 (1993); and Skerra et al., *Science* 240:1038–1040 (1988). For some uses, including in vivo use of antibodies in humans and in vitro detection assays, it may be preferable to use chimeric, humanized, or human antibodies. Methods for producing chimeric antibodies are known in the art. See e.g., Morrison, Science 229:1202 (1985); Oi et al., *BioTechniques* 4:214 (1986); Gillies et al., *J. Immunol. Methods* 125:191–202 (1989); and U.S. Pat. No. 5,807,715. Antibodies can be humanized using a variety of techniques including CDR-grafting (EP 0 239 400; WO 91/09967; U.S. Pat. Nos. 5,530,101; and 5,585,089), veneering or resurfacing (EP 0 592 106; EP 0 519 596; Padlan E. A., *Molecular Immunology* 28(4/5):489–498 (1991); Studnicka et al., *Protein Engineering* 7(6):805–814 (1994); Roguska. et al., *PNAS* 91:969–973 (1994)), and chain shuffling (U.S. Pat. No. 5,565,332). Human antibodies can be made by a variety of methods known in the art including phage display methods described above. See also, U.S. Pat. Nos. 4,444,887, 4,716,111, 5,545,806, and 5,814,318; and WO 98/46645, WO 98/50433, WO 98/24893, WO 98/16654, WO 96/34096, WO 96/33735, and WO 91/10741 (said references incorporated by reference in their entireties).

The invention further relates to antibodies which act as agonists or antagonists of the polypeptides of the present invention. For example, the present invention includes antibodies which disrupt the receptor/ligand interactions with the polypeptides of the invention either partially or fully. Included are both receptor-specific antibodies and ligand-specific antibodies. Included are receptor-specific antibodies which do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies which activate the receptor. These antibodies may act as agonists for either all or less than all of the biological activities affected by ligand-mediated receptor activation. The antibodies may be specified as agonists or antagonists for biological activities comprising specific activities disclosed herein. The above antibody agonists can be made using methods known in the art. See e.g., WO 96/40281; U.S. Pat. No. 5,811,097; Deng et al., *Blood* 92(6):1981–1988 (1998); Chen, et al., *Cancer Res.* 58(16):3668–3678 (1998); Harrop et al., *J. Immunol.* 161(4): 1786–1794 (1998); Zhu et al., *Cancer Res.* 58(15):3209–3214 (1998); Yoon, et al., *J. Immunol.* 160(7):3170–3179 (1998); Prat et al., *J. Cell. Sci.* 111(Pt2):237–247 (1998); Pitard et al., *J. Immunol. Methods* 205(2):177–190 (1997); Liautard et al., *Cytokine* 9(4):233–241 (1997); Carlson et al., *J. Biol. Chem.* 272(17): 11295–11301 (1997); Taryman et al., *Neuron* 14(4):755–762 (1995); Muller et al., *Structure* 6(9):1153–1167 (1998); Bartunek et al., *Cytokine* 8(1):14–20 (1996) (said references incorporated by reference in their entireties).

As discussed above, antibodies to the polypeptides of the invention can, in turn, be utilized to generate anti-idiotype antibodies that "mimic" polypeptides of the invention using techniques well known to those skilled in the art. (See, e.g., Greenspan & Bona, *FASEB J.* 7(5):437–444; (1989) and Nissinoff, *J. Immunol.* 147(8):2429–2438 (1991)). For example, antibodies which bind to and competitively inhibit polypeptide multimerization and/or binding of a polypeptide of the invention to ligand can be used to generate anti-idiotypes that "mimic" the polypeptide mutimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labelled monoclonal antibody. Alternatively, or in addition, the detecting means may include a labelled, competing antigen.

In a more specific embodiment the detecting means of the above-described kit includes a solid support to which said polypeptide antigen is attached. Such a kit may also include a non-attached reporter-labelled anti-human antibody. In this embodiment, binding of the antibody to the polypeptide antigen can be detected by binding of the said reporter-labeled antibody.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labelled anti-human antibody to bind reporter to the reagent in proportion to the amount of bound anti-antigen antibody on the solid support. The reagent is again washed to remove unbound labelled antibody, and the amount of reporter associated with the reagent is determined. Typically, the reporter is an enzyme which is detected by incubating the solid phase in the presence of a suitable fluorometric or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention proveds an assay system or kit for carrying out this diagnostic method. The kit generally includes a support with surface-bound recombinant antigens, and a reporter-labelled anti-human antibody for detecting surface-bound anti-antigen antibody.

Further suitable labels for the Ckβ-7 protein-specific antibodies of the present invention are provided below. Examples of suitable enzyme labels include malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, 58Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins, et al., *Eur. J. Nucl. Med.* 10:296–301 (1985); Carasquillo, et al., *J. Nucl. Med.* 28:281–287 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include diphtheria toxin, ricin, and cholera toxin.

Examples of chemiluminescent labels include a luminal label, an isolurminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to antibodies are provided by Kennedy, et al., *Clin. Chim. Acta* 70:1–31 (1976), and Schurs, et al., *Clin. Chim. Acta* 81:1–40 (1977). Coupling techniques mentioned in the latter are the glutaraldehyde method, the periodate method, the dimaleimide method, the m-maleimidobenzyl-N-hydroxysuccinimide ester method, all of which methods are incorporated by reference herein.

Fusion Proteins

As one of skill in the art will appreciate, and discussed above, the polypeptides of the present invention comprising an immunogenic or antigenic epitope can be fused to heterologous polypeptide sequences.

As shown in FIG. 34, a Ckβ7-Fc fusion retains antagonist activity in eosinophil calcium mobilization assays.

Thus, for example, the polypeptides of the present invention may be fused with the constant domain of immunoglobulins (IgA, IgE, IgG, IgM), or portions thereof (CH$_1$, CH$_2$, CH$_3$, any combination thereof including both entire domains and portions thereof) resulting in chimeric polypeptides. These fusion proteins facilitate purification, and show an increased halflife in vivo. This has been shown, e.g., for chimeric proteins consisting of the first two domains of the human CD4 polypeptide and various domains of the constant regions of the heavy or light chains of mammalian immunoglobulins. See, e.g., EPA 0,394,827; Traunecker et al., *Nature* 331:8486 (1988). Fusion proteins that have a disulfidelinked dimeric structure due to the IgG portion can also be more efficient in binding and neutralizing other molecules than monomeric polypeptides or fragments thereof alone. See, e.g., Fountoulakis et al., *J. Biochem.* 270:39583964 (1995). Nucleic acids encoding the above epitopes can also be recombined with a gene of interest as an epitope tag to aid in detection and purification of the expressed polypeptide.

Similarly, EP-A-O 464 533 (Canadian counterpart 2045869) discloses fusion proteins comprising various portions of constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., *J. Molecular Recognition* 8:52–58 (1995); K. Johanson et al., *J. Biol. Chem.* 270: 9459–9471 (1995).)

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides corresponding to SEQ ID NO:2 thereby effectively generating agonists and antagonists of the polypeptides. See, generally, U.S. Pat. Nos. 5,605,793, 5,811,238, 5,830,721, 5,834,252, and 5,837,458, and Patten, P. A., et al., *Curr. Opinion Biotechnol.* 8:724–33 (1997); Harayama, S., *Trends Biotechnol.* 16(2):76–82 (1998); Hansson, L. O., et al., *J. Mol. Biol.* 287:265–76 (1999); and Lorenzo, M. M. and Blasco, R., *Biotechniques* 24(2):308–13 (1998) (each of these patents and publications are hereby incorporated by reference). In one embodiment, alteration of polynucleotides corresponding to SEQ ID NO:1 and corresponding polypeptides may be achieved by DNA shuffling. DNA shuffling involves the assembly of two or more DNA segments into a desired molecule corresponding to SEQ ID NO:1 polynucleotides of the invention by homologous, or site-specific, recombination. In another embodiment, polynucleotides corresponding to SEQ ID NO:1 and corresponding polypeptides may be altered by being subjected to random mutagenesis by error-prone PCR, random nucleotide insertion or other methods prior to recombination. In another embodiment, one or more components, motifs, sections, parts, domains, fragments, etc., of coding polynucleotide corresponding to SEQ ID NO:1, or the polypeptide encoded thereby may be recombined with one or more components, motifs, sections, parts, domains, fragments, etc. of one or more heterologous molecules.

Any Ckβ7 polypeptide can be used to generate fusion proteins. For example, the Ckβ7 polypeptide, when fused to a second protein, can be used as an antigenic tag. Antibodies raised against the Ckβ7 polypeptide can be used to indirectly detect the second protein by binding to the Ckβ7. Moreover, because secreted proteins target cellular locations based on trafficking signals, the Ckβ7 polypeptides can be used as targeting molecules once fused to other proteins.

Examples of domains that can be fused to Ckβ7 polypeptides include not only heterologous signal sequences, but also other heterologous functional regions. The fusion does not necessarily need to be direct, but may occur through linker sequences.

In certain preferred embodiments, Ckβ7 proteins of the invention comprise fusion proteins wherein the Ckβ7 polypeptides are those described above as m-n. In preferred embodiments, the application is directed to nucleic acid molecules at least 90%, 95%, 96%, 97%, 98% or 99% identical to the nucleic acid sequences encoding polypeptides having the amino acid sequence of the specific N and C-terminal deletions recited herein. Polynucleotides encoding these polypeptides are also encompassed by the invention.

Moreover, fusion proteins may also be engineered to improve characteristics of the Ckβ7 polypeptide. For instance, a region of additional amino acids, particularly charged amino acids, may be added to the N-terminus of the Ckβ7 polypeptide to improve stability and persistence during purification from the host cell or subsequent handling and storage. Also, peptide moieties may be added to the Ckβ7 polypeptide to facilitate purification. Such regions may be removed prior to final preparation of the Ckβ7 polypeptide. The addition of peptide moieties to facilitate handling of polypeptides are familiar and routine techniques in the art.

Further included in the present invention are antibodies recombinantly fused or chemically conjugated (including both covalently and non-covalently conjugations) to a polypeptide of the present invention. The antibodies may be specific for antigens other than polypeptides of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al. supra and WO 93/21232; EP 0 439 095; Naramura et al., *Immunol. Lett.* 39:91–99 (1994); U.S. Pat. No. 5,474,981; Gillies et al., PNAS 89:1428–1432 (1992); Fell et al., *J. Immunol.* 146:2446–2452(1991) (said references incorporated by reference in their entireties).

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the hinge region, $CH_1$ domain, $CH_2$ domain, and $CH_3$ domain or any combination of whole domains or portions thereof. The polypeptides of the present invention may be fused or conjugated to the above antibody portions to increase the in vivo half life of the polypeptides or for use in immunoassays using methods known in the art. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See e.g., U.S. Pat. Nos. 5,336,603, 5,622,929, 5,359,046, 5,349,053, 5,447,851, 5,112,946; EP 0 307 434, EP 0 367 166; WO 96/04388, WO 91/06570; Ashkenazi et al., *PNAS* 88:10535–10539 (1991); Zheng et al., *J. Immunol.* 154:5590–5600 (1995); and Vil et al., *PNAS* 89:11337–11341(1992) (said references incorporated by reference in their entireties).

Moreover, the Ckβ7 polypeptides can be fused to marker sequences, such as a peptide which facilitates purification of Ckβ7. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., *Cell* 37:767 (1984).)

As described above, the polypeptides of the present invention may be fused to immunoglobulins, or portions thereof. Chemokine fusion proteins have desirable characteristics such as increased half-life in vivo and the ability to cross the placenta. Chemokine-Ig fusions and chemokine fusions with other heterologous proteins can retain the ability to bind and activate or inhibit activation of the chemokine receptor (Challita-Eid, P. M. et al. *AIDS Res. Hum. Retroviruses* 14:1617 (1998); Challita-Eid, P. M. et al., *J. Immunol.* 161:3729 (1998); Biragyn, A. et al., *Nature Biotech.* 17:253 (1999)).

The chemokine-heterologous protein fusion may be direct or may be via a linker or spacer sequence such as $(Ser-Gly^4)^3$ (Challita-Eid, P. M. et al., *J. Immunol.* 161:3729 (1998) or NDAQAPKS (Biragyn, A. et al., *Nature Biotech.* 17:253

(1999). As is well-known in the art, the portions of a Ig variable and/or constant region may also be linked by a sequence such as (Gly$_3$Ser)$_3$GlySer (Biragyn, A. et al., *Nature Biotech.* 17:253 (1999)).

Ckβ7 activity of the fusion protein can be assayed as described above and in the Examples, or as described in the references in this Section.

Thus, any of these above fusions can be engineered using the Ckβ7 polynucleotides or the polypeptides.

The present invention will be further described with reference to the following examples; however, it is to be understood that the present invention is not limited to such examples.

EXAMPLE 1

Bacterial Expression and Purification of Ckβ-7 Polypeptides

The DNA sequence encoding for Ckβ-7 ATCC No. 75675 was initially amplified using PCR oligonucleotide primers corresponding to the 5' sequences of the processed Ckβ-7 protein (minus the signal peptide sequence). Additional nucleotides corresponding to BamHI and XbaI were added to the 5' and 3' sequences respectively. The 5' oligonucleotide primer has the sequence: 5'-TCAGGATCCGCA-CAAGTTGGTACCAAC-3' (SEQ ID NO:6), which contains a BamHI restriction enzyme site followed by 18 nucleotides of Ckβ-7 coding sequence starting from the presumed terminal amino acid of the processed protein codon. The 3' sequence: 5'-CGCTCTAGAGTAAAAC-GACGGCCAGT-3' (SEQ ID NO:7) contains complementary sequences to an XbaI site.

Nucleic acid molecules encoding the following specific Ckβ-7 N-terminal deletion mutants are also amplified using the following 5' primers, each of which contains a BamHI restriction enzyme site followed by 18 nucleotides of Ckβ-7 coding sequence.

```
Amino acids 22-89 in SEQ ID NO:2:
5'-TCAGGATCCCAAGTTGGTACCAACAAA-3'.    (SEQ ID NO:8)

Amino acids 23-89 in SEQ ID NO:2:
5'-TCAGGATCCGTTGGTACCAACAAAGAG-3'.    (SEQ ID NO:9)

Amino acids 24-89 in SEQ ID NO:2:
5'-TCAGGATCCGGTACCAACAAAGAGCTC-3'.    (SEQ ID NO:10)
```

The restriction enzyme sites correspond to the restriction enzyme sites on the bacterial expression vector pQE-9 (Qiagen, Inc., Chatsworth, Calif.). pQE-9 encodes antibiotic resistance (Amp), a bacterial origin of replication (ori), an IPTG-regulatable promoter operator (P/O), a ribosome binding site (RBS), a 6-His tag and restriction enzyme sites. pQE-9 was then digested with BamHI and XbaI The amplified sequences were ligated into pQE-9 and were inserted in frame with the sequence encoding for the histidine tag and the RBS. The ligation mixture was then used to transform *E. coli* strain 15/rep4 available from Qiagen. M15/rep4 contains multiple copies of the plasmid pREP4, which expresses the lacI repressor and also confers kanamycin resistance (Kan$^r$). Transformants are identified by their ability to grow on LB plates and ampicillin/kanamycin resistant colonies were selected. Plasmid DNA was isolated and confirmed by restriction analysis. Transformants are identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 µg/ml) and Kan (25 µg/ml). The O/N culture is used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3 to 4 hours. Cells were then harvested by centrifugation. The cell pellet was solubilized in the chaotropic agent 6 M Guanidine HCl. After clarification, solubilized Ckβ-7 was purified from this solution by chromatography on a Nickel-Chelate column under conditions that allow for tight binding by proteins containing the 6-His tag. Hochuli, E. et al., *J. Chromatography* 411:177–184 (1984). Ckβ-7 (95% pure) was eluted from the column in 6.0 M guanidine HCl pH 5.0 and for the purpose of renaturation adjusted to 3.0 M guanidine HCl, 100 mM sodium phosphate, 10 mM glutathione (reduced) and 2 mM glutathione (oxidized). After incubation in this solution for 12 hours the protein was dialyzed to 10 mM sodium phosphate.

EXAMPLE 2

Expression of Ckβ-7 in Mammalian Cells

Most of the vectors used for the transient expression of Ckβ-7 protein in mammalian cells should carry the SV40 origin of replication. This allows the replication of the vector to high copy numbers in cells (e.g., COS cells) which express the T antigen required for the initiation of viral DNA synthesis. Any other mammalian cell line can also be utilized for this purpose.

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular signals can also be used (e.g., human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human HeLa, 283, H9 and Jurkart cells, mouse NIH3T3 and C127 cells, Cos 1, Cos 7 and CV1, African green monkey cells, quail QC1-3 cells, mouse L cells and Chinese hamster ovary cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) is a useful marker to develop cell lines that carry several hundred or even several thousand copies of the gene of interest. Another useful selection marker is the enzyme glutamine synthase (GS) (Murphy et al., *Biochem. J.* 227:277–279 (1991); Bebbington et al., *Bio/Technology*

10: 169–175 (1992)). Using these markers, the mammalian cells are grown in selective medium and the cells with the highest resistance are selected. These cell lines contain the amplified gene(s) integrated into a chromosome. Chinese hamster ovary (CHO) cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530(1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Expression of Recombinant Ckβ-7 in COS cells. The expression of plasmid, CMV-Ckβ-7 HA is derived from a vector pcDNAI/Amp (Invitrogen) containing: 1) SV40 origin of replication, 2) ampicillin resistance gene, 3) *E. coli* replication origin, 4) CMV promoter followed by a polylinker region, a SV40 intron and polyadenylation site. A DNA fragment encoding the entire Ckβ-7 precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (Wilson, H., et al., *Cell* 37:767 (1984)). The infusion of HA tag to the target protein allows easy detection of the recombinant protein with an antibody that recognizes the HA epitope.

The plasmid construction strategy is described as follows:
The DNA sequence ATCC No. 75675 encoding for Ckβ-7 is constructed by PCR using two primers: the 5' primer:

5'-GGAAAGCTTATGAAGGGCCTTGCAGCTGCC-3' (SEQ ID NO:11) contains a HindIII site followed by 22 nucleotides of Ckβ-7 coding sequence starting from the initiation codon; the 3' sequence:

5'-CGCTCTAGATCAAGCGTAGTCTGGGACGTCGTAT GGGTAGGCATTCAGCTTCAGGTC-3' (SEQ ID NO:12) contains complementary sequences to XbaI site, translation stop codon, HA tag and the last 19 nucleotides of the Ckβ-7 coding sequence (not including the stop codon). Therefore, the PCR product contains a HindIII site, Ckβ-7 coding sequence followed by HA tag fused in frame, a translation termination stop codon next to the HA tag, and an XbaI site. The PCR amplified DNA fragment and the vector, pcDNAI/Amp, are digested with HindIII and XbaI restriction enzyme and ligated. The ligation mixture is transformed into *E. coli* strain SURE (available from Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant Ckβ-7, COS cells are transfected with the expression vector by DEAE-DEXTRAN method. (J. Sambrook, E. Fritsch, T. Maniatis, Molecular Cloning: A Laboratory Manual, Cold Spring Laboratory Press, (1989)). The expression of the Ckβ-7-HA protein is detected by radiolabelling and immunoprecipitation method. (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media are then collected and cells are lysed with detergent (RIPA buffer (150 mM NaCl, 1% NP-40, 0.1% SDS, 1% NP-40, 0.5% DOC, 50 mM Tris, pH 7.5). (Wilson, H., et al., *Cell* 37:767 (1984)). Both cell lysate and culture media are precipitated with a HA specific monoclonal antibody. Proteins precipitated are analyzed on 15% SDS-PAGE gels.

Cloning and Expression in CHO Cells. The vector pC1 is used for the expression of Ckβ-7 protein. Plasmid pC1 is a derivative of the plasmid pSV2-dhfr (ATCC Accession No. 37146). Both plasmids contain the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, J. Biol. Chem. 253:1357–1370, Hamlin, J. L. and Ma, C. 1990, Biochem. et Biophys. Acta, 1097:107–143, Page, M. J. and Sydenham, M. A. 1991, Biotechnology Vol. 9:64–68). Cells grown in increasing concentrations of MTX develop resistance to the drug by overproducing the target enzyme, DHFR, as a result of amplification of the DHFR gene. If a second gene is linked to the DHFR gene it is usually co-amplified and overexpressed. It is state of the art to develop cell lines carrying more than 1,000 copies of the genes. Subsequently, when the methotrexate is withdrawn, cell lines contain the amplified gene integrated into the chromosome(s).

Plasmid pC1 contains for the expression of the gene of interest a strong promoter of the long terminal repeat (LTR) of the Rouse Sarcoma Virus (Cullen, et al., Molecular and Cellular Biology, March 1985:438–4470) plus a fragment isolated from the enhancer of the immediate early gene of human cytomegalovirus (CMV) (Boshart et al., *Cell* 41:521–530, 1985). Downstream of the promoter are the following single restriction enzyme cleavage sites that allow the integration of the genes: BamHI, followed by the 3' intron and the polyadenylation site of the rat preproinsulin gene. Other high efficient promoters can also be used for the expression, e.g., the human P-actin promoter, the SV40 early or late promoters or the long terminal repeats from other retroviruses, e.g., HIV and HTLVI. For the polyadenylation of the mRNA other signals, e.g., from the human growth hormone or globin genes can be used as well.

Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC1 is digested with the restriction enzyme BamHI and then dephosphorylated using calf intestinal phosphates by procedures known in the art. The vector is then isolated from a 1% agarose gel.

The DNA sequence encoding Ckβ-7, ATCC No. 75675, is amplified using PCR oligonucleotide primers corresponding to the 5' and 3' sequences of the gene:

The 5' primer has the sequence:

```
                                        (SEQ ID NO:13)
5' AAAGGA TCC GCC ACC ATG AAG GGC CTT GCA AGC 3'
      BamHI    KOZAK
``` containing the underlined BamHI restriction enzyme site and a portion of the sequence encoding the Ckβ-7 protein of FIG. 1 (SEQ ID NO:1). Inserted into an expression vector, as described below, the 5' end of the amplified fragment encoding human Ckβ-7 provides an efficient signal peptide.

An efficient signal for initiation of translation in eukaryotic cells, as described by Kozak, M., *J. Mol. Biol.* 196:947–950 (1987) is appropriately located in the vector portion of the construct.

The 3' primer has the sequence:

```
                                         (SEQ ID NO:14)
5' AAAGGA TCC TCA GGC ATT CAG CTT CAG 3'
      BamHI   Stop
``` containing the Asp718 restriction site followed by nucleotides complementary to a portion of the Ckβ-7 coding sequence set out in FIG. 1 (SEQ ID NO:1), including the stop codon.

The amplified fragments are isolated from a 1% agarose gel as described above and then digested with the endonucleases BamHI and Asp718 and then purified again on a 1% agarose gel.

The isolated fragment and the dephosphorylated vector are then ligated with T4 DNA ligase. *E. coli* HB101 cells are then transformed and bacteria identified that contained the plasmid pC1 inserted in the correct orientation using the restriction enzyme BamHI. The sequence of the inserted gene is confirmed by DNA sequencing.

Transfection of CHO-DHFR-cells. Chinese hamster ovary cells lacking an active DHFR enzyme are used for transfection. Five μg of the expression plasmid C1 are cotransfected with 0.5 μg of the plasmid pSVneo using the lipofecting method (Felgner et al., supra). The plasmid pSV2-neo contains a dominant selectable marker, the gene neo from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) and cultivated from 10–14 days. After this period, single clones are trypsinized and then seeded in 6-well petri dishes using different concentrations of methotrexate (25 nM, 50 nM, 100 nM, 200 nM, 400 nM). Clones growing at the highest concentrations of methotrexate are then transferred to new 6-well plates containing even higher concentrations of methotrexate (500 nM, 1 μM, 2 μM, 5 μM). The same procedure is repeated until clones grow at a concentration of 100 μM.

The expression of the desired gene product is analyzed by Western blot analysis and SDS-PAGE.

EXAMPLE 3

Assays of Ckβ-7 Deletion Mutant Functional Activities

The Ckβ-7 deletion mutant polypeptides may be assays for functional activities using a variety of methods. Several of these methods are set out below.

Calcium Flux Assay. Ckβ-7 polypeptides of the invention may be tested for their ability to induce a $Ca^{++}$ flux in various cell types according to the following assay.

Monocytes, lymphocytes and neutrophils are isolated from donor blood buffy coats. Eosinophils and basophils are purified from fresh venous blood of healthy volunteers.

Changes in the cytosolic free $Ca^{++}$ concentration ($[Ca^{++}]i$), and enzyme release are monitored following loading of the cells with Fura-2 acetoxymethyl ester (0.2 mmol per 106 cells) by incubation for 20 min. at 37° C. in medium containing 136 mM NaCl, 4.8 mM KCl, 1 mM $CaCl_2$, 5 mM glucose, and 20 mM Hepes, pH 7.4 and 1 to 1,000 nM Ckβ-7 polypeptide alone, or in comparison with MCP-3, MCP-4, RANTES, Eotaxin, Eotaxin-2 or MIP-1α. Loaded cells are washed and resuspended in the same medium (106 cells/ml) and $[Ca^{++}]i$-related fluorescence changes are observed. Receptor desensitization is tested by monitoring $[Ca^{++}]i$ changes after sequential chemokine stimulation.

A similar method for measuring intracellular calcium concentrations is disclosed in Nibbs et al., *J. Biol. Chem.* 272:12495–12504, which is incorporated herein by reference in its entirety.

In Vitro Chemotaxis Assay. Cells are washed and labeled with calcein-AM and distributed into the upper chamber of a 96 well disposable chemotaxis plate (NeuroProbe, Cabin John, Md.) separated by a polycarbonate filter (5–8 m pore size; PVP free). Lymphocytes are allowed to migrate for 90 minutes (eosinophils for 3 hours) and then the number of migrated cells (both attached to the filter as well as in the bottom chamber) are counted using a Cytofluor II fluorescence plate reader (Perseptive Biosystems). Values for the chemotaxis assay are reported as the chemotactic index which refers to the fold induction above background observed with the various factors used.

Other CCR3 assays. International Patent Application Serial No. PCT/US97/17103 discloses a number of assays for determining interaction between the CCR3 receptor and its ligands. Such assays are representative of the state of the art. Such assays find use herein for determining the biological activity of Ckβ-7 polypeptides. Accordingly, PCT/US97/17103 is incorporated herein by reference in its entirety.

EXAMPLE 4

CCR3 Antagonism by the β-Chemokine MIP4, a Property Strongly Enhanced by an Amino-terminal Alanine-methionine Swap Movement of leukocytes from the blood into and through tissues is essential for these cells to perform their function of protecting the body from invasion by micro-organisms and other pathogens. This process requires the complex interplay between adhesion molecules and chemotactic factors and is able to rapidly respond upon detection of infection or damage (Springer, T. A., *Cell* 76:301 (1994)). Aberrations in this process are associated with many diseases such as autoimmunity, chronic inflammatory disease and allergy, pathologies characterized by the inappropriate influx and activation of leukocytes within tissues.

Whilst many molecules are able to stimulate leukocyte chemotaxis, it has become clear that chemokines play a central role in regulating haemopoietic cell movement both during the establishment of inflammation and immune responses, and also during immune surveillance and the development of the blood system (Rollins, B. J., *Blood* 90:909 (1997); Baggiolini, M., *Nature* 392:565 (1998); Nagasawa, T., et al., *Nature* 382:635 (1996)). Recently, these proteins have also been implicated in the biology of other cell types, such as haemopoietic stem cells, microglia, neurons and endothelial cells (Graham, G. J., et al., *Nature* 344:442 (1990); Harrison, J. K, et al., *Proc. Natl. Acad. Sci. USA* 95:10896 (1998); Tachibana, K., et al., *Nature* 393:591 (1998); Zou, Y.-R., et al., *Nature* 393:595 (1998)). Chemokines are divided into four subfamilies on the basis of the position of the first two cysteine residues of the mature protein. Thus, in the CC or β chemokines, these two residues are juxtaposed, whilst the CXC (or α) and the $CX_3C$ chemokines, have one and three amino acids, respectively, between these two cysteines. The C subfamily only has a single cysteine at this position.

The biological effects of these proteins are mediated by interactions with a family of cell surface heptahelical G-protein coupled receptors present on the target cells (Murphy, P. M., *Cytokine and Growth Factor Reviews* 7:47 (1996); Premack, B. A. and Schall, T. J., *Nature Med.* 2:1174 (1996)). These receptors are often highly promiscuous, interacting with many chemokine ligands, usually from within the same chemokine subfamily. This has lead to the receptors being named CCR, CXCR, $CX_3CR$ or XCR, depending upon which ligand subfamily is recognized (Murphy, P. M., *Cytokine and Growth Factor Reviews* 7:47 (1996); Premack, B. A. and Schall, T. J., *Nature Med.* 2:1174 (1996); Imai, T., et al., *Cell* 91:521 (1997); Yoshida, T., et al., *J. Biol. Chem.* 273:16551 (1998)). Interest in these proteins has intensified in the last couple of years with the demonstration that many chemokine receptors, in particular CXCR4 and CCR5, and to a lesser extent CCR3, act as coreceptors for the entry of HIV into its target cells and that the ligands for these receptors interfere with virus entry (Clapham, P. R., *Trends Cell Biol.* 7:264 (1997); Cairns, J. S. and D'Souza, M. P., *Nature Med.* 4:563 (1998)).

Parasite and allergen-induced inflammation is characterized by infiltration of eosinophils, T lymphocytes of the Th2 type and occasional basophils into tissue (Weller, P. F., *N. Engl. J. Med.* 324:1110 (1991); Teixeira, M. M., et al., *Trends in Pharm. Sci.* 16:418 (1995)). The CC, or β, chemokine receptor CCR3, is specifically expressed on these cell types, and plays a central role in their infiltration (Uguccioni, M., et al., *J. Clin. Invest.* 100:1137 (1997); Sallusto, F., et al., *Science* 277:2005 (1997); Sallusto, F., et al., *J. Exp. Med.* 187:875 (1998); Gerber, B. O., et al., *Curr. Biol.* 7:836 (1997); Bonecchi, R., et al., *J. Exp. Med.* 187:129 (1998)). In response to local production of the CCR3 ligands eotaxin, eotaxin-2, MCP3, MCP4 or RANTES, these cells can adhere to, and migrate through, blood vessel endothelium (Ponath, P. D., et al., *J. Exp. Med.* 183:2437 (1996); Daugherty, B. L., et al., *J. Exp. Med.* 183:2349 (1996); Garcia-Zapeda, E. A., et al., *J. Immunol.* 157:5613 (1996); Uguccioni, M., et al., *J. Exp. Med.* 183:2379 (1996); Forssmann, U., et al., *J. Exp. Med.* 185:2171 (1997); Kitayama, J., et al., *J. Clin. Invest.* 101:2017 (1998)). Subsequent granule release by eosinophils and basophils brings about changes in tissue structure and integrity, often causing irreversible damage (Weller, P. F., *N. Engl. J. Med.* 324:1110 (1991)). Therapies that block cellular recruitment may be of benefit in allergic diseases, such as asthma and contact dermatitis, and specific targeting of the CCR3 receptor may have considerable advantage over drugs that indiscriminately inhibit leukocyte chemotaxis, such as steroids. In fact, deletion of eotaxin by homologous recombination, the use of neutralizing antibodies to this ligand or injection of a chemokine receptor antagonist, Met-RANTES, has been demonstrated to ameliorate allergic inflammation in a variety of animal models (Rothenberg, M. E., et al., *J. Exp. Med.* 185:785 (1997); Teixeira, M. M., et al., *J. Clin. Invest.* 100:1657 (1997); Matthews, A. N., et al., *Proc. Natl. Acad. Sci. USA* 95:6273 (1998); Gonzalo, J.-A., et al., *J. Exp. Med.* 188:157 (1998); Elsner, J., et al., *Eur. J. Immunol.* 27:2892 (1997)).

The present inventors have generated a potent CCR3 antagonist, called Met-Ckβ7, a modified form of the β-chemokine referred to herein as MIP4 and alternatively called PARC, DCCK1, or AMAC1 (Adema, G. J., et al., *Nature* 387:713 (1997); Hieshima, K., et al., *J. Immunol.* 159:1140 (1997); Wells, T. N. C. and Peitsch, M. C., *J. Leukocyte Biol.* 61:545 (1997); Kodelja, V., et al., *J. Immunol.* 160:1411 (1998)). Met-Ckβ7 is significantly more potent as a CCR3 antagonist than Met-RANTES or aminooxypentane (AOP)-RANTES (Elsner, J., et al., *Eur. J. Immunol.* 27:2892 (1997); Proudfoot, A. E. I., et al., *J. Biol. Chem.* 271:2599 (1996); Simmons, G., et al., *Science* 276:276 (1997); Mack, M., et al., *J. Exp. Med.* 187:1215 (1998)), and unlike these proteins shows no detectable partial agonist activity. Furthermore, Met-Ckβ7 is highly specific for CCR3. This novel antagonist is able to completely inhibit eosinophil chemotaxis at concentrations as low as 1 nM. Surprisingly, the unmodified MIP4 protein (which has been reported to act as a naïve T cell chemoattractant acting through a currently unidentified receptor) also exhibits CCR3 antagonistic activity in our assays, although it is considerably less potent than Met-Ckβ7. Therefore, the modifications in Met-Ckβ7, and specifically the introduction of a methionine in place of an alanine at the extreme amino terminus, enhance a property present in the unmodified protein. Interestingly, MIP4 is able to inhibit CCR3-mediated eosinophil chemotaxis at concentrations that are physiologically relevant. The significance of this observation, with respect to the biological function of MIP4, is discussed.

Materials and Methods

Met-Ckβ7 Production and Other Chemokines. The coding sequence of Ckβ7 was amplified from an adult human lung cDNA library using primers to remove the signal peptide and replace the N-terminal alanine seen in the mature protein with a methionine. The nucleotides encoding the C-terminus were altered to encode either LKLMPEA (Met-Ckβ7*) or LKLNA (Met-Ckβ7) and both cDNAs were cloned into the pQE7 expression vector. The resulting plasmids were transformed into *E. coli* M15 Rep4 host cells, grown at 37° C. in LB containing ampicillin and kanamycin and protein induced by incubation with 0.2 mM IPTG for 3 h. Cells were harvested, resuspended in ET buffer (75 mM EDTA, 50 mM Tris pH 7.5) and lysed by passing twice through a microfluidizer (Microfluidics, Newton, Mass.) at 6000–8000 psi. NaCl was added to 0.5M and the sample centrifuged at 7000 g for 15 min. The pellet was washed in ET plus 0.5M NaCl and centrifuged at 7000 g again for 15 min. These partially purified inclusion bodies were resuspended in 1.5M guanidine hydrochloride, 50 mM Tris (pH 7.4), incubated overnight at 4° C. and then centrifuged at 30000 g. The supernatant was mixed vigorously for 30 min at 4° C. in 20 volumes of 150 mM NaCl, 2 mM EDTA, 50 mM sodium acetate (pH 4.5) and left for 60 h at 4° C. This solution was clarified using a 0.16 μm sterile filter (Filtron, Pall Corporation, N.Y.) and chromatographed over a strong cation exchange column (Poros HS-50, Perspective Biosystems, Framingham, Mass.) prewashed with 6 column volumes of 250 mM NaCl, 40 mM sodium acetate (pH 5.5). Bound protein was eluted using 3 to 5 column volumes of a stepwise gradient of 0.5M, 1M, 1.5M NaCl in 40 mM sodium acetate (pH 5.5). Positive fractions were pooled, diluted 3-fold with 40 mM sodium acetate (pH 5.5) and applied to a set of strong anion (Poros HQ-50) and weak cation (Poros CM-20) exchange columns in tandem mode prewashed with 150 mM NaCl, 40 mM sodium acetate (pH 5.5). The CM-20 column was eluted with a 10–20 column volume linear gradient of 0.15–1.25 M NaCl, fractions analyzed through SDS-PAGE and positive fractions combined. The proteins were greater than 95% pure by SDS-PAGE and reverse phase HPLC analysis. Peptide sequencing revealed the expected amino-termini of MQVGTNKEL.

Met-RANTES and aminooxypentane (AOP)-RANTES were produced as previously described (Proudfoot, A. E. I., et al., *J. Biol. Chem.* 271:2599 (1996); Simmons, G., et al., *Science* 276:276 (1997)). All other chemokines, including MIP4, were purchased from Peprotech, London, UK or R&D Systems, Abingdon, UK.

Cell Culture and Preparation. HOS cells stably expressing human CCR3 were the generous gift of Dr. Nathaniel Landau (Salk Institute, La Jolla, Calif.) and were maintained in DMEM plus 10% fetal calf serum, antibiotics and 1 µg/ml puromycin (Sigma, Poole, Dorset, UK). HEK293 cells stably expressing human CCR1, 2, 3, and 5 were generated by transfection with Transfectam (Promega, Southampton, UK), according to manufacturers protocols, and selection in 0.8 mg/ml G418. CHO cells expressing human D6 are described elsewhere (Nibbs, R. J. B., et al., *J. Biol. Chem.* 272:32078 (1997)).

Eosinophils were purified from single donor leukopaks (American Red Cross, Baltimore, Md.) as previously described (Hansel, T. T., et al., *J. Immunol. Methods* 145:105 (1991)), or by purifying granulocytes from peripheral blood and selecting those cells that were CD16 negative using MACS technology (Miltenyi Biotec, Bergisch, Germany). Eosinophils were greater than 90% pure as assessed on stained cytospun preparations.

Mononuclear cells were purified from samples of peripheral blood (Western Infirmary, Glasgow). Blood containing at least 100 U/ml of preservative-free heparin was diluted 1:4 with PBS containing 0.6% ACD (Acid Citrate Dextrose, Sigma). This was layered over Ficoll (1.077 density) in a ratio of 3:1 and centrifuged at 400 g for 30 min at 22° C. Mononuclear cells were removed from the interface and washed three times in PBS/0.6% ACD.

To purify and activate T cells, heparinized blood was collected from healthy donors, separated over ficoll-hypaque and washed four times in PBS. These cells were then adhered to plastic for 2 hrs at 37° C. in RPMI/10% FCS and the non-adherent cells then stimulated for five days in 4 µg/ml concanavalin A (Sigma). Cells were then repurified over ficoll-hypaque as before and stimulated at 106 cells/ml in 20 U/ml IL2 (Peprotech) for 7–14 days. CD3+ and CD45RA+ cells were purified by positive selection from PBMCs (isolated as described above) using anti-CD3 and anti-RA antibodies, respectively, and MACS technology. Purity was >95% as determined by FACS analysis.

$Ca^{2+}$ Flux Assays. HOS-hCCR3 cells were harvested by trypsinization, washed in SR buffer (136 mM NaCl, 4.8 mM KCl, 5 mM glucose, 1 mM $CaCl_2$, 0.025% BSA, 25 mM HEPES (pH 7.6)) then incubated in SR with 1 mM Fura-2-AM (Sigma) for 1 h at 37° C. Cells were then washed in SR, resuspended in SR to ~2×10$^6$ cells/ml, and 2 ml incubated at 37° C. in a continuously stirred cuvette in a Perkin-Elmer LS50 Spectrometer. After 2 min, fluorescence emission was recorded every 100 msec (340 nm ($\lambda_{ex}$); 500 nm ($\lambda_{em}$)) for 20 to 40 secs, agonist or antagonist added to a defined concentration and fluorescence recorded every 100 msec for a further 80 to 120 secs. For agonist dose-response experiments, all ligands were compared to a full dose-response performed with human eotaxin to avoid day-to-day experimental variation. Peripheral blood mononuclear cells and lymphocytes were also loaded and analysed using this procedure.

Eosinophils were loaded for 30 min at room temperature with 2 µM Fura-2-AM in a modified SR buffer (125 mM NaCl, 5 mM KCl, 0.5 mM glucose, 1 mM $MgCl_2$, 1 mM $CaCl_2$, 0.025% BSA, 20 mM HEPES (pH 7.4)), washed and resuspended at 106 cells/ml. Intracellular $Ca^{2+}$ changes from a 2 ml sample were measured in a F2000 spectrometer (Hitachi Instruments Inc., San Jose, Calif.) by monitoring fluorescence emission at 37° C. over time (340 nm and 380 nm ($\lambda_{ex}$); 510 nm ($\lambda_{em}$)).

In all experiments, the distance from the baseline emission to the highest point of the flux was calculated and converted to a percentage of the maximal flux induced in each experiment.

Eosinophil Chemotaxis Assays. Purified eosinophils were washed with HBSS/BSA (Hank's Balanced Salt Solution with 0.1% BSA) and resuspended in this medium at 5×10$^6$ cells/ml with 1 µM calcein-AM (MolecularProbes, Eugene, Oreg.). After 30 min at 37° C., cells were washed in HBSS/BSA, resuspended to 5×10$^6$ cells/ml, and 20 µl of this suspension dispensed into each upper chamber of a 96-well chemotaxis plate filter (Neuro Probe, Cabin John, Md.). Different concentrations of agonist were added to the bottom chamber, and antagonist added to either the bottom chamber, the top and bottom chamber, or neither chamber. Cells were allowed to migrate for 3 hrs through the polycarbonate filter (8 µM pores; polyvinylpyrolidone-free) between the two chambers, and the number of migrated cells in the bottom chamber quantitated using a fluorescence plate reader (Cytofluor PerSeptive Biosystems). The ratio between the number of cells migrated in the presence of agonist and the number of cells migrated in buffer alone is defined as the chemotaxis index.

Radioinodination of Met-Ckβ7*. Five µg of Met-Ckβ7* was incubated in 50 µl of PBS containing 100 µg of IODO-GEN (Pierce, Rockford, Ill.) and 1 mCi Na $^{125}$I (DuPont NEN) for 15 min on ice. The reaction was then run down a D-Salt Excellulose Desalting Column (40–100 micron) and 0.5 ml fractions taken with PBS. 2 µl aliquots of the fractions were counted in a Beckman Gamma 5500B counter and positive fractions combined.

Eosinophil $^{125}$I-Chemokine Binding Assay. 2×10$^5$ purified eosinophils were placed in each well of a 96 well plate in binding buffer (1 mM $CaCl_2$, 5 mM $MgCl_2$, 0.5% BSA, 0.05% sodium azide, 50 mM Hepes (pH 7.5)). Iodinated chemokine (final concentration of 0.1 nM $^{125}$I-eotaxin or $^{125}$I-MCP4, specific activity 2200 Ci/mmol (NEN, Boston, Mass.)) was added in the absence or presence of unlabeled chemokines to a final volume of 100 µl. The binding reaction was incubated for 60 min at room temperature, the cells then transferred to filter plates (Silent Screen with loprodyne membrane (Nalge Nunc, Rochester, N.Y.)) pretreated with 0.1% polyethylenimine, and washed three times with binding buffer containing 0.5M NaCl. The plates were dried and counted after addition of 50 µl of liquid scintillant in each well. Each point was done in triplicate and is presented as the mean of these results with standard error. For experiments with $^{125}$I-Met-Ckβ7*, 2×10$^5$ eosinophils were incubated in DMEM plus 10% fetal calf serum, 0.4% sodium azide and 20 mM Hepes (pH 7.6) containing 45 nM $^{125}$I-Met-Ckβ7* and with or without 500 nM unlabeled chemokine as competitor for 2 hrs at room temperature. Cells were then washed twice with ice cold PBS and counted in a Beckman Gamma 5500B counter. Each point was done in triplicate and is presented as the mean of these results with standard error.

Results

Met-Ck#7* Production. The present inventors previously amplified a cDNA clone, Ckβ7 or MIP4, from an adult human lung cDNA library (See U.S. Pat. No. 5,504,003). Predictive algorithms suggest that the putative signal peptide will be cleaved from this protein to leave an amino-terminus beginning AQVGT-, although QVGT- may also be produced. Production in insect cells generated a protein with AQVGTNKEL- at the N-terminus, although variable amounts of truncated variants starting TNKEL- or NKEL- were also found in our studies. To produce this protein in vitro with a homogeneous N-terminus, a cDNA construct, Met-Ckβ7*, was generated in which the region encoding the signal sequence was removed and the nucleotides encoding the alanine residue at the putative N-terminus of the mature protein were replaced with an ATG encoding methionine. This cDNA was transformed into bacteria and the protein purified (see Materials and Methods). Sequencing revealed the expected N-terminus of MQVGT-.

The C-terminus encoded by the Met-Ckβ7* clone differs from that encoded by the Ckβ7/MIP4 clone. The predicted C-terminus of Met-Ckβ7* ends -LKLMPEA, whereas the Ckβ7/MIP4 C-terminus ends -LKLNA. During the production and analysis of Met-Ckβ7*, sequences identical to the Ckβ7/MIP4 predicted amino acid sequence were described by others and named PARC, DCCK1 and AMAC1 (Adema, G. J., et al., Nature 387:713 (1997); Hieshima, K., et al., J. Immunol. 159:1140 (1997); Wells, T. N. C. and Peitsch, M. C., J. Leukocyte Biol. 61:545 (1997); Kodelja, V., et al., J. Immunol. 160:1411 (1998)). The difference at the C-terminus between Met-Ckβ7* and Ckβ7/MIP4/PARC/DCCK1/AMAC1 (hereafter "Ckβ7") may be due to allelic variation or a frameshift mutation introduced during amplification and cloning. Concerning the expected N-terminus, two of the publications reported that the mature protein, when expressed in COS or insect cells, begins AQVGT-(Adema, G. J., et al., Nature 387:713 (1997); Hieshima, K., et al., J. Immunol. 159:1140 (1997)), consistent with the observations of the present inventors.

To assess the impact of the C-terminal sequence variation, the present inventors made a protein, Met-Ckβ7, engineered to contain a methionine in place of the first N-terminal alanine, but with the C-terminus of Ckβ7 (-LKLNA) rather than that of Met-Ckβ7* (-LKLMPEA). As with Met-Ckβ7*, this protein was produced in a bacterial expression system.

Importantly, in all assays tested, Met-Ckβ7 and Met-Ckβ7* exhibited identical activity showing that the C-terminal differences have no affect on the properties described (data not shown). The data shown in this Example uses the protein with the C-terminus of LKLMPEA, and it is referred to hereafter as Met-Ckβ-7*, with the "*" indicating that it contains a C-terminal sequence distinct from Ckβ7/MIP4/PARC/DCCK1/AMAC1.

Figure 21E:
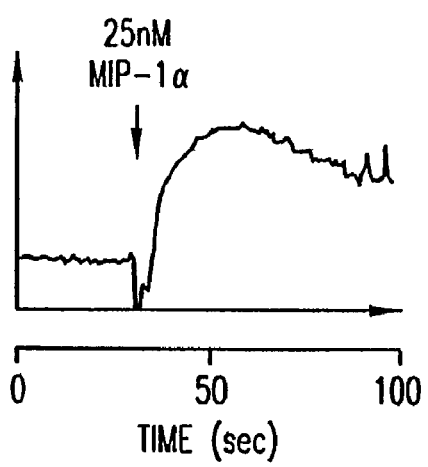
Figures 1, 21E:
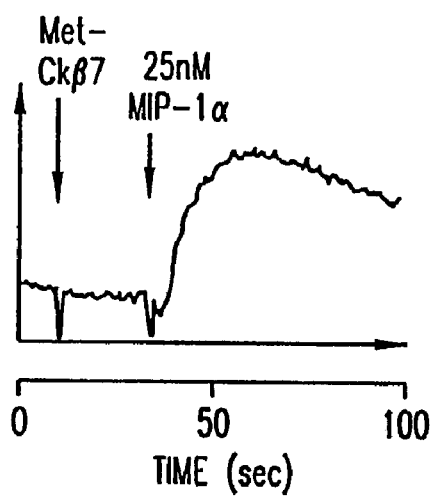

Activity of Met-Ckβ7* on Chemokine Receptors. This protein was tested for its ability to elicit a $Ca^{2+}$ flux through chemokine receptors CCR1, 2, 3 and 5 expressed in heterologous cells. At concentrations up to 1 μM, no signaling was detectable through these receptors whilst known ligands signaled efficiently (data not shown). Also, 700 nM Met-Ckβ7* was unable to displace any $^{125}$I-MIP1α from the promiscuous D6 chemokine receptor (Nibbs, R. J. B., et al., J. Biol. Chem. 272:32078 (1997)) in binding assays on CHO cells expressing this receptor (not shown). However, with HOS cells stably transfected with human CCR3 (HOS-CCR3 cells), pre-treatment with 500 nM Met-Ckβ7* prevented subsequent $Ca^{2+}$ fluxes induced with known CCR3 agonists (FIGS. 21A–D). This activity was not seen on CCR1, 2 or 5, even when CCR3 ligands MCP4 (that also signals through CCR2) or RANTES (that also signals through CCR1 and 5) were used as agonists (not shown). To further assess the specificity of this antagonist, mononuclear cells and CD3+ T-lymphocytes were isolated from human peripheral blood, and ConA/IL-2-activated T cells were also prepared (see Materials and Methods), and Met-Ckβ7* was tested for whether it could inhibit $Ca^{2+}$ fluxes induced with a range of chemokines. None of the human chemokines that gave a $Ca^{2+}$ flux in these various cell types (MGSA, IL8, SDF1, RANTES, MIP1α, MIP1β, MCP1, fractalkine, MIP3α, MIP3β, SLC, IP-10) were antagonized by 500 nM Met-Ckβ7* (not shown). Further, no agonist activity was detected with Met-Ckβ7* in these assays. One example of these experiments using peripheral blood mononuclear cells, and human MIP1α as the agonist, is shown in FIGS. 21E–E-1. It is of note that unmodified MIP4 gave no detectable $Ca^{2+}$ flux in any of the cell types tested (not shown).

Figure 22:
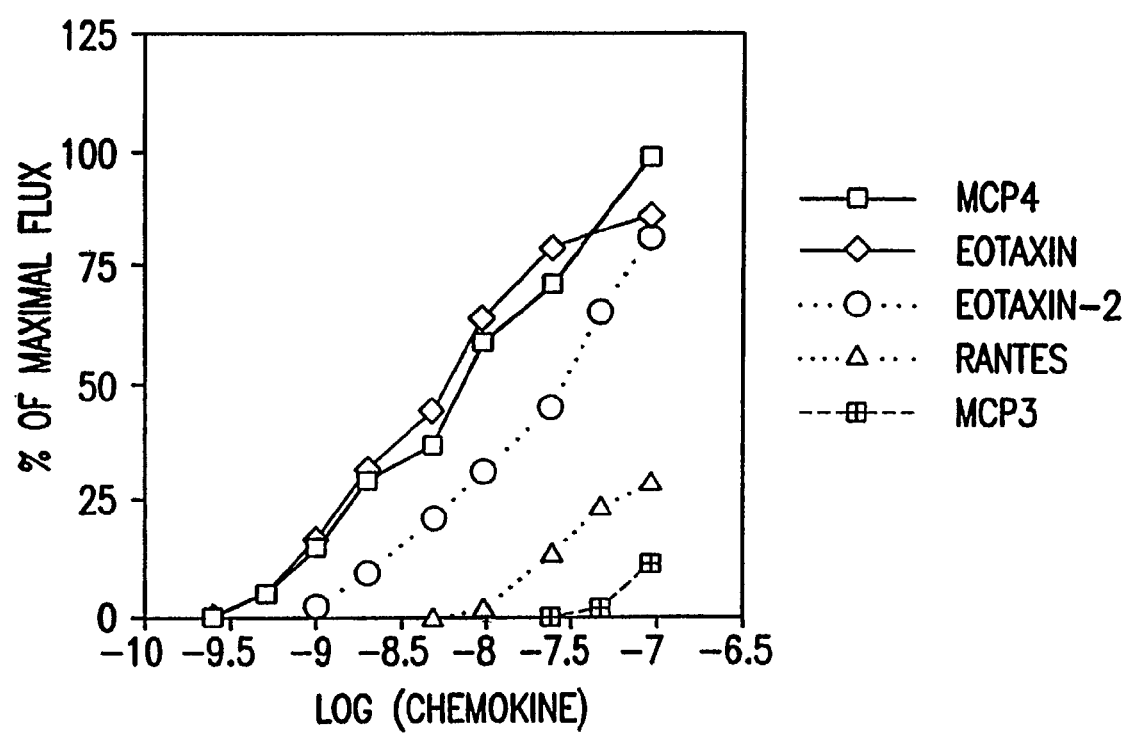
FIG. 22 shows that CCR3 ligands signal with different potencies into HOS-CCR3 cells. Dose-response curves for ligand-induced calcium ion fluxes into Fura-2 loaded HOS cells expressing human CCR3. Each flux was compared to a maximal defined as that induced with 100 nM MCP4.
Figure 23A:
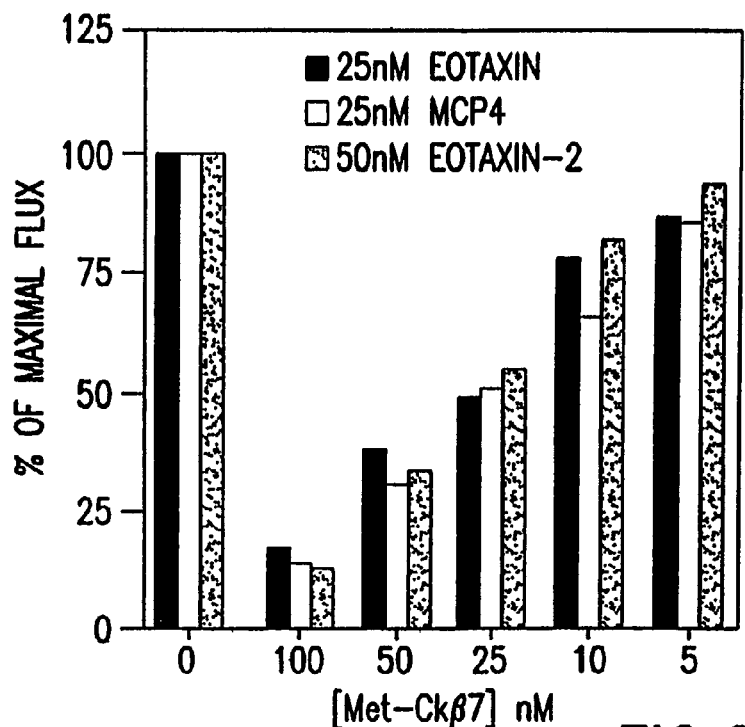
FIGS. 23A–23B show that Met-Ckβ-7* is a potent antagonist of signaling through CCR3 into HOS-CCR3 cells or eosinophils. The peak of calcium ion flux (detected by Fura2 fluorescence) induced by a set amount of agonist in the presence of a range of Met-Ckβ-7* concentrations, is represented as a percentage of the flux induced in the absence Met-Ckβ-7*. (A) HOS-CCR3 cells, (B) purified human eosinophils. Arrows indicate where no $CA^{2+}$ flux was detectable.

Met-Ckβ7* is a Potent CCR3 Antagonist. Next, the present inventors defined the potency of this CCR3 antagonist. Several chemokines are known to act as CCR3 agonists and Met-Ckβ7* may exert differential effects on these ligands. Thus, the potency of these known CCR3 agonists was compared by dose-response experiments examining $Ca^{2+}$ flux into HOS-CCR3 cells at different concentrations of ligand. As shown in FIG. 22, eotaxin, eotaxin-2 and MCP4 induced strong signals through CCR3 in the low nanomolar range and above, with slight $CA^{2+}$ fluxes still detectable at 1 nM. RANTES was much less potent, and MCP3 gave a barely detectable signal even at 100 nM. The number of CCR3 receptors on the HOS-CCR3 cells is low (not shown), and may account for the relative ineffectiveness of RANTES and MCP3 in these assays. Dose-response experiments were then performed using a range of concentrations of Met-Ckβ7* to examine its effect on a subsequent $Ca^{2+}$ flux induced with a concentration of CCR3 agonist known to give a strong signal. As shown in FIG. 23A, half maximal inhibition of a $Ca^{2+}$ flux induced with 25 nM eotaxin or MCP4, or 50 nM eotaxin-2, was seen at approximately 25 nM Met-Ckβ7*. With 100 nM RANTES, which only produces a weak signal into HOS-CCR3 cells, 50% inhibition was observed at a slightly lower concentration of Met-Ckβ7* (~10 nM) (not shown).

Figure 24A:
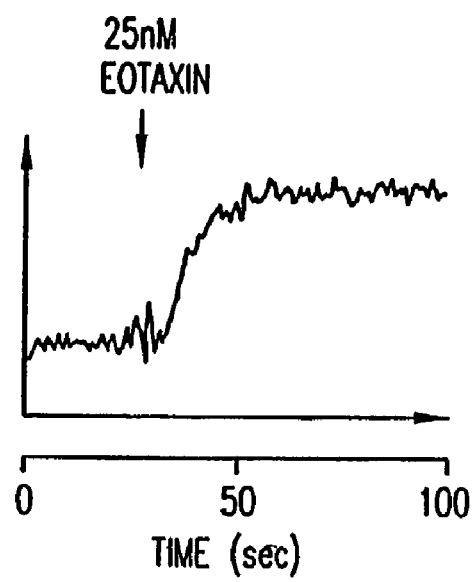
FIGS. 24A–24D show that Met-Ckβ-7* more effectively inhibits CCR3-mediated $Ca^{2+}$ flux than Met- or AOP-RANTES. Fura-2-loaded HOS-CCR3 cells stimulated at 37° C. with 25 nM eotaxin (panel A), or with 25 nM eotaxin in the presence of 100 nM Met-RANTES (panel B), 100 nM AOP-RANTES (panel C), or 100 nM Met-Ckβ7* (panel D). Fluorescence emission is recorded every 0.1 sec for 100 sec (340 nm ($\lambda_{ex}$) 500 nm ($\lambda_{em}$)).
Figure 24B:
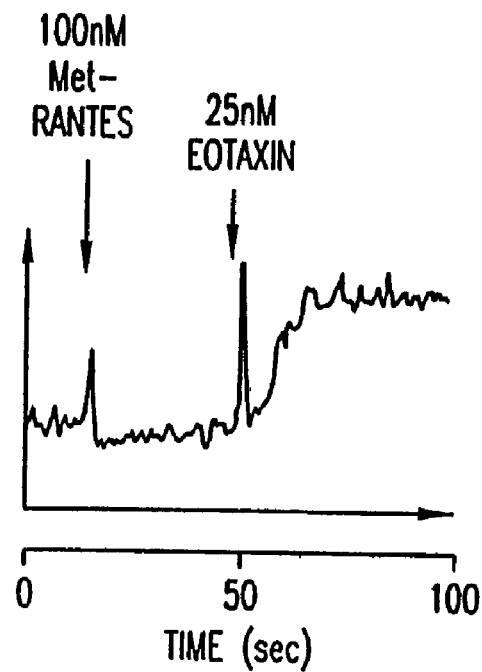
Figure 24C:
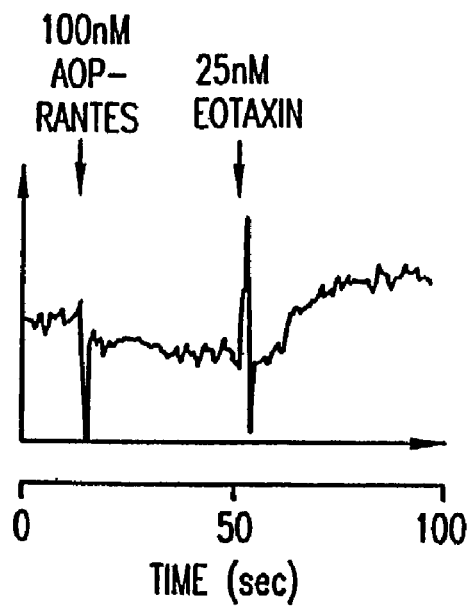
Figure 24D:
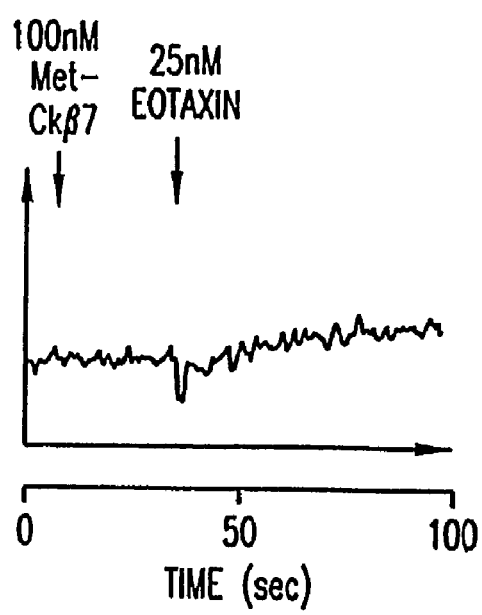

HOS-CCR3 signaling assays were also used to examine the activity of two known RANTES receptor antagonists, Met-RANTES and AOP-RANTES (Proudfoot, A. E. I., et al., J. Biol. Chem. 271:2599 (1996); Simmons, G. et al., Science 276:276 (1997)) in comparison with Met-Ckβ7*. Met-RANTES used at 100 nM only slightly reduced a 25 nM eotaxin-induced flux, whilst 100 nM AOP-RANTES was more potent, reducing this flux by ~35% (FIG. 24). In contrast, 100 nM Met-Ckβ7* reduced a 25 nM eotaxin-induced flux by ~85% (FIG. 24D). It is of note that Met-RANTES and AOP-RANTES are able to induce a moderate $Ca^{2+}$ flux through CCR1 and CCR5 and that AOP-RANTES is in fact fully active on CCR5 in these assays (Mack, M., et al., J. Exp. Med. 187:1215 (1998)). It has been shown that AOP-RANTES (100 nM), and to a lesser degree Met-RANTES, have weak $Ca^{2+}$ mobilizing activity on CHO-CCR3 and L1.2-CCR3 transfectants, although this activity was never superior to 50% of that induced by RANTES. Neither Met- nor AOP-RANTFS (at 100 nM) mobilize calcium in the HOS-CCR3 transfectants (FIG. 24), perhaps due to the low receptor level on these cells, but AOP-RANTES at higher concentrations (250 nM) does induce very weak, but detectable, $Ca^{2+}$ fluxes into these cells (data not shown). To the contrary, Met-Ckβ7* shows no CCR3 signaling potential in $Ca^{2+}$ flux assays with CCR3 transfectants or eosinophils, even at 1 μM.

Figure 23B:
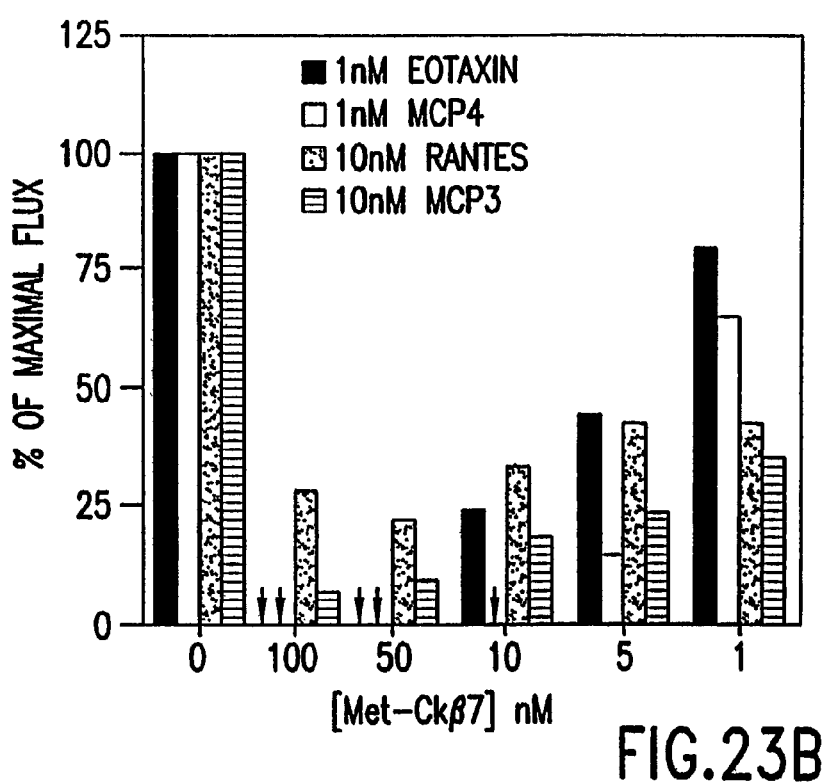

Met-Ckβ7* Can Prevent Eosinophil $Ca^{2+}$ Flux Induced by CCR3 Agonists. Met-Ckβ7* was next examined for its ability to antagonize the function of CCR3 agonists on eosinophils. The concentration of CCR3 agonist required to induce detectable $Ca^{2+}$ fluxes into these cells was considerably lower than that required with the CCR3-transfected HOS cells used above, most likely due to higher receptor levels on eosinophils. Met-Ckβ7* completely blocked $Ca^{2+}$ fluxes into eosinophils induced by 1 nM eotaxin or MCP4, at 50 nM or 10 nM of Met-Ckβ7*, respectively (FIG. 23B). When 10 nM RANTES or MCP3 were used as agonists, whilst low concentrations of Met-Ckβ7* (1 nM) caused a profound reduction in the magnitude of the $Ca^{2+}$ flux, complete antagonism was not achieved even with 100 nM Met-Ckβ-7*. This is explained by the presence of CCR1 on these cells acting as a receptor for RANTES and MCP3, further demonstrating that Met-Ckβ7* does not abrogate signaling through this receptor.

Figure 25A:
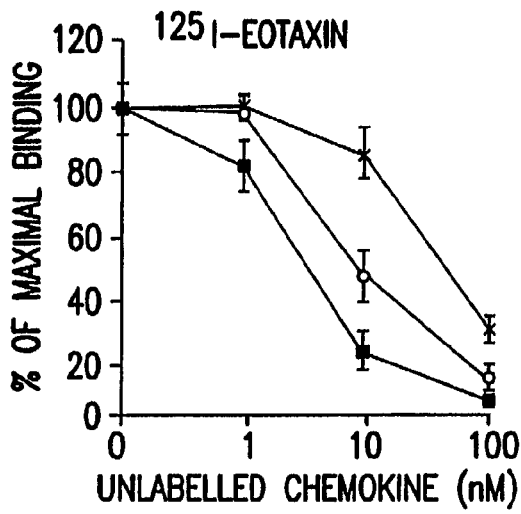
FIGS. 25A–25C show the displacement of $^{125}$I-labeled eotaxin, MCP4 or Met-Ckβ7* from eosinophils. (A and B) $2\times10^5$ purified eosinophils were incubated for 60 min at room temperature in azide-containing binding buffer with 0.1 nM $^{125}$I-eotaxin (Panel A) or 0.1 nM $^{125}$I-MCP4 (Panel B) plus a range of concentrations of unlabeled chemokine, either Met-Ckβ7* (filled squares), MCP4 (crosses) or eotaxin (open circles). After washing with binding buffer containing 0.5M NaCl, the percentage of radio-iodinated ligand remaining bound was calculated compared to assays in which no unlabeled chemokine was added. Each point is the mean of three identical incubations and standard error is included. (C) $2\times10^5$ purified eosinophils were incubated for 2 hrs at room temperature in azide-containing binding buffer with 45 nM $^{125}$I-Met-Ckβ7* plus 500 nM of the various unlabeled chemokines indicated at the bottom of the graph. Cells were washed twice with PBS and remaining $^{125}$I-Met-Ckβ7* bound was counted. Results are the mean of three identical incubations represented as a percentage of the binding seen in the absence of competitor, and standard error is included.
Figure 25B:
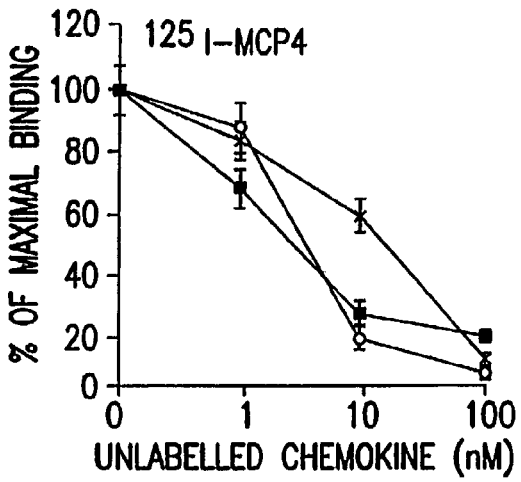
Figure 25C:
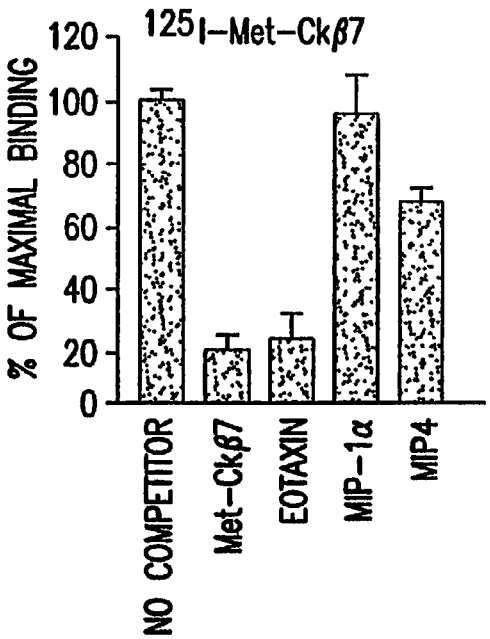

Analysis Using Radio-iodinated Ligands Suggest a Direct Interaction Between Met-Ckβ7* and CCR3. The present inventors next examined the ability of unlabelled Met-Ckβ7* to displace radioiodinated MCP4 or eotaxin from CCR3, in comparison with unlabelled eotaxin and MCP4. The low level expression of CCR3 on the transfected HOS-CCR3 cells necessitated the use of eosinophils in these assays. FIG. 25A shows that Met-Ckβ7* more efficiently displaced $^{125}$I-eotaxin from these cells ($IC_{50}$~6 nM) than unlabeled eotaxin ($IC_{50}$ ~10 nM) or MCP4 ($IC_{50}$~60 nM). Eotaxin and Met-Ckβ7* behaved similarly ($IC_{50}$ ~5 nM), and were more effective than unlabelled MCP4 ($IC_{50}$~25 nM) in displacing $^{125}$I-MCP4 (FIG. 25B). Thus, Met-Ckβ7* competes with known CCR3 agonists for binding to CCR3. This is due to a direct interaction between the antagonist and the receptor. The present inventors demonstrated this directly by radiolabelling Met-Ckβ7* and showing binding to eosinophils that could be competed by unlabeled Met-Ckβ7* and eotaxin, but not by unlabeled MIP-1α (FIG. 25C). Interestingly, unlabeled MIP4 was also able to displace some of the labeled Met-Ckβ7* from the surface of eosinophils showing that it too interacts weakly with this receptor (FIG. 25C and see below). Subsequent experiments with radiolabelled eotaxin also demonstrated heterologous displacement by MIP4, although this ligand was considerably less effective than Met-Ckβ7* (data not shown).

Figure 26A:
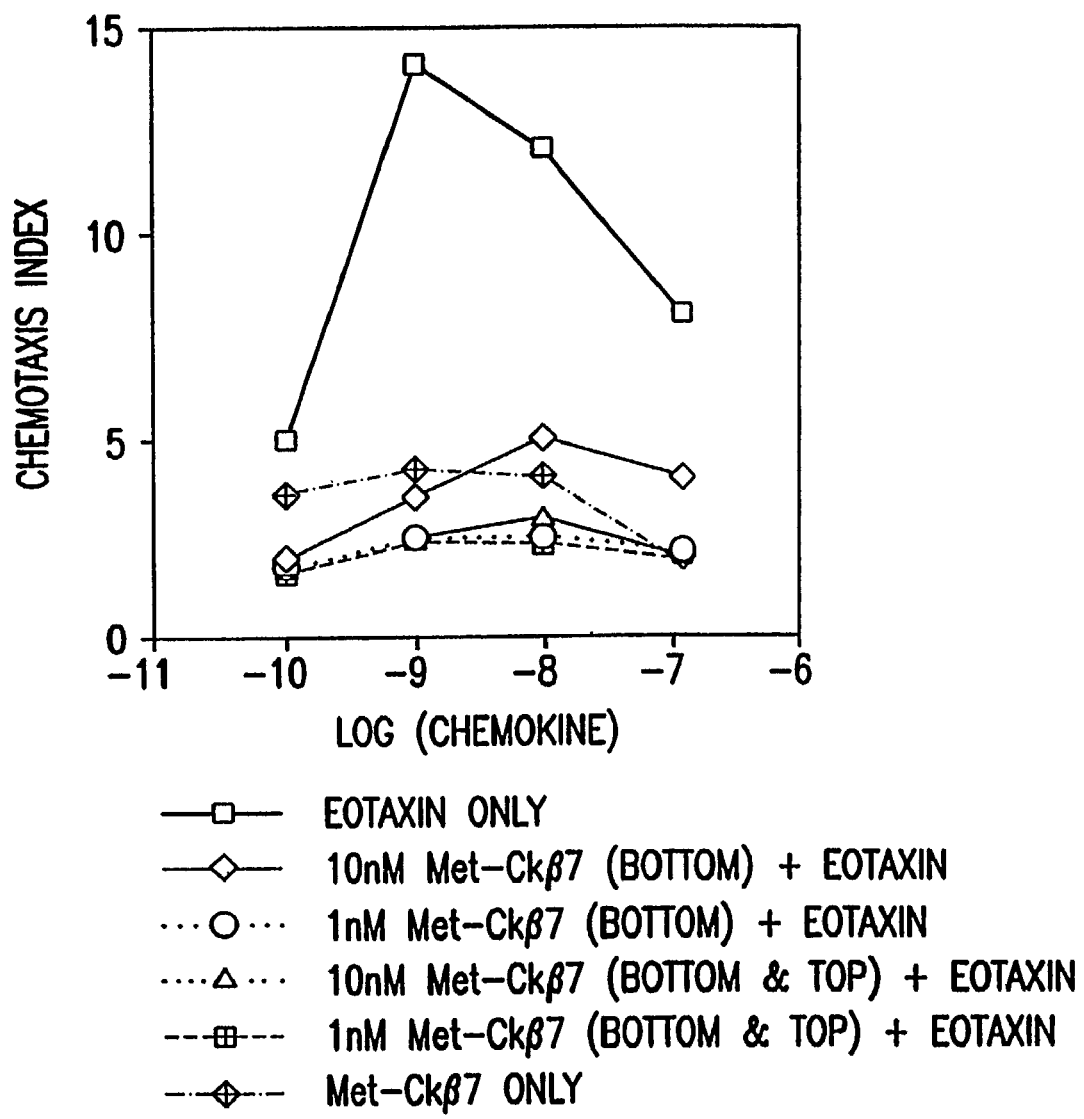
FIGS. 26A–26C show that Met-Ckβ7* inhibits eotaxin-induced chemotaxis of human eosinophils from three donors. Chemotaxis assays were performed for 3 hrs with a range of eotaxin (or Met-Ckβ7*) concentrations. In some experiments, Met-Ckβ7* was added at 1 or 10 nM to the bottom chamber, or the top and bottom chambers, of the chemotaxis well as indicated in the key. Chemotaxis index is calculated as the ratio of cells migrated in the test sample compared to cells migrated in buffer alone. (A) Donor A, (B) Donor B, (C) Donor C.
Figure 26B:
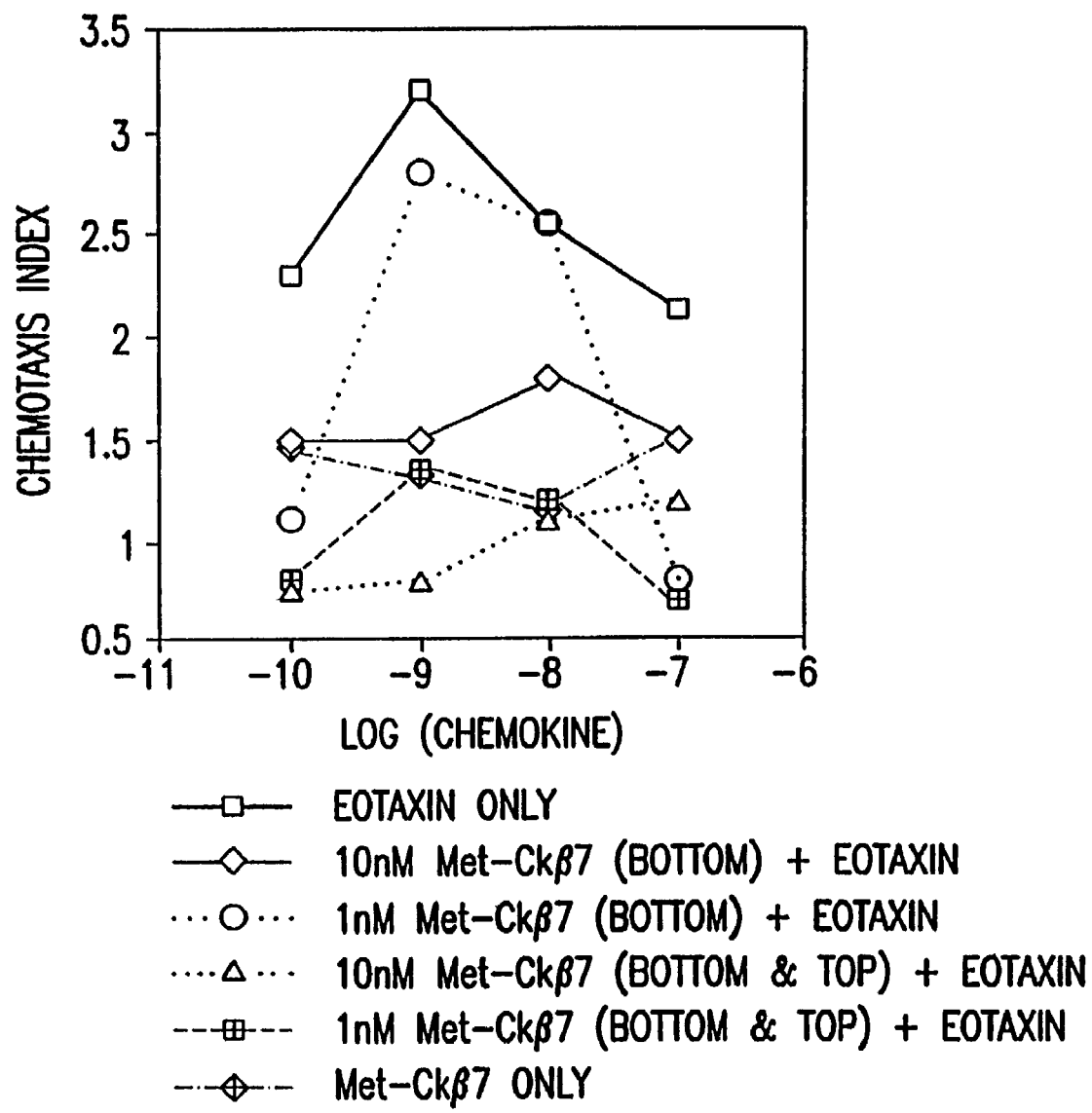
Figure 26C:
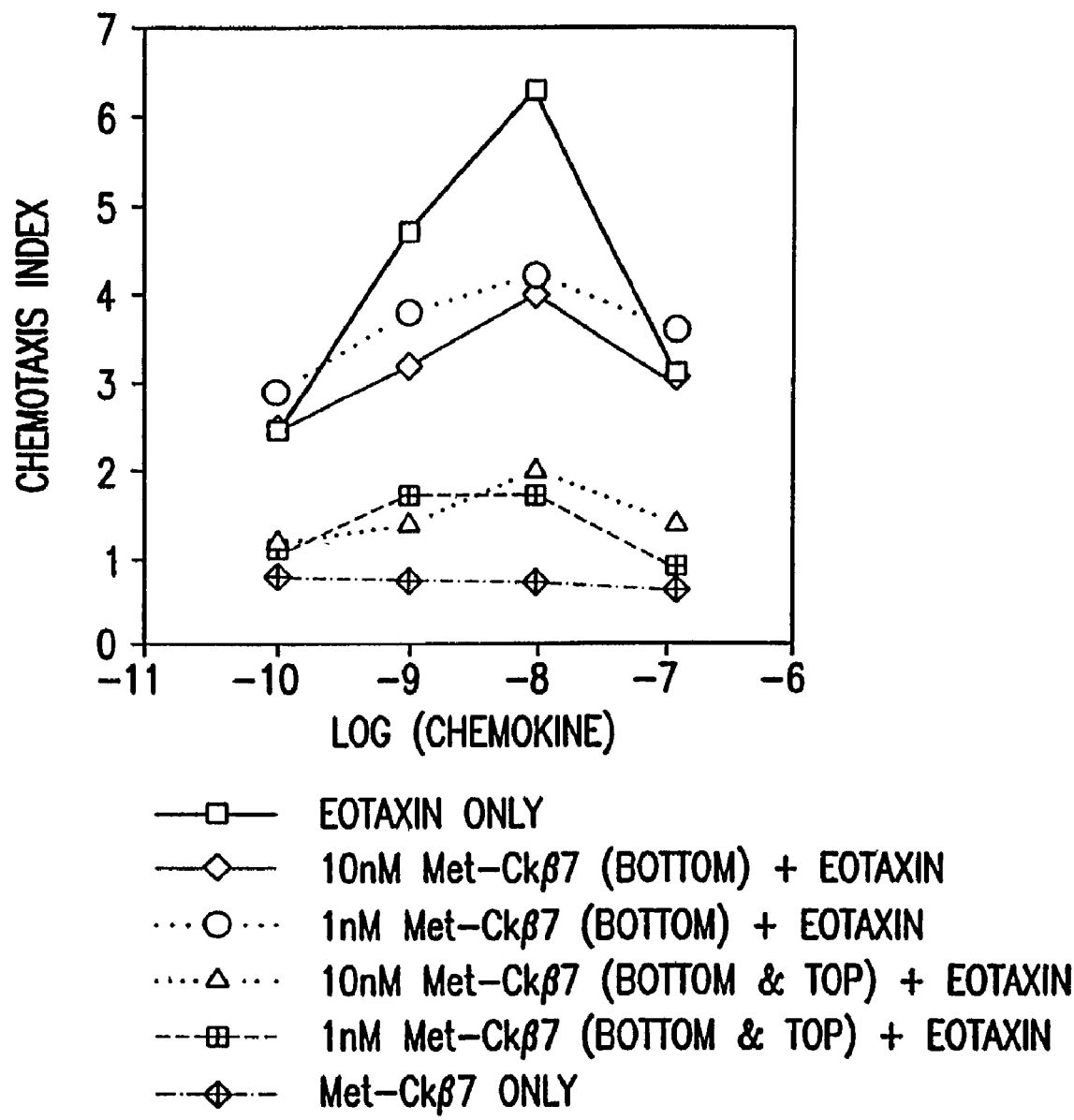
Figure 27A:
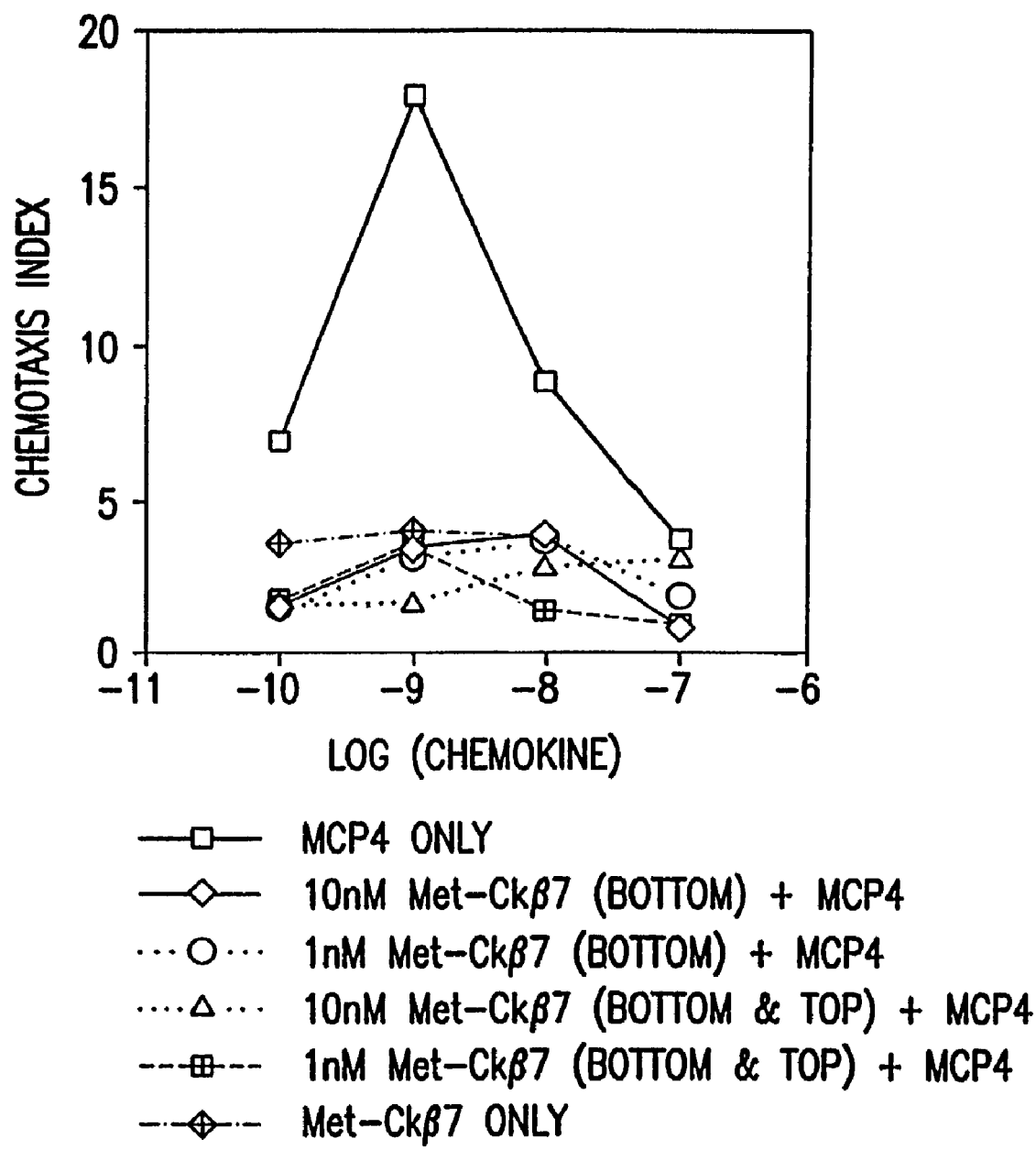
FIGS. 27A–27C show that Met-Ckβ7* inhibits MCP4-induced chemotaxis of human eosinophils from three donors. Chemotaxis assays were performed for 3 hrs with a range of MCP4 (or Met-Ckβ7*) concentrations. In some experiments, Met-Ckβ7* was added at 1 or 10 nM to the bottom chamber, or the top and bottom chambers, of the chemotaxis well as indicated in the key. Chemotaxis index is calculated as the ratio of cells migrated in the test sample compared to cells migrated in buffer alone. (A) Donor A, (B) Donor B, (C) Donor C.
Figure 27B:
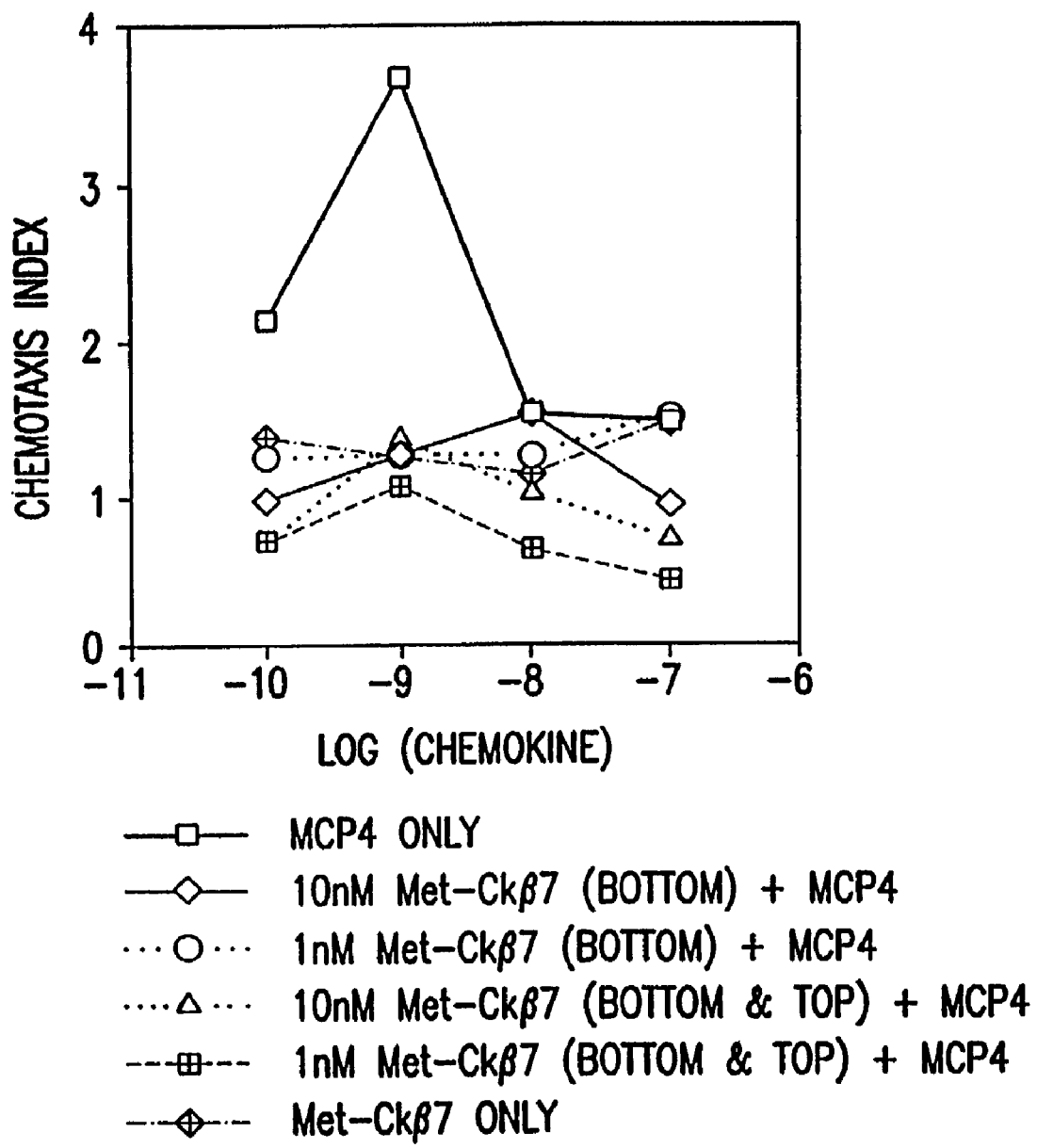
Figure 27C:
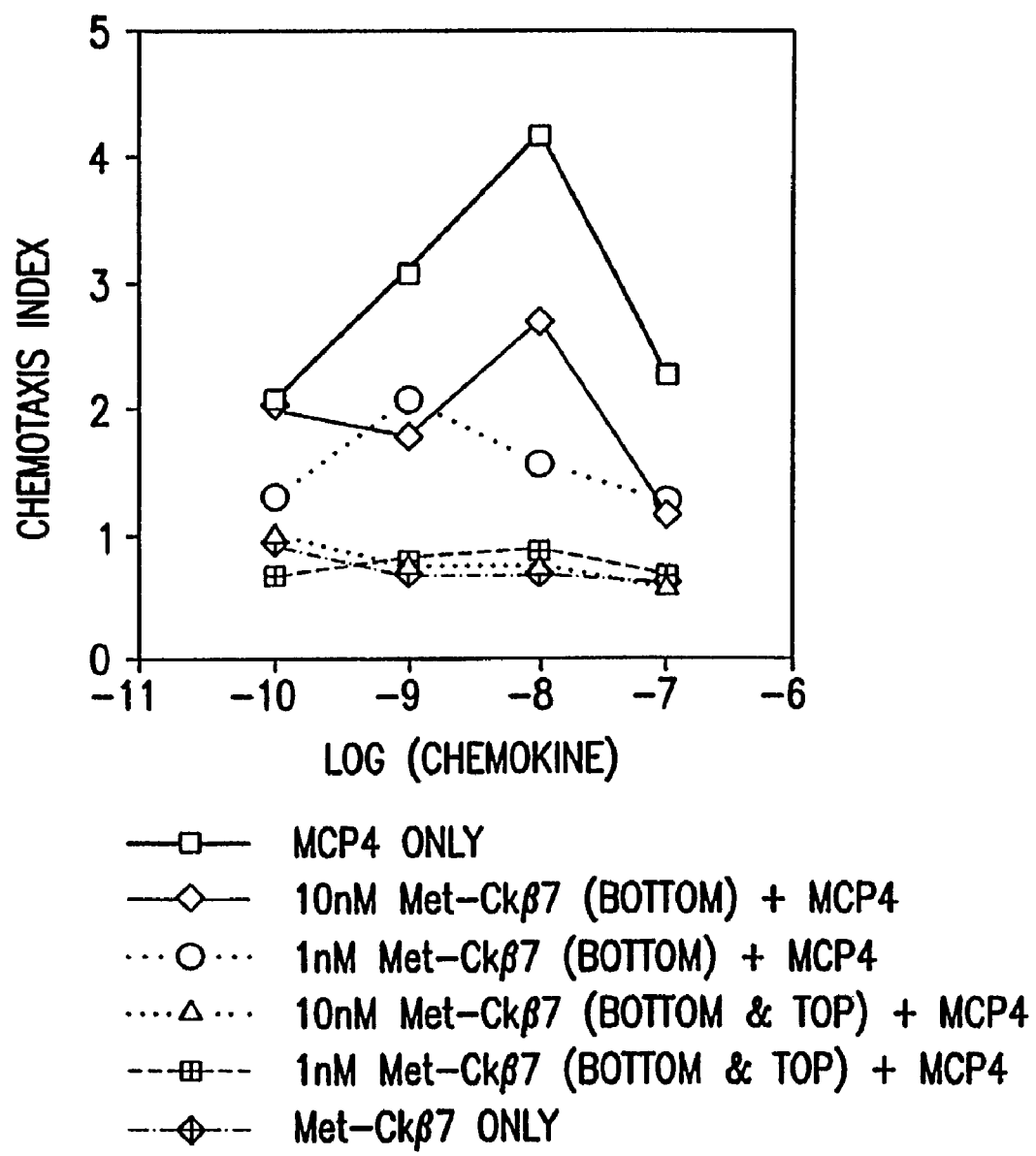
Figure 28A:
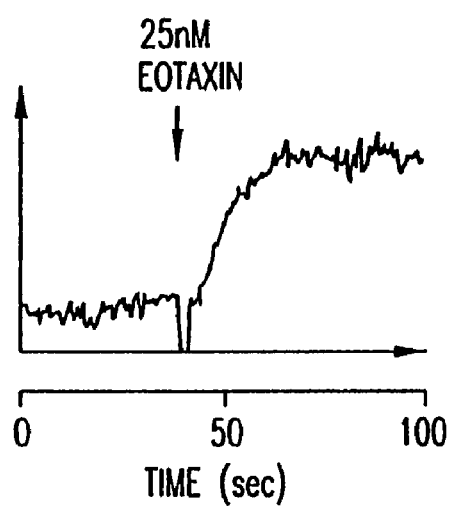
FIGS. 28A–28B show that unmodified MIP4 inhibits eotaxin-induced signaling through CCR3. Fura-2-loaded HOS-hCCR3 cells stimulated at 37° C. with 25 nM eotaxin in the absence (A) or presence (B) of 250 nM MIP4. Fluorescence emission is recorded every 0.1 sec for 100 sec (340 nm ($\lambda_{ex}$); 500 nm ($\lambda_{em}$)).
Figure 28B:
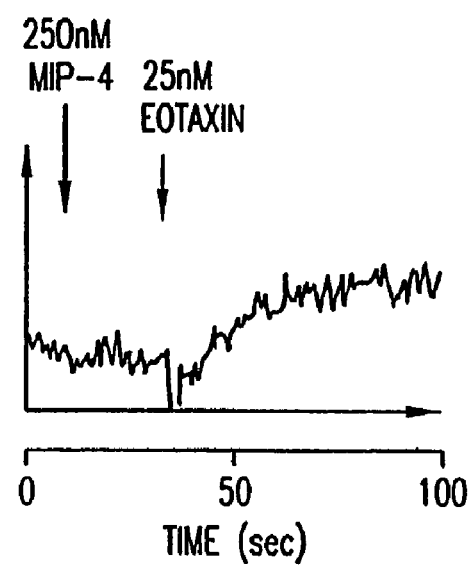

Met-Ckβ7* Prevents Eosinophil Chemotaxis Induced by CCR3 Ligands. To further test the potency of the antagonist on eosinophil function, chemotaxis assays were performed with purified human eosinophils. Results from three donors are shown in FIGS. 26 and 27. Eotaxin and MCP4 induced chemotaxis of eosinophils most effectively when 1 nM or 10 nM of the chemokine was present in the lower well, although the maximal chemotaxis index achieved varied considerably between donors. These concentrations are considerably lower than those required to induce maximal $Ca^{2+}$ fluxes through CCR3 into HOS-CCR3 cells or eosinophils (FIG. 23A and not shown), indicating that low receptor occupancy is optimal for chemotaxis induction. Met-Ckβ7* was unable to stimulate chemotaxis over the concentrations tested, but was able to efficiently block eotaxin- and MCP4-mediated chemotaxis. The potency of the antagonist in these assays varied slightly between donors; thus, whilst 1 nM was sufficient to inhibit the eotaxin and MCP4-induced chemotaxis of eosinophils from donor A, this was not sufficient to prevent eotaxin-induced chemotaxis of donor B's eosinophils unless Met-Ckβ7* was added to the top and the bottom wells of the assay chamber. With donor C, addition of Met-Ckβ7* to the bottom compartment of the well only reduced eosinophil chemotaxis in response to eotaxin and MCP4, while addition of the antagonist to both upper and lower chambers reduced chemotaxis to baseline levels (see Discussion). These data demonstrate however, that Met-Ckβ7* is a potent inhibitor of eosinophil chemotaxis induced by CCR3 ligands, with low nanomolar concentrations being sufficient to completely abrogate cell migration.

Figure 29A:
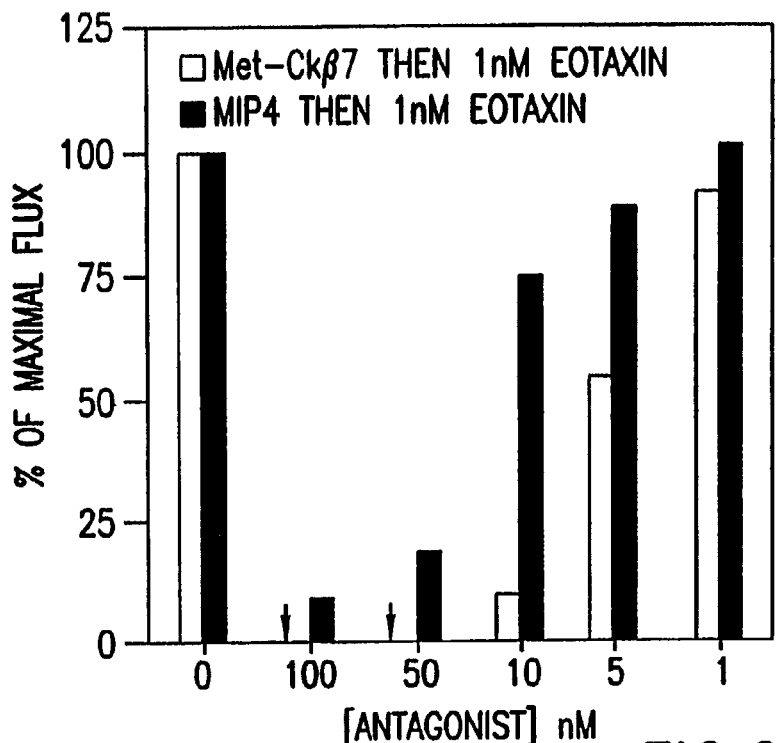
FIGS. 29A–29B show that MIP4 is a less potent antagonist of CCR3 signaling into eosinophils than Met-Ckβ7*. The peak of calcium ion flux into human eosinophils (detected by Fura-2 fluorescence), induced by a set amount of agonist in the presence of a range of MIP4 or Met-Ckβ7* concentrations, is represented as a percentage of the flux induced in the absence of antagonist. Arrows indicate where no $CA^{2+}$ flux was detectable. Agonist used is (A) 1 nM eotaxin, or (B) 1 nM MCP4, as indicated in the key.
Figure 29B:
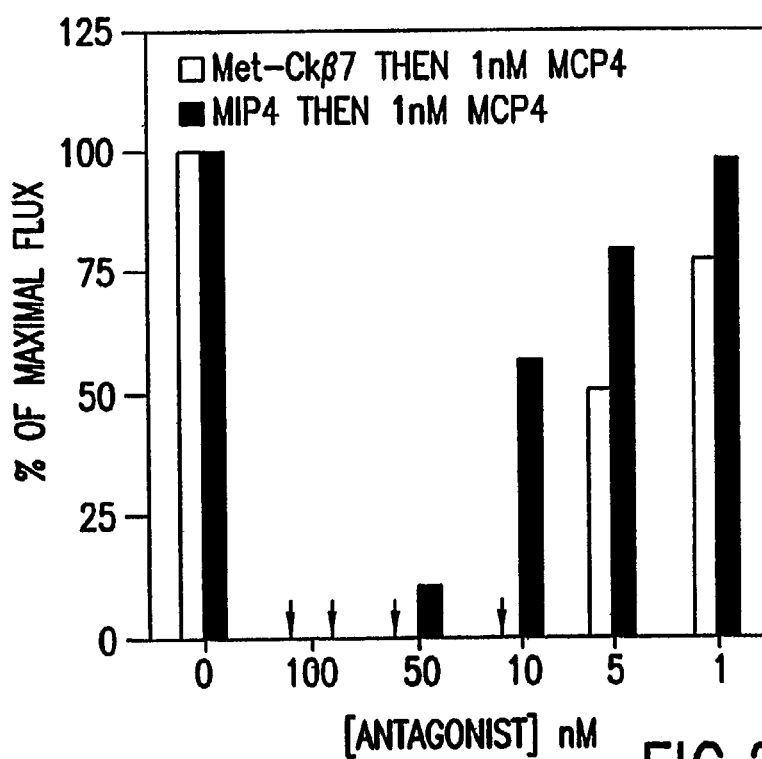

Unmodified MIP4 Also Antagonizes Signaling Through CCR3. Data shown above using radio-iodinated ligands suggested that unmodified MIP4 also displaces ligands from human CCR3. Therefore, the present inventors tested whether the commercially available MIP4 protein, with an N-terminal alanine residue and LKLNA at the C-terminus, was able to affect CCR3 signaling. No CCR3-mediated $Ca^{2+}$ flux was detectable with up to 250 nM MIP4, but surprisingly, this protein exhibited CCR3 antagonistic activity in $Ca^{2+}$ flux assays with Fura-2 loaded HOS-CCR3 cells (FIG. 28) or eosinophils (FIG. 29). However, it is not as potent as Met-Ckβ7* (~5–10-fold less active) showing that the amino acid sequence differences in Met-Ckβ7* amplify a property present in the natural protein. Thus, whilst 10 nM Met-Ckβ7* completely abrogates $Ca^{2+}$ fluxes induced into eosinophils by 1 nM MCP4, only 50% inhibition is seen with MIP4 at this concentration (FIG. 29B). However, at higher concentrations (100 nM), MIP4 is able to completely abrogate signaling induced with 1 nM MCP4. Similar results were obtained with abrogation of 1 nM eotaxin signaling (FIG. 29A); complete inhibition was observed with 50 nM Met-Ckβ7* but 10% of the signal remained in the presence of 100 nM MIP4.

Figure 30B:
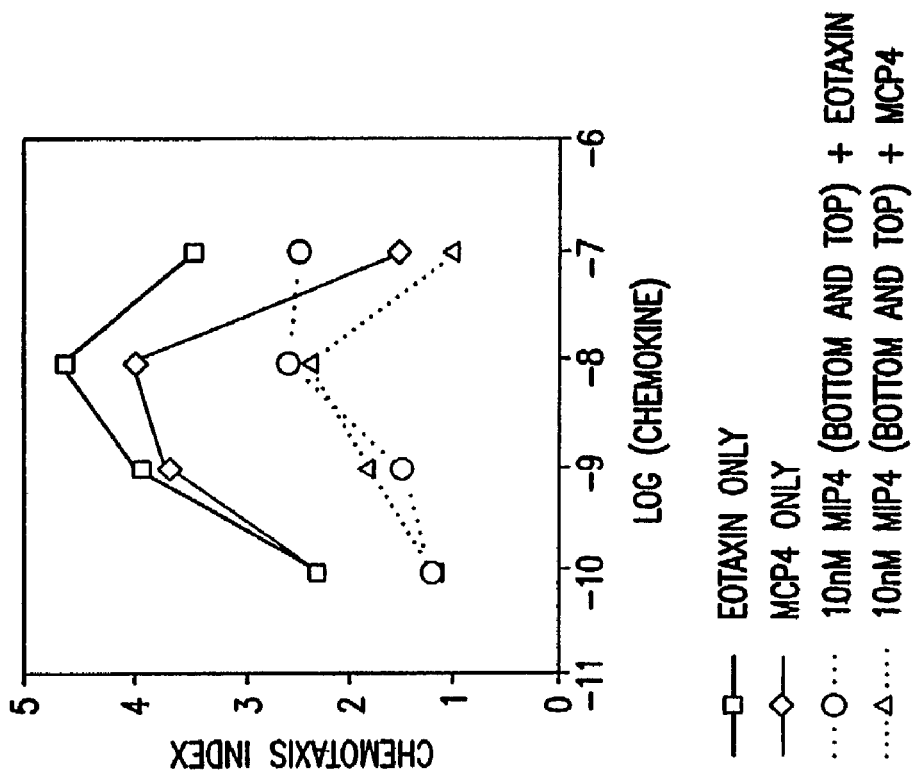
FIGS. 30A–30B show that MIP4 inhibits eosinophil chemotaxis induced by MCP4 or eotaxin. Chemotaxis assays were performed with eosinophils from two donors (A and B) for 3 hrs with a range of MCP4 or eotaxin concentrations. In some experiments, MIP4 was added at 10 nM to the top and bottom chambers of the chemotaxis well as indicated in the key. Chemotaxis index is calculated as the ratio of cells migrated in the test sample compared to cells migrated in buffer alone.
Figure 30A:
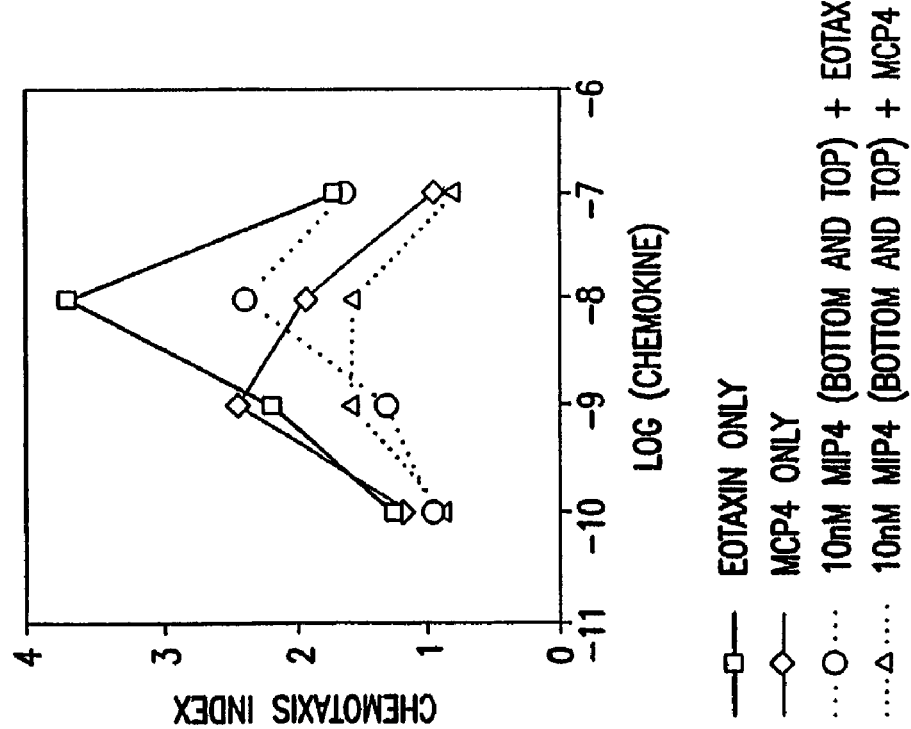
Figure 31A:
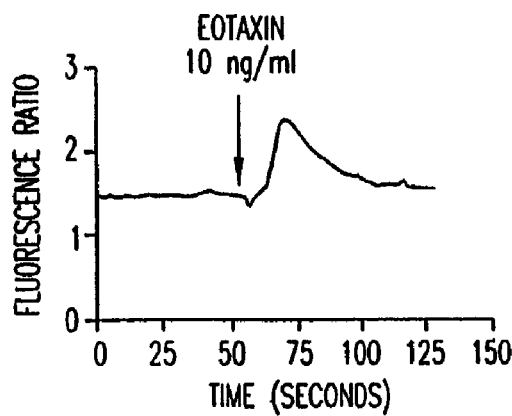
FIGS. 31A–31G show dose-response profile of Met-Ckβ7*-inhibition of eotaxin induced calcium flux in eosinophils. The Met-Ckβ7* used was in the form of a Ckβ7 fragment having amino acids 22–87 in SEQ ID No:2 with a methionine residue at the N-terminus and modification at the C-terminus (Met-22-87-Met-Pro-Glu-Ala). The same donor eosinophils were used in experiments presented in FIGS. 31, 32 and 33.
Figure 31B:
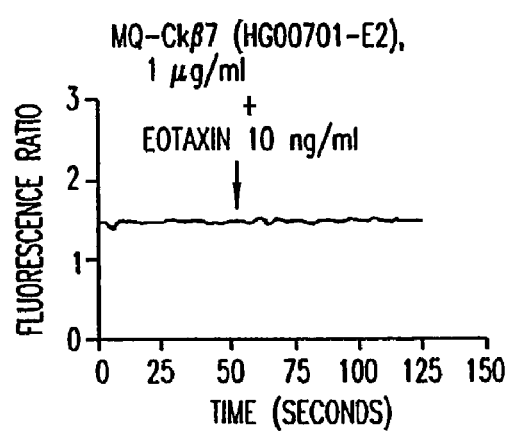
Figure 31C:
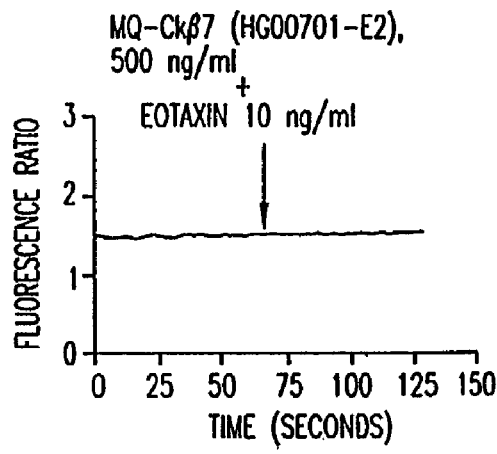
Figure 31D:
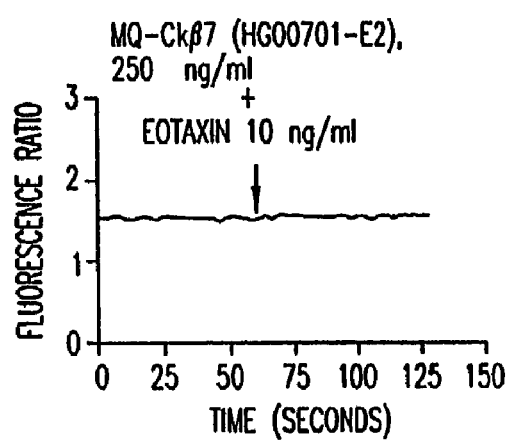
Figure 31E:
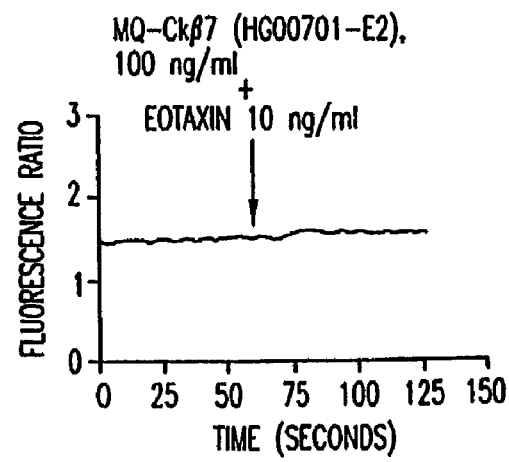
Figure 31F:
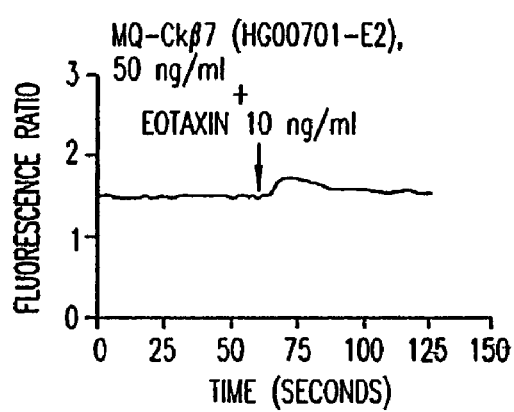
Figure 31G:
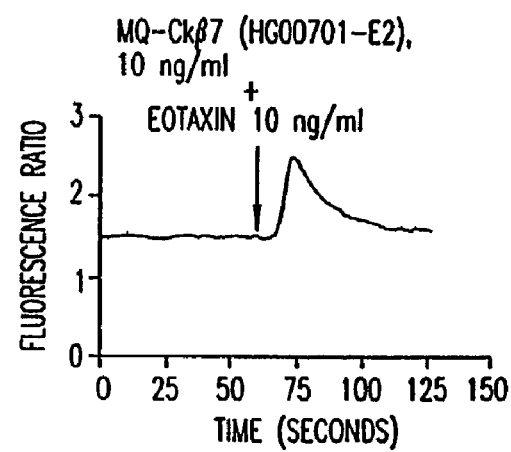
Figure 32A:
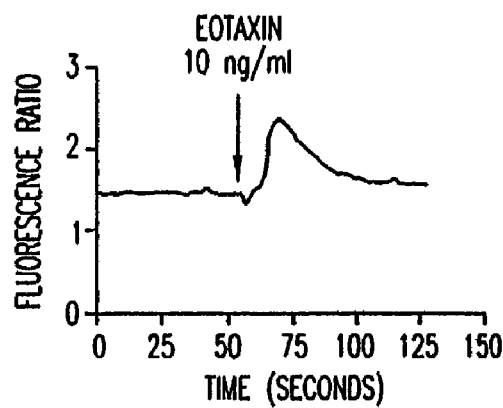
FIGS. 32A–32G show dose-response profile of Met-Ckβ7-inhibition of eotaxin induced calcium flux in eosinophils. The Ckβ7 used was in the form of a Ckβ7 fragment having amino acids 22–89 in SEQ ID No:2 and a methionine residue at the N-terminus (Met-22–89). The same donor eosinophils were used in experiments presented in FIGS. 31, 32 and 33.
Figure 32B:
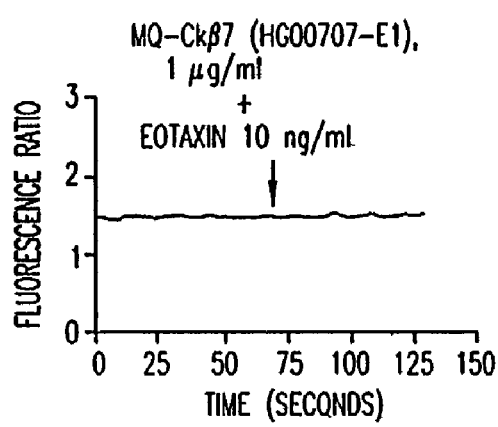
Figure 32C:
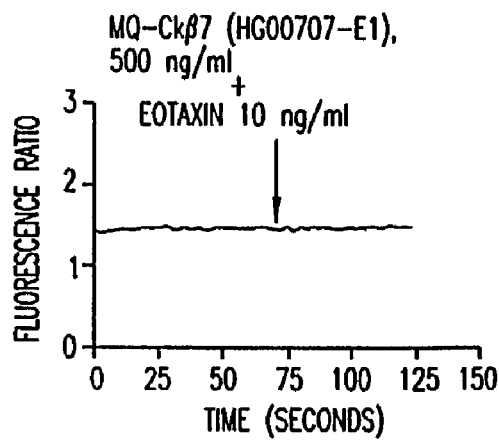
Figure 32D:
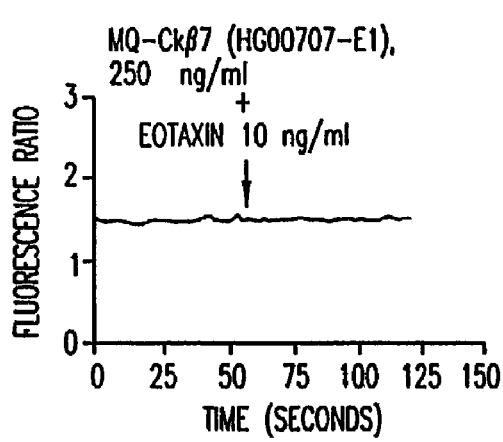
Figure 32E:
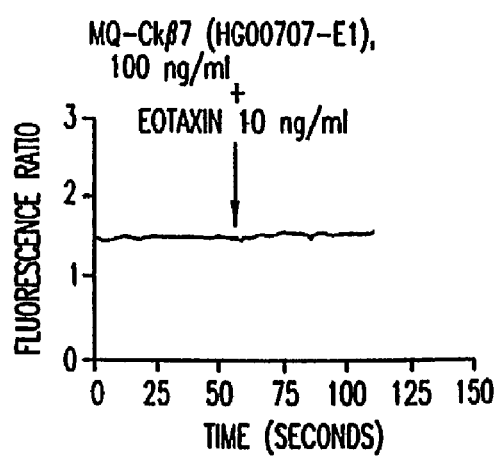
Figure 32F:
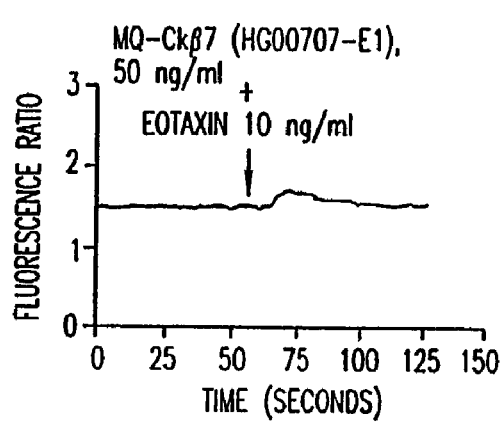
Figure 32G:
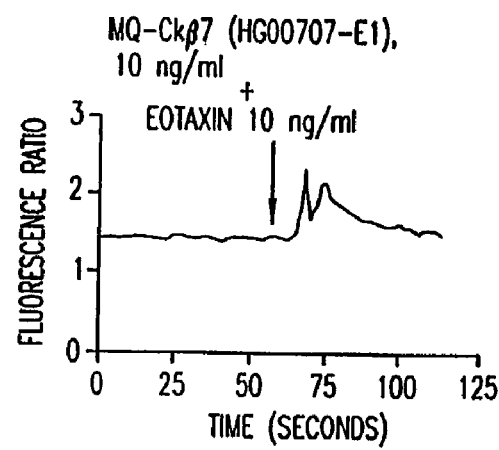
Figure 33:
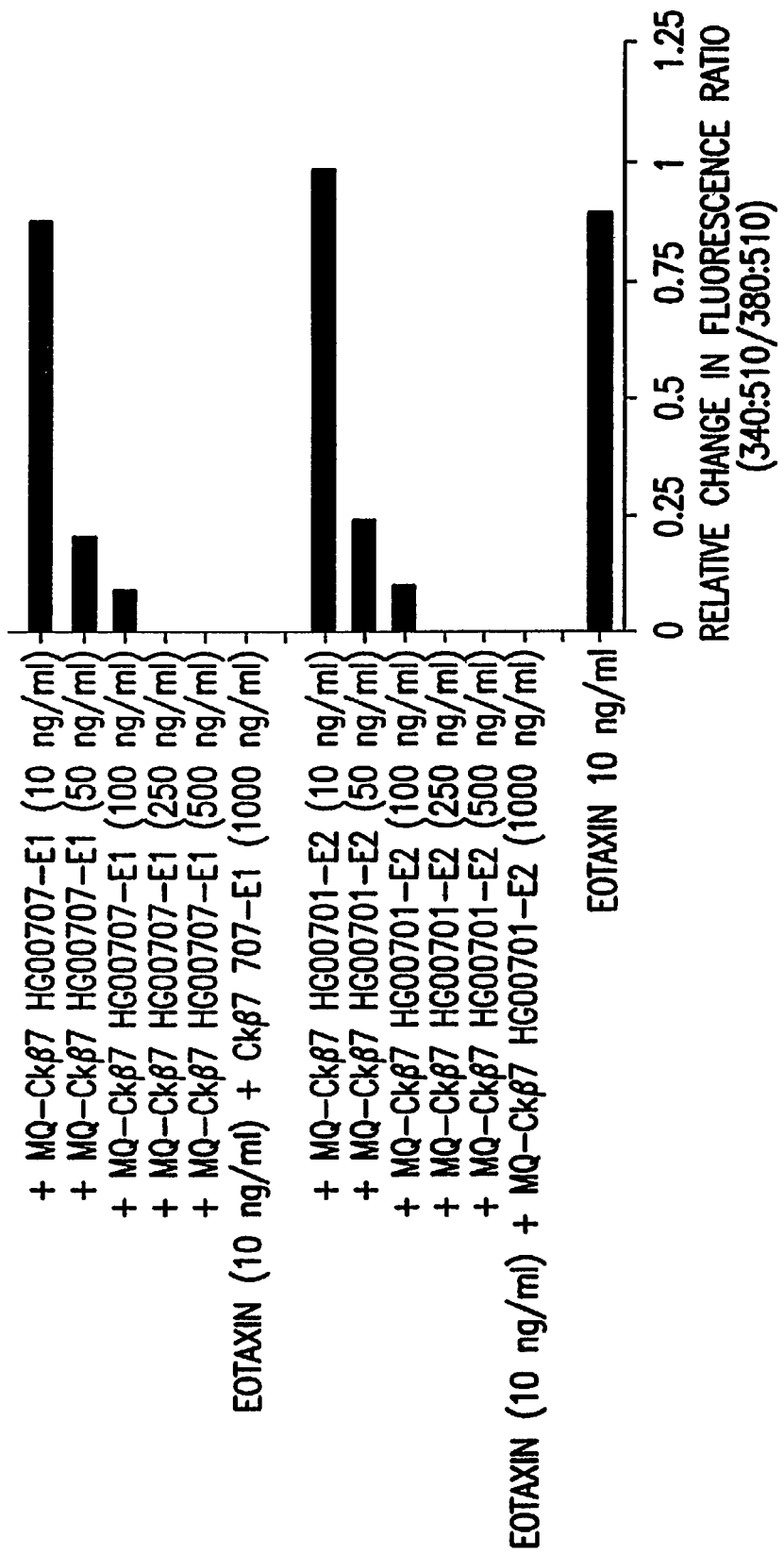
FIG. 33 shows the comparison of the Met-Ckβ7* form in FIG. 31 and the Met-Ckβ7 form in FIG. 32 and demonstrates that the two forms have equivalent antagonist activity.

Chemotaxis Inhibition by MIP4. To extend these observations, the present inventors determined the potency of MIP4 in inhibiting eosinophil chemotaxis using MCP4 or eotaxin—the two most potent CCR3 ligands in this study—as agonists. As above, maximal chemotaxis with these agonists was observed between 1 and 10 nM for both donors tested (FIG. 30). When 10 nM MIP4 was added to the top and bottom chambers of the chemotaxis assay plate, eosinophil chemotaxis induced by 1 nM MCP4 or eotaxin was reduced to near baseline levels, and chemotaxis induced by 10 nM of the agonists was significantly reduced. MIP4 was unable to induce chemotaxis when present in the lower well at concentrations ranging from 0.1 to 100 nM (data not shown). These results corroborate the observations obtained in the $Ca^{2+}$ flux signaling assays, and show that MIP4 inhibits CCR3 function, but that it is less potent than Met-Ckβ7*. The physiological relevance of this observation, with respect to the biological function of MIP4, is discussed below.

Discussion

The present inventors have shown that Met-Ckβ7*, a modified form of the β-chemokine Ckβ7/MIP4 (PARC/DCCK1/AMAC1), is a potent and specific antagonist of CCR3. Met-Ckβ7*, at concentrations as low as 1 nM, is able to completely inhibit eosinophil chemotaxis induced by the most potent CCR3 agonists, eotaxin and MCP4. This antagonist is more effective at inhibiting signaling through CCR3 than Met- or AOP-RANTES. Unlike these modified forms of RANTES, Met-Ckβ7* shows no agonist activity at concentrations up to 1 μM. This specificity and potency make Met-Ckβ7* highly useful as a CCR3 antagonist in vivo for treatment of diseases and states such as allergen-induced eosinophilia. Moreover, bearing in mind the enhanced activity observed with AOP-RANTES compared to Met-RANTES (Simmons, G., et al., Science 276:276 (1997); Mack, M., et al., J. Exp. Med. 187:1215 (1998)), both on CCR3 and other RANTES receptors, forms of MIP4 in which the amino terminus is modified to carry an aminooxypentane group, or some similar moiety, will likely exhibit even higher CCR3 antagonistic potency.

Studies with purified PBMCs or lymphocytes, or with cells stably expressing exogenous chemokine receptors, show that Met-Ckβ7* is highly specific for CCR3. In contrast, CCRs 1, 2, and 5–7, CXCRs 1–4, CX$_3$CR1 and D6 do not show any demonstrable interaction with this protein. However, Met-Ckβ-7* may antagonize other receptors. In particular, the present inventors were unable to test the activity of this protein on the currently uncharacterized MIP4 receptor because of an inability to demonstrate the induction of T cell chemotaxis by MIP4 that has been reported elsewhere (Adema, G. J., et al., *Nature* 387:713 (1997); Hieshima, K., et al., *J. Immunol.* 159:1140 (1997)). Using CD3+ or CD45RA+ sorted peripheral blood T cells from several donors, or ConA/IL-2 activated T cells, MIP4 (produced either in baculovirus-infected insect cells or commercially in bacteria) or Met-Ckβ7* were unable to stimulate detectable chemotaxis or Ca$^{2+}$ signaling at concentrations ranging from 10 μg/ml to 0.1 ng/ml (data not shown). Control chemokines, such as MIP3β, produced robust Ca$^{2+}$ signals and were efficient chemoattractants of these cells. Differences in MIP4 T cell chemotaxis activity may be MIP4 source-specific.

Experiments with radio-iodinated eotaxin, MCP4 and Met-Ckβ7*, demonstrate that Met-Ckβ7* exerts its antagonistic activity by binding CCR3 and sterically preventing activation by CCR3 agonists. The data show that Met-Ckβ7* is able to inhibit eotaxin- and MCP4-induced eosinophil chemotaxis. There is variation in the extent of inhibition by Met-Ckβ7* (FIGS. 26 and 27). Thus, whilst eosinophil chemotaxis from donor A is inhibited effectively with 1 nM Met-Ckβ7* beneath the filter of the assay plate with donor C this concentration of antagonist must be added to the top and bottom of the filter to be fully inhibitory. Indeed, even 10 nM Met-Ckβ-7*, when present beneath the filter only, reduces but does not completely prevent chemotaxis. These results show that Met-Ckβ7* is markedly less potent at inhibiting chemotaxis of eosinophils from donor C, than those from donor A, with donor B falling in between. This is difficult to explain using a model of Met-Ckβ7* antagonism involving, only steric interference. Thus, in some cases, other consequences of Met-Ckβ7*/CCR3 interaction are required to inhibit eosinophil chemotaxis, such as an intracellular signal or internalization of the CCR3 protein, which are variable between individuals. Evidence with other N-terminally modified chemokines indicates that receptor internalization is an important component in their enhanced inhibition of receptor function (Mack, M., et al.,*J. Exp. Med.* 187:1215 (1998); Yang, O. O., et al., *J. Virol.* 73:4582 (1999)). Additionally, different CCR3 ligands exhibit differential effects on this process (Zimmermann, N., et al., *J. Biol. Chem.* 274:12611 (1999)).

Somewhat surprisingly, the unmodified MIP4 protein also has CCR3 antagonistic activity in the signaling and chemotaxis assays used in this study, although it exhibited less potency than Met-Ckβ7*. Thus, the N- and C-terminal differences in Met-Ckβ7* enhance a property present of the unmodified protein. As mentioned in the Results, the present inventors have also generated a protein, Met-Ckβ7, with a carboxy-terminus identical to the commercially-available MIP4 used in this Example, that retains methionine in place of the extreme N-terminal alanine. This protein exhibits identical activity to Met-Ckβ7* in all assays tested (data not shown), demonstrating the importance of this single amino acid change (Ala to Met) in amplifying CCR3 antagonistic activity.

Mechanistically, the strong homology between MIP4 and the CCR3 ligand RANTES (seen over most of the protein except the N-terminus) may be responsible for a weak inhibition of CCR3 activity seen with the MIP4 protein, with the differences in the N-terminus determining whether the receptor can couple to Ca$^{2+}$ fluxing and induce chemotaxis. This two site model for chemokine/chemokine receptor interaction has been proposed for a number of β-chemokines and many studies have demonstrated that small alterations in the amino terminus dramatically affect ligand binding affinity and in some examples, can introduce antagonist activity into proteins that previously acted as agonists (Proudfoot, A. E. I., et al., *J. Biol. Chem.* 271:2599 (1996); Simmons, G., et al., *Science* 276:276 (1997); Proost, P., et al., *J. Biol. Chem.* 273:7222 (1998); Proost, P., et al., *J. Immunol.* 160:4034 (1998); Weber, M., et al., *J. Exp. Med.* 183:681 (1996); Gong, J. H., et al.,*J. Biol. Chem.* 271:10521 (1996); Struyf, S., et al., *Eur. J. Immunol.* 28:1262 (1998)). Replacing the N-terminal alanine of MIP4 with a methionine residue enhances the interaction with CCR3 without introducing agonist activity. Comparison of Met-Ckβ7 to Met-RANTES highlights an alternative explanation for the interaction of CCR3 with MIP4. Met-RANTES, a variant of RANTES that has been extended at the N-terminus by one amino acid (a methionine), is an antagonist for RANTES receptors (Proudfoot, A. E. I., et al.,*J. Biol. Chem.* 271:2599 (1996); Mack, M., et al., *J. Exp. Med.* 187:1215 (1998)). If Met-Ckβ7 acts in a similar fashion, then a −1 variant of MIP4, lacking the first amino acid and starting QVGT, would act as a CCR3 agonist. Interestingly, predictive algorithms of signal peptide cleavage sites of the MIP4 protein suggest that the −1 form of this chemokine is as likely to be produced during protein secretion as the "full-length" protein with the amino-terminal alanine. Whilst production in COS7 and insect cells consistently generates a protein starting AQVGT (see Results and Adema, G. J., et al., *Nature* 387:713 (1997); Heishima, K., et al.,*J. Immunol.* 159:1440(1997)), the −1 variant of MIP4 may be produced and act as a CCR3 agonist.

The CCR3 antagonistic activity of unmodified MIP4 is particularly interesting with respect to the in vivo function of this protein. In chemotaxis assays, concentrations of MIP4 as low as 10 nM were able to significantly reduce eosinophil chemotaxis induced by the most potent known CCR3 agonists, namely eotaxin and MCP4. This level of MIP4 protein is likely achieved in vivo, especially considering the local increases in chemokine concentration caused by immobilization on extracellular matrix components. CCR3 antagonism therefore reflects a property of MIP4 that is of importance in the biology of this chemokine, allowing it to use both agonism and antagonism to control leukocyte cell movement.

It has been reported that MIP4 is produced by dendritic cells and macrophages in the secondary lymphoid tissue, where it has been hypothesized to play a role in the selective attraction of naive T-cells towards antigen presenting cells (Adema, G. J., et al., *Nature* 387:713 (1997)). The data in this Example indicate that this protein also selectively and actively excludes CCR3-positive cells such as basophils, eosinophils and Th2 lymphocytes, from this particular microenvironment. Intriguingly, the CCR3 ligands eotaxin and MCP4 have been demonstrated to act as antagonists for CXCR3, a receptor specifically expressed on Th1 lymphocytes and activated by the β-chemokine SLC (in mice only), and the a-chemokines IP-10 and Mig (Sallusto, F., et al., *J. Exp. Med.* 187:875 (1998); Bonecchi, R., et al.,*J. Exp. Med.* 187:129 (1998); Weng, Y., et al., *J. Biol. Chem.* 273:18288

(1998); Soto, H., et al., *Proc. Natl. Acad. Sci. USA* 95:8205 (1998); Jenh, C.-H., et al., *J. Immunol.* 162:3765 (1999)). Whilst CXCR3 interactions with eotaxin and MCP4 were shown to be fairly weak, akin to that seen for MIP4 on CCR3, again it may be of physiological relevance and play a role in the inhibition of Th1 T cells into sites characterized by Th2 cell influx (Weng, Y., et al., *J. Biol. Chem.* 273:18288 (1998)). Thus, the use of receptor antagonism is an emerging theme in the regulation of leukocyte movement during inflammation and immunity. It would be of interest to examine whether other examples of this phenomenon exist with chemokine receptors that are specifically involved in the attraction of leukocyte subsets, such as CCR4 (known ligand are TARC and MDC) and CCR8 (known ligands are 1-309, TARC and MIP-1β) that are found preferentially on Th2 cells (Sallusto, F., et al., *J. Exp. Med.* 187:875 (1998); Zingoni, A., et al., *J. Immunol.* 161:547 (1998); Bernadini, G., et al., *Eur. J. Immunol.* 28:582 (1998)). Also, it would be worthwhile examining whether CCR3 ligands such as eotaxin and MCP4 are able to exhibit reciprocal antagonism of the currently uncharacterized MIP4 receptor.

EXAMPLE 5

Protein Batch Information

A summary of the source, name, expression system, and N- and C-terminal sequence information for the protein batches in the figures is shown in Table 2. Line 12 shows a Ckβ-1-1 sequence beginning with MTNKE at the N-terminus (SEQ ID NO:17) and line 14 shows a Ckβ-1 sequence beginning with MVGTN at the N-terminus (SEQ ID NO:18).

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

TABLE 2

Batches of CK-beta 7

| Source | Name | expression | RP-HPL | MW exptected | MW observed | n-term | C-terminal Analysis |
|---|---|---|---|---|---|---|---|
| PeproTech | MIP-4 | e. coli | | 7851 | 7852 | AQVGT 95% | ? |
| PeproTech | MIP-4 | e. coli | | 7851 | 7851 | | ? |
| R&D Systems | rhuPARC-APQ01 | e. coli | | 7851 | 7852 | AQVGT 95% | ? |
| R&D Systems | rhuPARC-APQ02 | e. coli | | 7851 | 7852 | AQVGT 95% | ? |
| HGS | hg00702-e1 | e. coli | | 7851 | 7853 | AQVGT 98% | |
| HGS | hg00701-e2 | e. coli | | 7911 | 8155 | MQVGT 95% | LKLMPEA/. . . eA |
| HGS | hg00700-b4 | baculo | | 7851 | 7496/7852 | AQVGT/TNKEL 40/60% | |
| HGS | hg00700-b6 | baculo | | | | AQVGT/TNKEL 85/15% | |
| HGS | hg00700-b7 | baculo | | 7851 | 7852 | AQVGT/TNKEL 85/10% | ? |
| HGS | hg00707-e1 | e. coli | | 7911 | 7911 | MQVGT 95% | MQVG. . .KLNA |
| HGS | hg00703-e1 | e. coli | | | | MTNKE 95% | |
| HGS | hg00706-c1 | CHO | | | | AQVGT 95% | |
| HGS | hg00708-e1 | e. coli | | | | MVGTN/VGTNK 90/5% | |

| | expect | observed | obs-expect |
|---|---|---|---|
| hg00701-e2 | | | |
| MQVGTN-KLMPEA - by c-term | 8155 | 8155.0 | 0.4 |
| MQVGTN-KLNA | 7911.3 | 8155.0 | 243.7 |
| hg00702-e1 | | | |
| AQVGT-KLNA | 7851.2 | 7853.0 | 1.8 |
| hg00707-e1 | | | |
| MQVGT-KLNA | 7911.3 | 7911.0 | -0.3 |

What is claimed is:

1. An isolated protein comprising the amino acid sequence of SEQ ID NO:16.

2. The isolated protein of claim 1 further comprising a heterologous polypeptide.

3. The isolated protein of claim 2 wherein the heterologous polypeptide comprises the Fc domain of immunoglobulin.

4. The isolated protein of claim 1 wherein the protein further comprises a chemical moiety.

5. The isolated protein of claim 4 wherein the chemical moiety is polyethylene glycol.

6. The isolated protein of claim 1 which is glycosylated.

7. The isolated protein of claim 1 which is produced by a host cell.

8. The isolated protein of claim 1 which is chemically synthesized.

9. A composition comprising the isolated protein of claim 1 and a pharmaceutically acceptable carrier.

10. An isolated chemokine β-7 variant polypeptide selected from the group consisting of:
   (a) a polypeptide at least 90% identical to SEQ ID NO:16; and
   (b) a polypeptide comprising the amino acid sequence of SEQ ID NO:16 except for up to ten amino acid substitutions
   wherein said variant polypeptide inhibits the calcium flux induced in eosinophils by eotaxin, MCP-4, RANTES, MCP-3, eotaxin-2.

11. The isolated chemokine β-7 variant polypeptide of claim 10, wherein said variant polypeptide is (a).

12. The isolated chemokine β-7 variant polypeptide of claim 10, wherein said variant polypeptide is (b).

13. The isolated chemokine β-7 variant polypeptide of claim 10 further comprising a heterologous polypeptide.

14. The isolated chemokine β-7 variant polypeptide of claim 13 wherein the heterologous polypeptide comprises the Fc domain of immunoglobulin.

15. The isolated chemokine β-7 variant polypeptide of claim 10 wherein the polypeptide further comprises a chemical moiety.

16. The isolated chemokine β-7 variant polypeptide of claim 15 wherein the chemical moiety is polyethylene glycol.

17. The isolated chemokine β-7 variant polypeptide of claim 10 which is glycosylated.

18. The isolated chemokine β-7 variant polypeptide of claim 10 which is produced by a host cell.

19. The isolated chemokine β-7 variant polypeptide of claim 10 which is chemically synthesized.

20. A composition comprising the isolated chemokine β-7 variant polypeptide of claim 10 and a pharmaceutically acceptable carrier.

* * * * *

SEQUENCE LISTING

<160> NUMBER OF SEQ ID NOS: 18

<210> SEQ ID NO 1
<211> LENGTH: 270
<212> TYPE: DNA
<213> ORGANISM: Homo sapiens
<220> FEATURE:
<221> NAME/KEY: CDS
<222> LOCATION: (1)..(267)

-continued

```
<400> SEQUENCE: 1 atg aag ggc ctt gca gct gcc ctc ctt gtc ctc gtc tgc acc atg gcc      48
Met Lys Gly Leu Ala Ala Ala Leu Leu Val Leu Val Cys Thr Met Ala
1               5                   10                  15 ctc tgc tcc tgt gca caa gtt ggt acc aac aaa gag ctc tgc tgc ctc      96
Leu Cys Ser Cys Ala Gln Val Gly Thr Asn Lys Glu Leu Cys Cys Leu
                20                  25                  30 gtc tat acc tcc tgg cag att cca caa aag ttc ata gtt gac tat tct     144
Val Tyr Thr Ser Trp Gln Ile Pro Gln Lys Phe Ile Val Asp Tyr Ser
            35                  40                  45 gaa acc agc ccc cag tgc ccc aag cca ggt gtc atc ctc cta acc aag     192
Glu Thr Ser Pro Gln Cys Pro Lys Pro Gly Val Ile Leu Leu Thr Lys
        50                  55                  60 aga ggc cgg cag atc tgt gct gac ccc aat aag aag tgg gtc cag aaa     240
Arg Gly Arg Gln Ile Cys Ala Asp Pro Asn Lys Lys Trp Val Gln Lys
65                  70                  75                  80 tac atc agc gac ctg aag ctg aat gcc tga                             270
Tyr Ile Ser Asp Leu Lys Leu Asn Ala
                85
```

<210> SEQ ID NO 2
<211> LENGTH: 89
<212> TYPE: PRT
<213> ORGANISM: Homo sapiens

<400> SEQUENCE: 2

```
Met Lys Gly Leu Ala Ala Ala Leu Leu Val Leu Val Cys Thr Met Ala
1               5                   10                  15

Leu Cys Ser Cys Ala Gln Val Gly Thr Asn Lys Glu Leu Cys Cys Leu
                20                  25                  30

Val Tyr Thr Ser Trp Gln Ile Pro Gln Lys Phe Ile Val Asp Tyr Ser
            35                  40                  45

Glu Thr Ser Pro Gln Cys Pro Lys Pro Gly Val Ile Leu Leu Thr Lys
        50                  55                  60

Arg Gly Arg Gln Ile Cys Ala Asp Pro Asn Lys Lys Trp Val Gln Lys
65                  70                  75                  80

Tyr Ile Ser Asp Leu Lys Leu Asn Ala
                85
```

<210> SEQ ID NO 3
<211> LENGTH: 93
<212> TYPE: PRT
<213> ORGANISM: Homo sapiens

<400> SEQUENCE: 3

```
Met Gln Val Ser Thr Ala Ala Leu Ala Val Leu Leu Cys Thr Met Ala
1               5                   10                  15

Leu Cys Asn Gln Val Leu Ser Ala Pro Leu Ala Ala Asp Thr Pro Thr
                20                  25                  30

Ala Cys Cys Phe Ser Tyr Thr Ser Arg Gln Ile Pro Gln Asn Phe Ile
            35                  40                  45

Ala Asp Tyr Phe Glu Thr Ser Ser Gln Cys Ser Lys Pro Ser Val Ile
        50                  55                  60

Phe Leu Thr Lys Arg Gly Arg Gln Val Cys Ala Asp Pro Ser Glu Glu
65                  70                  75                  80

Trp Val Gln Lys Tyr Val Ser Asp Leu Glu Leu Ser Ala
                85                  90
```

<210> SEQ ID NO 4
<211> LENGTH: 3974
<212> TYPE: DNA
<213> ORGANISM: Homo sapiens

<400> SEQUENCE: 4

```
ggtacctaag tgagtagggc gtccgatcga cggacgcctt ttttttgaat tcgtaatcat      60
ggtcatagct gtttcctgtg tgaaattgtt atccgctcac aattccacac aacatacgag     120
ccggaagcat aaagtgtaaa gcctggggtg cctaatgagt gagctaactc acattaattg     180
cgttgcgctc actgcccgct ttccagtcgg gaaacctgtc gtgccagctg cattaatgaa     240
tcggccaacg cgcggggaga ggcggtttgc gtattgggcg ctcttccgct tcctcgctca     300
ctgactcgct gcgctcggtc gttcggctgc ggcgagcggt atcagctcac tcaaaggcgg     360
taatacggtt atccacagaa tcaggggata acgcaggaaa gaacatgtga gcaaaaggcc     420
agcaaaaggc caggaaccgt aaaaaggccg cgttgctggc gtttttccat aggctccgcc     480
cccctgacga gcatcacaaa aatcgacgct caagtcagag gtggcgaaac ccgacaggac     540
tataaagata ccaggcgttt ccccctggaa gctccctcgt gcgctctcct gttccgaccc     600
tgccgcttac cggatacctg tccgcctttc tcccttcggg aagcgtggcg ctttctcata     660
gctcacgctg taggtatctc agttcggtgt aggtcgttcg ctccaagctg ggctgtgtgc     720
acgaaccccc cgttcagccc gaccgctgcg ccttatccgg taactatcgt cttgagtcca     780
acccggtaag acacgactta tcgccactgg cagcagccac tggtaacagg attagcagag     840
cgaggtatgt aggcggtgct acagagttct tgaagtggtg gcctaactac ggctacacta     900
gaagaacagt atttggtatc tgcgctctgc tgaagccagt taccttcgga aaaagagttg     960
gtagctcttg atccggcaaa caaaccaccg ctggtagcgg tggttttttt gtttgcaagc    1020
agcagattac gcgcagaaaa aaaggatctc aagaagatcc tttgatcttt tctacggggt    1080
ctgacgctca gtggaacgaa aactcacgtt aagggatttt ggtcatgaga ttatcgtcga    1140
caattcgcgc gcgaaggcga agcggcatgc atttacgttg acaccatcga atggtgcaaa    1200
acctttcgcg gtatggcatg atagcgcccg gaagagagtc aattcagggt ggtgaatgtg    1260
aaaccagtaa cgttatacga tgtcgcagag tatgccggtg tctcttatca gaccgtttcc    1320
cgcgtggtga accaggccag ccacgtttct gcgaaaacgc gggaaaaagt ggaagcggcg    1380
atggcggagc tgaattacat tcccaaccgc gtggcacaac aactggcggg caaacagtcg    1440
ttgctgattg gcgttgccac ctccagtctg gccctgcacg cgccgtcgca aattgtcgcg    1500
gcgattaaat ctcgcgccga tcaactgggt gccagcgtgg tggtgtcgat ggtagaacga    1560
agcggcgtcg aagcctgtaa agcggcggtg cacaatcttc tcgcgcaacg cgtcagtggg    1620
ctgatcatta actatccgct ggatgaccag gatgccattg ctgtggaagc tgcctgcact    1680
aatgttccgg cgttatttct tgatgtctct gaccagacac ccatcaacag tattattttc    1740
tcccatgaag acgtacgcg actgggcgtg gagcatctgg tcgcattggg tcaccagcaa    1800
atcgcgctgt tagcgggccc attaagttct gtctcggcgc gtctgcgtct ggctggctgg    1860
cataaatatc tcactcgcaa tcaaattcag ccgatagcgg aacgggaagg cgactggagt    1920
gccatgtccg gttttcaaca aaccatgcaa atgctgaatg agggcatcgt tcccactgcg    1980
atgctggttg ccaacgatca gatggcgctg ggcgcaatgc gcgccattac cgagtccggg    2040
ctgcgcgttg gtgcggatat ctcggtagtg ggatacgacg ataccgaaga cagctcatgt    2100
tatatcccgc cgttaaccac catcaaacag gattttcgcc tgctggggca aaccagcgtg    2160
```

```
gaccgcttgc tgcaactctc tcagggccag gcggtgaagg gcaatcagct gttgcccgtc    2220
tcactggtga aagaaaaac cacctggcg cccaatacgc aaaccgcctc tccccgcgcg      2280
ttggccgatt cattaatgca gctggcacga caggtttccc gactggaaag cgggcagtga   2340
gcgcaacgca attaatgtaa gttagcgcga attgtcgacc aaagcggcca tcgtgcctcc   2400
ccactcctgc agttcggggg catggatgcg cggatagccg ctgctggttt cctggatgcc   2460
gacggatttg cactgccggt agaactccgc gaggtcgtcc agcctcaggc agcagctgaa   2520
ccaactcgcg aggggatcga gcccggggtg ggcgaagaac tccagcatga atccccgcg    2580 ctggaggatc atccagccgg cgtcccggaa aacgattccg aagcccaacc tttcatagaa   2640
ggcggcggtg gaatcgaaat ctcgtgatgg caggttgggc gtcgcttggt cggtcatttc   2700
gaaccccaga gtcccgctca agaactcg tcaagaaggc gatagaaggc gatgcgctgc     2760
gaatcgggag cggcgatacc gtaaagcacg aggaagcggt cagcccattc gccgccaagc   2820
tcttcagcaa tatcacgggt agccaacgct atgtcctgat agcggtccgc cacacccagc   2880
cggccacagt cgatgaatcc agaaaagcgg ccattttcca ccatgatatt cggcaagcag   2940
gcatcgccat gggtcacgac gagatcctcg ccgtcgggca tgcgcgcctt gagcctggcg   3000
aacagttcgg ctggcgcgag cccctgatgc tcttcgtcca gatcatcctg atcgacaaga   3060
ccggcttcca tccgagtacg tgctcgctcg atgcgatgtt tcgcttggtg gtcgaatggg   3120
caggtagccg gatcaagcgt atgcagccgc cgcattgcat cagccatgat ggatactttc   3180
tcggcaggag caaggtgaga tgacaggaga tcctgccccg gcacttcgcc caatagcagc   3240
cagtcccttc ccgcttcagt gacaacgtcg agcacagctg cgcaaggaac gcccgtcgtg   3300
gccagccacg atagccgcgc tgcctcgtcc tgcagttcat tcagggcacc ggacaggtcg   3360
gtcttgacaa aagaaccgg gcgcccctgc gctgacagcc ggaacacggc ggcatcagag    3420
cagccgattg tctgttgtgc ccagtcatag ccgaatagcc tctccaccca gcggccgga    3480 gaacctgcgt gcaatccatc ttgttcaatc atgcgaaacg atcctcatcc tgtctcttga   3540
tcagatcttg atccctgcg ccatcagatc cttggcggca agaaagccat ccagtttact    3600
ttgcagggct tcccaacctt accagagggc gccccagctg gcaattccgg ttcgcttgct   3660
gtccataaaa ccgcccagtc tagctatcgc catgtaagcc cactgcaagc tacctgcttt   3720
ctctttgcgc ttgcgttttc ccttgtccag atagcccagt agctgacatt catccggggt   3780
cagcaccgtt tctgcggact ggctttctac gtgttccgct tcctttagca gcccttgcgc   3840
cctgagtgct tgcggcagcg tgaagcttaa aaaactgcaa aaatagtttt gacttgtgag   3900
cggataacaa ttaagatgta cccaattgtg agcggataac aatttcacac attaagagg    3960 agaaattaca tatg                                                     3974

<210> SEQ ID NO 5
<211> LENGTH: 112
<212> TYPE: DNA
<213> ORGANISM: Homo sapiens

<400> SEQUENCE: 5
aagcttaaaa aactgcaaaa aatagtttga cttgtgagcg gataacaatt aagatgtacc    60
caattgtgag cggataacaa tttcacacat taaagaggag aaattacata tg           112

<210> SEQ ID NO 6
<211> LENGTH: 27
<212> TYPE: DNA
```

<210> SEQ ID NO 6
<211> LENGTH: 27
<212> TYPE: DNA
<213> ORGANISM: Homo sapiens

<400> SEQUENCE: 6
tcaggatcct gtgcacaagt tggtacc                              27

<210> SEQ ID NO 7
<211> LENGTH: 26
<212> TYPE: DNA
<213> ORGANISM: Homo sapiens

<400> SEQUENCE: 7
cgctctagag taaaacgacg gccagt                               26

<210> SEQ ID NO 8
<211> LENGTH: 27
<212> TYPE: DNA
<213> ORGANISM: Homo sapiens

<400> SEQUENCE: 8
tcaggatccc aagttggtac caacaaa                              27

<210> SEQ ID NO 9
<211> LENGTH: 27
<212> TYPE: DNA
<213> ORGANISM: Homo sapiens

<400> SEQUENCE: 9
tcaggatccg ttggtaccaa caaagag                              27

<210> SEQ ID NO 10
<211> LENGTH: 27
<212> TYPE: DNA
<213> ORGANISM: Homo sapiens

<400> SEQUENCE: 10
tcaggatccg gtaccaacaa agagctc                              27

<210> SEQ ID NO 11
<211> LENGTH: 30
<212> TYPE: DNA
<213> ORGANISM: Homo sapiens

<400> SEQUENCE: 11
ggaaagctta tgaagggcct tgcagctgcc                           30

<210> SEQ ID NO 12
<211> LENGTH: 57
<212> TYPE: DNA
<213> ORGANISM: Homo sapiens

<400> SEQUENCE: 12
cgctctagat caagcgtagt ctgggacgtc gtatgggtag gcattcagct tcaggtc    57

<210> SEQ ID NO 13
<211> LENGTH: 33
<212> TYPE: DNA
<213> ORGANISM: Homo sapiens

<400> SEQUENCE: 13
aaaggatccg ccaccatgaa gggccttgca agc                       33

<210> SEQ ID NO 14
<211> LENGTH: 27

<212> TYPE: DNA
<213> ORGANISM: Homo sapiens

<400> SEQUENCE: 14
aaaggatcct caggcattca gcttcag     27

<210> SEQ ID NO 15
<211> LENGTH: 69
<212> TYPE: PRT
<213> ORGANISM: Homo sapiens

<400> SEQUENCE: 15

Met Gln Val Gly Thr Asn Lys Glu Leu Cys Cys Leu Val Tyr Thr Ser
1               5                   10                  15

Trp Gln Ile Pro Gln Lys Phe Ile Val Asp Tyr Ser Glu Thr Ser Pro
            20                  25                  30

Gln Cys Pro Lys Pro Gly Val Ile Leu Leu Thr Lys Arg Gly Arg Gln
        35                  40                  45

Ile Cys Ala Asp Pro Asn Lys Lys Trp Val Gln Lys Tyr Ile Ser Asp
    50                  55                  60

Leu Lys Leu Asn Ala
65

<210> SEQ ID NO 16
<211> LENGTH: 71
<212> TYPE: PRT
<213> ORGANISM: Homo sapiens

<400> SEQUENCE: 16

Met Gln Val Gly Thr Asn Lys Glu Leu Cys Cys Leu Val Tyr Thr Ser
1               5                   10                  15

Trp Gln Ile Pro Gln Lys Phe Ile Val Asp Tyr Ser Glu Thr Ser Pro
            20                  25                  30

Gln Cys Pro Lys Pro Gly Val Ile Leu Leu Thr Lys Arg Gly Arg Gln
        35                  40                  45

Ile Cys Ala Asp Pro Asn Lys Lys Trp Val Gln Lys Tyr Ile Ser Asp
    50                  55                  60

Leu Lys Leu Met Pro Glu Ala
65              70

<210> SEQ ID NO 17
<211> LENGTH: 66
<212> TYPE: PRT
<213> ORGANISM: Homo sapiens

<400> SEQUENCE: 17

Met Thr Asn Lys Glu Leu Cys Cys Leu Val Tyr Thr Ser Trp Gln Ile
1               5                   10                  15

Pro Gln Lys Phe Ile Val Asp Tyr Ser Glu Thr Ser Pro Gln Cys Pro
            20                  25                  30

Lys Pro Gly Val Ile Leu Leu Thr Lys Arg Gly Arg Gln Ile Cys Ala
        35                  40                  45

Asp Pro Asn Lys Lys Trp Val Gln Lys Tyr Ile Ser Asp Leu Lys Leu
    50                  55                  60

Asn Ala
65

<210> SEQ ID NO 18
<211> LENGTH: 68

```
-continued

<212> TYPE: PRT
<213> ORGANISM: Homo sapiens

<400> SEQUENCE: 18

Met Val Gly Thr Asn Lys Glu Leu Cys Cys Leu Val Tyr Thr Ser Trp
1               5                   10                  15

Gln Ile Pro Gln Lys Phe Ile Val Asp Tyr Ser Glu Thr Ser Pro Gln
                20                  25                  30

Cys Pro Lys Pro Gly Val Ile Leu Leu Thr Lys Arg Gly Arg Gln Ile
            35                  40                  45

Cys Ala Asp Pro Asn Lys Lys Trp Val Gln Lys Tyr Ile Ser Asp Leu
        50                  55                  60

Lys Leu Asn Ala
65
```